(12) United States Patent
Gudmundsson et al.

(10) Patent No.: US 7,247,626 B2
(45) Date of Patent: Jul. 24, 2007

(54) PYRAZOLOPYRIMIDINE DERIVATIVES AND PHARMACEUTICAL COMPOSITIONS CONTAINING THEM

(75) Inventors: Kristjan Gudmundsson, Durham, NC (US); Brian A Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 428 days.

(21) Appl. No.: 10/505,386

(22) PCT Filed: Feb. 24, 2003

(86) PCT No.: PCT/US03/05704

§ 371 (c)(1),
(2), (4) Date: Aug. 20, 2004

(87) PCT Pub. No.: WO03/076441

PCT Pub. Date: Sep. 18, 2003

(65) Prior Publication Data

US 2005/0124616 A1    Jun. 9, 2005

Related U.S. Application Data

(60) Provisional application No. 60/362,298, filed on Mar. 7, 2002.

(51) Int. Cl.
- A61K 31/519 (2006.01)
- C07D 487/04 (2006.01)
- A61P 31/22 (2006.01)

(52) U.S. Cl. .................. 514/233.2; 544/281; 544/117; 514/259.1

(58) Field of Classification Search .............. None
See application file for complete search history.

(56) References Cited

U.S. PATENT DOCUMENTS 6,313,124 B1    11/2001    He et al.

FOREIGN PATENT DOCUMENTS

| | | |
|---|---|---|
| JP | 20000038350 | 2/2000 |
| WO | WO 96/34866 | 11/1996 |
| WO | WO 98/03510 | 1/1998 |
| WO | WO 98/08847 | 3/1998 |
| WO | WO 98/56377 | 12/1998 |
| WO | WO 99/64419 | 12/1999 |
| WO | WO 00/59907 | 10/2000 |
| WO | WO 01/23387 | 4/2001 |
| WO | WO 01/23388 | 4/2001 |
| WO | WO 02/04424 | 1/2002 |
| WO | WO 02/078700 | 1/2002 |
| WO | WO 02/48147 | 6/2002 |
| WO | WO 02/48148 | 6/2002 |
| WO | WO 02/088124 | 6/2002 |
| WO | WO 02/066481 | 8/2002 |
| WO | WO 02/072581 | 9/2002 |
| WO | WO 02/078701 | 10/2002 |
| WO | WO 02/083672 | 10/2002 |
| WO | WO 03/000689 | 1/2003 |
| WO | WO 03/022845 | 3/2003 |
| WO | WO 03/031446 | 4/2003 |
| WO | WO 03/050120 | 6/2003 |
| WO | WO 03/095455 | 11/2003 |
| WO | WO 04/033454 | 4/2004 |

*Primary Examiner*—James O. Wilson
*Assistant Examiner*—Susanna Moore
(74) *Attorney, Agent, or Firm*—Lorie Ann Morgan

(57) ABSTRACT

The present invention provides compounds of formula (I):

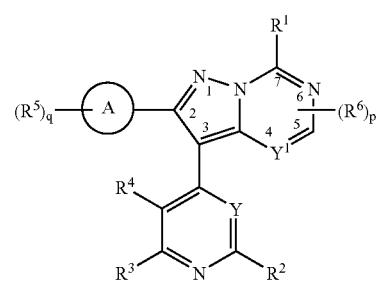

pharmaceutical compositions containing the same, processes for preparing the same and their use as pharmaceutical agents.

28 Claims, No Drawings

PYRAZOLOPYRIMIDINE DERIVATIVES AND PHARMACEUTICAL COMPOSITIONS CONTAINING THEM

CROSS REFERENCES TO RELATED APPLICATIONS

This application is a 371 Application of PCT/US03/05704, filed 24 Feb. 2003, which claims priority to U.S. Application Ser. No. 60/362,298, filed 7 Mar. 2002.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2. a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry HSV-1, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varicella zoster virus (VZ) (also know as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZ is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

BRIEF SUMMARY OF THE INVENTION

According to a first aspect of the invention there is provided compounds of formula (I):

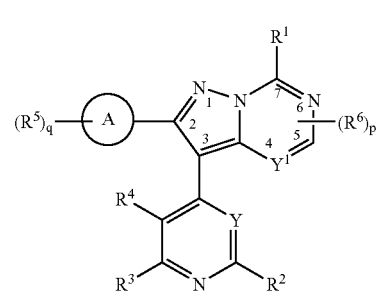

I wherein:

$R^1$ is selected from the group consisting of H, halo, alkyl, alkenyl, alkynyl, cycloalkyl, cycloalkenyl, Ay, Het, —C(O)$R^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —OR$^7$, —OAy, —OHet, —NR$^7R^8$, —NR$^7$Ay, —NHHet, —S(O)$_nR^9$, —S(O)$_n$Ay, —S(O)$_n$Het, —S(O)$_2$NR$^7R^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7R^8$, —R$^{10}$NR$^7$Ay, —R$^{10}$NHSO$_2R^9$, —R$^{10}$(C(O)R$^9$, —R$^{10}$C(O)Ay, —R$^{10}$C(O)Het, —R$^{10}$CO$_2R^9$, —R$^{10}$OC(O)R$^9$, —R$^{10}$OC(O)Ay, —R$^{10}$OC(O)Het, —R$^{10}$C(O)NR$^9R^{11}{}_1$, —R$^{10}$C(O)NR$^7$Ay, —R$^{10}$C(O)NHR$^{10}$Het, —R$^{10}$C(S)NR$^9R^{11}$, —R$^{10}$C(NH)NR$^9R^{11}$, —R$^{10}$SO$_2R^9$, —R$^{10}$SO$_2$NR$^9R^{11}$, —R$^{10}$SO$_2$NHCOR$^9$, —R$^{10}$OS(O)$_nR^9$, cyano, nitro and azido;

each $R^7$ and $R^9$ are the same or different and are independently selected from the group consisting of H, alkyl, cycloalkyl, alkenyl, cycloalkenyl, —C(O)R$^9$, —CO$_2R^9$, —C(O)NR$^9R^{11}$, —C(S)NR$^9R^{11}$, —C(NH)NR$^9R^{11}$, —SO$_2R^{10}$, —SO$_2$NR$^9R^{11}$, —R$^{10}$cycloalkyl, —R$^{10}$Ay, —R$^{10}$Het, —R$^{10}$OC(O)R$^9$, —R$^{10}$CO$_2R^9$, —R$^{10}$C(O)NR$^9R^{11}$, —R$^{10}$C(S)NR$^9R^{11}$, —R$^{10}$OR$^9$, —R$^{10}$NR$^9R^{11}$, —R$^{10}$NHCOR$^9$, —R$^{10}$NHC(NH)NR$^9R^{11}$, —R$^{10}$C(NH)NR$^9R^{11}$, —R$^{10}$NHSO$_2R^9$, —R$^{10}$SO$_2$NR$^9R^{11}$, —R$^{10}$SO$_2R^{10}$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1–10, and —R$^{10}$NR$^{10}R^{10}$;

each $R^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

$Y^1$ is N or CH;

p is 0, 1 or 2 when $Y^1$ is CH, p is 0 or 1 when $Y^1$ is N;

each $R^6$ is the same or different and is independently selected from the group consisting of H, halo, alkyl, alkenyl, alkynyl, cycloalkyl, cycloalkenyl, Ay, Het, —C(O)R$^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —OR$^7$, —OAy, —OHet, —NR$^7R^8$, —NR$^7$Ay, —NHHet, —S(O)$_nR^9$, —S(O)$_n$Ay, —S(O)$_n$Het, —S(O)$_2$NR$^7R^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7R^8$, —R$^{10}$NR$^7$Ay, —R$^{10}$NHSO$_2R^9$, —R$^{10}$C(O)R$^9$, —R$^{10}$C(O)Ay, —R$^{10}$C(O)Het, —R$^{10}$CO$_2R^9$, —R$^{10}$OC(O)R$^9$, —R$^{10}$OC(O)Ay, —R$^{10}$OC(O)Het, —R$^{10}$C(O)NR$^9R^{11}$, —R$^{10}$C(O)NR$^7$Ay, —R$^{10}$C(O)NHR$^{10}$Het, —R$^{10}$C(S)NR$^9R^{11}$, —R$^{10}$C(NH)NR$^9R^{11}$, —R$^{10}$SO$_2R^9$, —R$^{10}$SO$_2$NR$^9R^{11}$, —R$^{10}$SO$_2$NHCOR$^9$, —R$^{10}$OS(O)$_nR^9$, cyano, nitro and azido;

or when p is 2, two adjacent $R^6$ groups together with the carbon atoms to which they are bonded form a cycloalkyl or a 5- or 6-membered heterocyclic group containing 1 or 2 heteroatoms;

Y is N or CH;

$R^2$ is selected from the group consisting of halo, alkyl, cycloalkyl, alkenyl, cycloalkenyl, Ay, Het, —OR$^7$, —OAy, —OHet —NR$^7R^8$, —NR$^7$Ay, —NHHet —S(O)$_nR^9$, —S(O)$_n$Ay, —R$^{10}$NR$^7R^8$ and —R$^{10}$NR$^7$Ay;

$R^3$ and $R^4$ are the same or different and are each independently selected from the group consisting of H, halo, alkyl, alkenyl, cycloalkenyl, Ay, Het, —C(O)R$^7$, C(O)Ay, —CO$_2R^7$, —CO$_2$Ay, —OR$^7$, —OAy, —NR$^7R^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7R^8$ and —R$^{10}$NR$^7$Ay;

Ring A is selected from the group consisting of aryl, 5–10 membered heterocyclic group and a 5–10 membered heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8{}_1$, —C(NH)NR$^7$Ay, —OR$^7$, —OAy, —OHet, —NR$^7R^8$, —NR$^7$Ay, —NHHet, —S(O)$_nR^9$, —S(O)$_2$NR$^7R^8$, —S(O)$_2$NR$^7$Ay, —R$^{10}$cycloalkyl, —R$^{10}$Het, —R$^{10}$C(O)R$^9$, —R$^{10}$CO$_2R^9$, —R$^{10}$C(O)NR$^9R^{11}$, —R$^{10}$C(O)NR$^7$Ay, —R$^{10}$C(O)NHR$^{10}$Het, —R$^{10}$C(S)NR$^9R^{11}$, —R$^{10}$C(NH)NR$^9R^{11}$, —R$^{10}$OR$^9$, —R$^{10}$NR$^7R^8$, —R$^{10}$NR$^7$Ay, —R$^{10}$SO$_2R^9$, —R$^{10}$SO$_2$NR$^9R^{11}$, —R$^{10}$SO$_2$NHCOR$^9$, cyano, nitro and azido; and pharmaceutically acceptable salts, solvates and physiologically functional derivatives thereof.

According to another aspect, the present invention provides a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir and valaciclovir.

According to a third aspect, the present invention provides a method for the prophylaxis or treatment of a herpes viral infection in an animal. The method comprises administering to the animal a therapeutically effective amount of a compound of formula (I) or a pharmaceutically acceptable salt, solvate or physiologically functional derivative thereof. The herpes viral infection may be herpes simplex virus 1, herpes simplex virus 2, cytomegalovirus, Epstein Barr virus, varicella zoster virus, human herpes virus 6, human herpes virus 7, or human herpes virus 8.

According to a fourth aspect, the present invention provides a method for the prophylaxis or treatment of a condition or disease associated with a herpes viral infection in an animal. The method comprises administering to the animal a therapeutically effective amount of the compound of formula (I) or a pharmaceutically acceptable salt, solvate or physiologically functional derivative thereof.

According to a fifth aspect, the present invention provides a process for preparing a compound of formula (I) wherein $Y^1$ is CH; Y is N; $R^2$ is selected from the group consisting of alkyl, cycloalkyl, alkenyl, cycloalkenyl, Ay, Het, —OR$^7$, —OAy, —OHet —NR$^7R^8$, —NR$^7$Ay, —NHHet —S(O)$_nR^9{}_1$, —S(O)$_n$Ay, —R$^{10}$NR$^7R^8$ and —R$^{10}$NR$^7$Ay; and $R^3$ and $R^4$ are H. The process comprises reacting a compound of formula (XX):

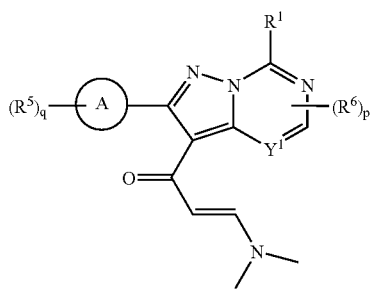

with a compound of formula (XXI):

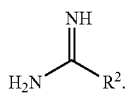

According to a sixth aspect, the present invention provides a process for preparing a compound of formula (I) wherein Y is N; $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NHHet —$S(O)_nR^9$, —$S(O)_n$Ay, —$R^{10}NR^7R^8$ and —$R^{10}NR^7$Ay; $R^3$ is selected from the group consisting of H, alkyl, alkenyl, cycloalkyl, Ay, Het, —$C(O)R^7$, $C(O)$Ay, —$CO_2R^7$, —$CO_2$Ay, —$OR^7$, —OAy, —$NR^7R^8$ (where $R^7$ and $R^8$ are not H), —$NR^7$Ay (where $R^7$ is H), —$SO_2NHR^9$, —$R^{10}OR^7$, —$R^{10}$cycloalkyl, —$R^{10}$OAy, —$R^{10}NR^7R^8$ and —$R^{10}NR^7$Ay; and $R^4$ is H. The process comprises reacting a compound of formula (XXV):

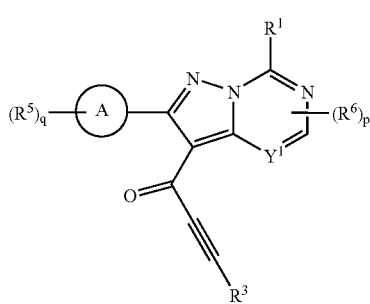

with a compound of formula (XXI):

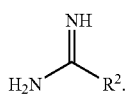

According to a seventh aspect, the present invention provides a process for preparing a compound of formula (I) wherein Y is N and $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NHHet —$S(O)_nR^9$, —$S(O)_n$Ay, —$R^{10}NR^7R^8$ and —$R^{10}NR^7$Ay. The process comprises the steps of:

a) reacting a compound of formula (XXVIII):

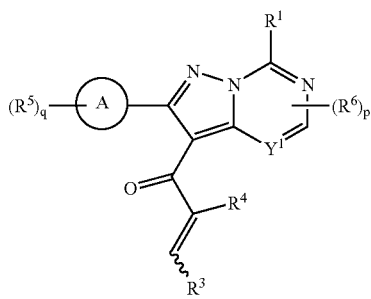

with a compound of formula (XXI):

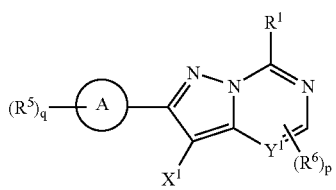

to prepare an intermediate compound; and
b) oxidizing the intermediate compound.

According to an eighth aspect, the present invention provides a process for preparing a compound of formula (I). The process comprises reacting a compound of formula (XXX):

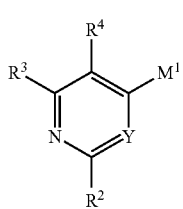

wherein $X^1$ is chloro, bromo or iodo;

with a compound of formula (X):

X $$\begin{array}{c} R^4 \\ R^3 \diagdown \diagup M^1 \\ | \quad | \\ N \quad Y \\ \diagdown \diagup \\ R^2 \end{array}$$

wherein $M^1$ is —$B(OH)_2$, —$B(ORa)_2$, —$B(Ra)_2$, —Sn$(Ra)_3$, Zn-halide, ZnRa, or Mg-halide where Ra is alkyl or cycloalkyl and halide is halo.

As another aspect, the present invention provides a process comprising the further step of converting the compound of formula (I) to a pharmaceutically acceptable salt, solvate or physiologically functional derivative thereof. In another aspect, the present invention provides a process comprising the further step of converting the compound of formula (I) or a pharmaceutically acceptable salt, solvate or physiologically functional derivative thereof to another compound of formula (I) or a pharmaceutically acceptable salt, solvate or physiologically functional derivative thereof.

According to another aspect, the present invention provides a radiolabeled compound of formula (I) or a pharmaceutically acceptable salt, solvate or physiologically functional derivative thereof. In one embodiment, the radiolabeled compound is tritiated. In another aspect, the present invention provides a biotinylated compound of formula (I) or a pharmaceutically acceptable salt, solvate or physiologically functional derivative thereof.

According to another aspect, the present invention provides a compound of formula (I) for use in therapy. The present invention also provides a compound of formula (I) for the prophylaxis or treatment of a herpes viral infection in an animal. The present invention also provides a compound of formula (I) for the prophylaxis or treatment of a condition or disease associated with a herpes viral infection in an animal.

According to another aspect, the present invention provides the use of a compound of formula (I) for the preparation of a medicament for prophylaxis or treatment of a herpes viral infection in an animal, preferably humans. The present invention also provides the use of a compound of formula (I) for the preparation of a medicament for the prophylaxis or treatment of a condition or disease associated with a herpes viral infection in an animal, preferably humans.

According to another aspect, the present invention provides a pharmaceutical composition comprising a compound of formula (I) for use in the prophylaxis or treatment of herpes viral infections in an animal.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (IX), (XII), (XX), (XXV), (XXVIII) and (XXX), the phrase "a compound of formula (number)" means a compound having that formula and pharmaceutically acceptable salts, solvates and physiologically functional derivatives thereof.

As used herein, the terms "alkyl" (or "alkylene") refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted with one or more substituents selected from the group consisting of mercapto, nitro, cyano, azido and halo. Perhaloalkyl, such as trifluoromethyl, is one preferred alkyl group.

As used herein, the term "cycloalkyl" (or "cycloalkylene") refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on an available carbon with one or more substituents selected from the group consisting of mercapto, nitro, cyano, halo, and alkyl.

As used herein, the term "alkenyl" (or "alkenylene") refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on an available carbon with one or more substituents selected from the group consisting of mercapto, nitro, cyano, halo, and alkyl.

As used herein, the term "cycloalkenyl" (or "cycloalkenylene") refers to refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on an available carbon with one or more substituents selected from the group consisting of mercapto, nitro, cyano, halo, and alkyl.

As used herein, the term "alkynyl" (or "alkynylene") refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be be substituted on an available carbon with one or more substituents selected from the group consisting of mercapto, nitro, cyano, halo, and alkyl.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl and naphthyl. "Aryl" also includes substituted aryl. Aryl groups may optionally be substituted on an available carbon with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred aryl groups according to the invention include but are not limited to phenyl and substituted phenyl.

The term "heterocyclic" (or "heterocycle") refers to a monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic group may be optionally substituted on an available carbon or heteroatom, with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heterocyclic groups according to the invention include but are not limited to pyrrolidine, piperidine, morpholine, thiomorpholine and piperazine and substituted variants thereof.

The term "heteroaryl" refers to aromatic monocyclic groups and aromatic fused bicyclic groups having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl group may optionally be substituted on an available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Preferred heteroaryl groups according to the invention include but are not limited to pyridine, furan, thiophene, pyrrole, imidazole, pyrazole and pyrimidine, and substituted variants thereof.

The term "members" or "membered" in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) which occur and events that do not occur.

The present invention provides compounds of formula (I):

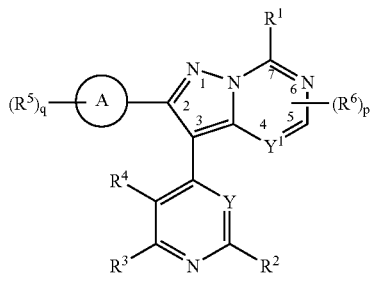

I wherein:

$R^1$ is selected from the group consisting of H, halo, alkyl, alkenyl, alkynyl, cycloalkyl, cycloalkenyl, Ay, Het, —C(O)$R^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —OR$^7$, —OAy, —OHet, —NR$^7R^8$, —NR$^7$Ay, —NHHet, —S(O)$_nR^9$, —S(O)$_n$Ay, —S(O)$_n$Het, —S(O)$_2$NR$^7R^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7R^8$, —R$^{10}$NR$^7$Ay, —R$^{10}$NHSO$_2R^9$, —R$^{10}$C(O)R$^9$, —R$^{10}$C(O)Ay, —R$^{10}$C(O)Het, —R$^{10}$CO$_2R^9$, —R$^{10}$OC(O)R$^9$, —R$^{10}$OC(O)Ay, —R$^{10}$OC(O)Het, —R$^{10}$C(O)NR$^9R^{11}$, —R$^{10}$C(S)NR$^9R^{11}$, —R$^{10}$C(NH)NR$^9R^{11}$, —R$^{10}$SO$_2R^9$, —R$^{10}$SO$_2$NR$^9R^{11}$, —R$^{10}$SO$_2$NHCOR$^9$, —R$^{10}$OS(O)$_nR^9$, cyano, nitro and azido;

each $R^7$ and $R^8$ are the same or different and are independently selected from the group consisting of H, alkyl, cycloalkyl, alkenyl, cycloalkenyl, —C(O)R$^9$, —CO$_2R^9$, —C(O)NR$^9R^{11}$, —C(S)NR$^9R^{11}$, —C(NH)N R$^9R^{11}$, —SO$_2R^{10}$, —SO$_2$NR$^9R^{11}$, —R$^{10}$cycloalkyl, —R$^{10}$Ay, —R$^{10}$Het, —R$^{10}$C(O)R$^9$, —R$^{10}$CO$_2R^9$, —R$^{10}$C(O)NR$^9R^{11}$, —R$^{10}$C(S)NR$^9R^{11}$, —R$^{10}$OR$^9$, —R$^{10}$NR$^9R^{11}$, —R$^{10}$NHCOR$^9$, —R$^{10}$NHC(NH)NR$^9R^{11}$, —R$^{10}$C(NH)NR$^9R^{11}$, —R$^{10}$NHSO$_2R^9$, —R$^{10}$SO$_2$NR$^9R^{11}$, —R$^{10}$SO$_2R^{10}$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1–10, and —R$^{10}$NR$^{10}R^{10}$;

each $R^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

$Y^1$ is N or CH;

p is 0, 1 or 2 when $Y^1$ is CH, p is 0 or 1 when $Y^1$ is N;

each $R^6$ is the same or different and is independently selected from the group consisting of H, halo, alkyl, alkenyl, alkynyl, cycloalkyl, cycloalkenyl, Ay, Het, —C(O)R$^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —OR$^7$, —OAy, —OHet, —NR$^7R^8$, —NR$^7$Ay, —NHHet, —S(O)$_nR^9$, —S(O)$_n$Ay, —S(O)$_n$Het, —S(O)$_2$NR$^7R^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7R^8$, —R$^{10}$NR$^7$Ay, —R$^{10}$NHSO$_2R^9$, —R$^{10}$C(O)R$^9$, —R$^{10}$C(O)Ay, —R$^{10}$C(O)Het, —R$^{10}$CO$_2R^9$, —R$^{10}$OC(O)R$^9$, —R$^{10}$OC(O)Ay, —R$^{10}$OC(O)Het, —R$^{10}$C(O)NR$^9R^{11}$, —R$^{10}$C(O)NR$^7$Ay, —R$^{10}$C(O)NHR$^{10}$Het, —R$^{10}$C(S)NR$^9R^{11}$, —R$^{10}$C(NH)NR$^9R^{11}$, —R$^{10}$SO$_2R^9$, —R$^{10}$SO$_2$NR$^9R^{11}$, —R$^{10}$SO$_2$NHCOR$^9$, —R$^{10}$OS(O)$_nR^9$, cyano, nitro and azido;

or when p is 2 (and Y' is CH), two adjacent $R^6$ groups together with the carbon atoms to which they are bonded form a cycloalkyl or a 5- or 6-membered heterocyclic group containing 1 or 2 heteroatoms;

Y is N or CH;

$R^2$ is selected from the group consisting of halo, alkyl, cycloalkyl, alkenyl, cycloalkenyl, Ay, Het, —OR$^7$, —OAy, —OHet —NR$^7R^8$, —NR$^7$Ay, —NHHet —S(O)$_nR^9$, —S(O)$_n$Ay, —R$^{10}$NR$^7R^8$ and —R$^{10}$NR$^7$Ay;

$R^3$ and $R^4$ are the same or different and are each independently selected from the group consisting of H, halo, alkyl, alkenyl, cycloalkyl, Ay, Het, —C(O)R$^7$, C(O)Ay, —CO$_2R^7_1$, —CO$_2$Ay, —OR$^7$, —OAy, —NR$^7R^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7R^8$ and —R$^{10}$NR$^7$Ay;

Ring A is selected from the group consisting of aryl, 5–10 membered heterocyclic group and a 5–10 membered heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —OR$^7$, —OAy, —OHet, —NR$^7R^8$, —NR$^7$Ay, —NHHet, —S(O)$_nR^9$, —S(O)$_2$NR$^7R^8$, —S(O)$_2$NR$^7$Ay, —R$^{10}$cycloalkyl, —R$^{10}$Het, —R$^{10}$C(O)R$^9$, —R$^{10}$CO$_2R^9$, —R$^{10}$C(O)NR$^9R^{11}$, —R$^{10}$C(O)NR$^7$Ay, —R$^{10}$C(O)

NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido; and pharmaceutically acceptable salts, solvates and physiologically functional derivatives thereof.

In one embodiment of the invention R$^1$ contains an aryl, heterocyclic or heteroaryl moiety (e.g., R$^1$ is selected from the group consisting of Ay, Het, —C(O)Ay, —C(O)Het, —C(O)NR$^7$R$^8$, —C(O)NR$^7$Ay, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$Ay, —S(O)$_n$Het, —S(O)$_2$NR$^7$R$^8$, —S(O)$_2$NR$^7$Ay, —R$^{10}$Ay, —R$^{10}$Het, —R$^{10}$NR$^7$R$^8$, —R$^{10}$NR$^7$Ay, —R$^{10}$C(O)Ay, —R$^{10}$C(O)Het, —R$^{10}$OC(O) Ay, —R$^{10}$OC(O)Het, —R$^{10}$C(O)NR$^7$Ay, —R$^{10}$C(O) NHR$^{10}$Het (where R$^7$ or R$^8$ is appropriately defined to provide a group containing an aryl, heterocyclic or heteroaryl moiety), or any subset thereof). In another embodiment, compounds of formula (I) are defined wherein R$^1$ contains a heterocyclic or heteroaryl moiety (e.g., R$^1$ is selected from the group consisting of Het, —C(O)Het, —C(O)NR$^7$R$^8$, —C(O)NR$^7$Ay, —C(NH)NR$^7$R$^8$, —OR$^7$, —OHet, —NR$^7$R$^8$, —NHHet, —S(O)$_n$Het, —S(O)$_2$NR$^7$R$^8$, —R$^{10}$Het, —R$^{10}$NR$^7$R$^8$, —R$^{10}$C(O)Het, —R$^{10}$OC(O)Het and —R$^{10}$C(O)NHR$^{10}$Het (where R$^7$ or R$^8$ is appropriately defined to provide a group containing a heterocyclic or heteroaryl moiety), or any subset thereof). In yet another embodiment, the compounds of formula (I) are defined wherein R$^1$ does not contain an aryl, heterocyclic or heteroaryl moiety (e.g., R$^1$ is selected from the group consisting of H, halo, alkyl, alkenyl, alkynyl, cycloalkyl, cycloalkenyl, —C(O)R$^9$, —CO$_2$R$^9$, —C(O)NR$^7$R$^8$, —C(S)NR$^9$R$^{11}$, —C(NH)NR$^7$R$^8$, —OR$^7$, —NR$^7$R$^8$, —S(O)$_n$R$^9$, —S(O)$_2$NR$^7$R$^8$, —R$^{10}$cycloalkyl, —R$^{10}$OR$^9$, —R$^{10}$NR$^7$R$^8$, —R$^{10}$NHSO$_2$R$^9$, —R$^{10}$C(O)R$^9$, —R$^{10}$CO$_2$R$^9$, —R$^{10}$OC(O)R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido (where R$^7$ and R$^8$ are appropriately defined to provide a group that does not contain an aryl, heterocyclic or heteroaryl moiety), or any subset thereof). In another embodiment, R$^1$ may contain an aryl moiety but does not contain a heteroaryl or heterocyclic moiety (e.g., R$^1$ is selected from the group consisting of H, halo, alkyl, alkenyl, alkynyl, cycloalkyl, cycloalkenyl, Ay, —C(O)R$^9$, —C(O)Ay, —CO$_2$R$^9$, —C(O)NR$^7$R$^8$, —C(O)NR$^7$Ay, —C(S) NR$^9$R$^{11}$, —C(NH)NR$^7$R$^8$, —C(NH)NR$^7$Ay, —OR$^7$, —OAy, —NR$^7$R$^8$, —NR$^7$Ay, —S(O)$_n$R$^9$, —S(O)$_n$Ay, —S(O)$_2$NR$^7$R$^8$, —S(O)$_2$NR$^7$Ay, —R$^{10}$cycloalkyl, —R$^{10}$Ay, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$CO$_2$R$^9$, —R$^{10}$OC(O)R$^9$, —R$^{10}$OC(O)Ay, —R$^{10}$C(O) NR$^9$R$^{11}$, —R$^{10}$C(O)NR$^7$Ay, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido (where R$^7$ and R$^8$ are appropriately defined to provide a group that does not contain a heterocyclic or heteroaryl moiety), or any subset thereof).

In one embodiment, R$^1$ is selected from the group consisting of halo, alkyl, cycloalkyl, Ay, Het, —OR$^7$, —OAy, —NR$^7$R$^8$, —NR$^7$Ay, —NHHet, —S(O)$_n$R$^9$, —R$^{10}$cycloalkyl, —R$^{10}$OR$^9$, —R$^{10}$NR$^7$R$^8$ and —R$^{10}$NR$^7$Ay, or any subset thereof. More particularly, R$^1$ is selected from the group consisting of halo, alkyl, Het, —OR$^7$, —NR$^7$R$^8$, —NR$^7$Ay, —NHHet and —S(O)$_n$R$^9$, or any subset thereof. In one particular embodiment R$^1$ is selected from the group consisting of alkyl, Het, —OR$^7$, —NR$^7$R$^8$, —NR$^7$Ay and —S(O)$_n$R$^9$, or any subset thereof. In one embodiment, R$^1$ is —NR$^7$R$^8$.

More specifically, particular compounds of formula (I) are defined wherein R$^1$ is selected from the group consisting of halo, alkyl, —NH$_2$, —NH-alkyl, —NH-cycloalkyl, —N(alkyl)(alkyl), Het, —O-alkyl, —NHalkyl—O—alkyl, —NHAy and —S-alkyl, or any subset thereof. More particularly, R$^1$ is selected from the group consisting of —NH-alkyl, —NH-cycloalkyl and pyrrolidine or any subset thereof. Specific examples of some R$^1$ groups are selected from the group consisting of Cl, ethyl, propyl, isopropyl, butyl, isobutyl, —NH-methyl, —N(CH$_3$)$_2$, —NH-cyclopentyl, —NH-cyclopropyl, —NH-isopropyl, —NH-butyl, —NH-phenyl, —NH(CH$_2$)$_2$OCH$_3$, methoxy, ethoxy, propoxy, isopropoxy, butoxy, thiomethoxy, thioethoxy, thioisopropoxy and pyrrolidine, or any subset thereof.

In one embodiment, R$^7$ and R$^8$ are each the same or different and are each independently selected from the group consisting of H, alkyl, cycloalkyl, —C(O)R$^9$, —R$^{10}$-cycloalkyl, —R$^{10}$Ay, —R$^{10}$Het, —R$^{10}$OR$^9$, —R$^{10}$NR$^9$R$^{11}$, and —R$^{10}$CO$_2$R$^9$, or any subset thereof. More particularly in such embodiment, R$^7$ and R$^8$ are each the same or different and are each independently selected from the group consisting of H, alkyl, cycloalkyl, —R$^{10}$-cycloalkyl, —R$^{10}$Ay and —R$^{10}$Het, or any subset thereof. In one particular embodiment, R$^7$ and R$^8$ are each the same or different and are each independently selected from the group consisting of H, alkyl and cycloalkyl.

In the definition of R$^9$ and R$^{11}$, "—R$^{10}$(OR$^{10}$)$_w$" refers to a PEG-like chain.

In one embodiment R$^9$ and R$^{11}$ are each the same or different and are each independently selected from the group consisting of H, alkyl, cycloalkyl, and —R$^{10}$-cycloalkyl, or any subset thereof. More particularly, R$^9$ and R$^{11}$ are each the same or different and are each independently selected from the group consisting of H and alkyl.

In one embodiment, R$^{10}$ is alkyl or cycloalkyl; more particularly alkyl.

In one class of compounds of formula (I), Y$^1$ is CH. In another embodiment, the compounds of formula (I) are defined wherein Y$^1$ is N.

When Y$^1$ is CH. p is 0, 1 or 2 and R$^6$ may be bonded through Y$^1$. When Y$^1$ is N, p is 0 or 1 and R$^6$ may not be bonded through Y$^1$. In one embodiment, p is 0 or 1. In one particular embodiment, p is 0.

Compounds of formula (I) include those compounds defined wherein R$^6$ contains an aryl, heterocyclic or heteroaryl moiety. In one embodiment, compounds of the present invention include those compounds defined wherein R$^6$ contains a heterocyclic or heteroaryl moiety. Another class of compounds of formula (I) includes those compounds defined wherein R$^6$ does not contain an aryl, heterocyclic or heteroaryl moiety. Yet another class of compounds include those defined wherein R$^6$ does not contain a heterocyclic or heteroaryl moiety but may contain an aryl moiety. Based on the guidance given above for R$^1$, one skilled in the art can readily determine the list of appropriate groups defining R$^6$ which contain or exclude aryl, heterocyclic or heteroaryl moeities.

When Y$^1$ is CH and p is 2, the two adjacent R$^6$ groups (i.e., R$^6$ bonded at C-4 and R$^6$ bonded at C-5) together with the atoms to which they are bonded may optionally form a C$_{5-6}$ cycloalkyl or a 5- or 6- membered heterocyclic group containing 1 or 2 heteroatoms. By "two adjacent R$^6$ groups" is meant that two R$^6$ groups are bonded to adjacent carbon atoms (C-4 and C-5). In the embodiments where two adjacent $R^6$ groups together with the atoms to which they are bonded form a $C_{5-6}$ cycloalkyl or a 5- or 6-membered heterocyclic group containing 1 or 2 heteroatoms, each $R^6$ group may be the same or different and is preferrably selected from the group consisting of alkyl, alkenyl, —$OR^7$, —$NR^7R^8$ and —$S(O)_nR^9$. For example, in one embodiment two adjacent $R^6$ groups are —$OR^7$ and together with the atoms to which they are bonded, they form a heterocyclic group such as:

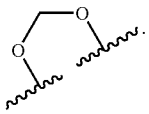

In another embodiment, two adjacent $R^6$ groups are alkyl and together with the atoms to which they are bonded, they form a cycloalkyl group such as:

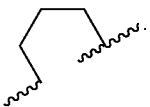

In another embodiment two adjacent $R^6$ groups are defined as —$OR^7$ and —$NR^7R^8$ respectively and together with the atoms to which they are bonded, they form a heterocyclic group such as:

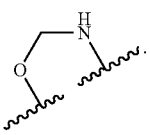

From these examples, additional embodiments can be readily ascertained by those skilled in the art Preferably the compounds of formula (I) are defined wherein when p is 2, two adjacent $R^6$ groups together with the atoms to which they are bonded do not form a $C_{5-6}$ cycloalkyl or a 5- or-6-membered heterocyclic group containing 1 or 2 heteroatoms.

In one embodiment, $R^6$ is the same or different and is independently selected from the group consisting of halo, alkyl, Ay, Het, —C(O)Het, —$CO_2R^9$, —C(O)$NR^7R^8$, —C(O)$NR^7$Ay, —$OR^7$, —OAy, —$NR^7R^8$, —$NR^7$Ay, —NHHet, —$S(O)_nR^9$, —$S(O)_n$Ay, —$S(O)_n$Het, —$R^{10}OR^9$ and cyano. More particularly, each $R^6$ is the same or different and is independently selected from the group consisting of halo, alkyl, Het, —$OR^{7'}$, —$NR^7R^8$, —NHHet, —$S(O)_n$ $R^9$, and cyano, or any subset thereof. In one embodiment each $R^6$ is the same or different and is independently selected from the group consisting of halo, alkyl. Het, —$NR^7R^8$, —NHHet and and —$S(O)_nR^9$.

More specific examples of particular $R^6$ groups include but are not limited to —$NH_2$, —NHalkyl, —$NHR^{10}OR^9$, —NH-cycloalkyl, and —$S(O)_n$alkyl. In one embodiment, $R^6$ is selected from the group consisting of —O—butyl, —$NH_2$, —NHCH$(CH_3)_2$, —NH-cyclopropyl, —NH-n-propyl, —NH-n-butyl, —NH-cyclopentyl, —NH-cyclohexyl, —NH$(CH_2)_2$—O—$CH_3$, —S-methyl and —S-ethyl.

In one embodiment, compounds of formula (I) are defined wherein, Y is CH. In another embodiment, the compounds of formula (I) are defined wherein Y is N.

Compounds of formula (I) include those compounds defined wherein $R^2$ contains an aryl, heterocyclic or heteroaryl moiety. In one embodiment, compounds of the present invention include those compounds defined wherein $R^2$ contains a heterocyclic or heteroaryl moiety. Another class of compounds of formula (I) includes those compounds defined wherein $R^2$ does not contain an aryl, heterocyclic or heteroaryl moiety. Yet another class of compounds include those defined wherein $R^2$ does not contain a heterocyclic or heteroaryl moiety but may contain an aryl moiety. Based on the guidance given above for $R^1$, one skilled in the art can readily determine the list of appropriate groups defining $R^2$ which contain or exclude aryl, heterocyclic or heteroaryl moeities.

In one embodiment, $R^2$ is selected from the group consisting of Ay, Het, —$OR^7$, —OAy, —OHet, —$NR^7R^8$, —$NR^7$Ay, —NHHet, —$S(O)_nR^9$, —$S(O)_n$Ay, —$R^{10}NR^7R^8$ and —$R^{10}NR^7$Ay, or any subset thereof. More particularly, $R^2$ is selected from the group consisting of Het, —$NR^7R^8{}_1$, —$NR^7$Ay, —NHHet, —$R^{10}NR^7R^8$ and —$R^{10}NR^7$Ay, or any subset thereof. Particular compounds of formula (I) are defined where $R^2$ is selected from the group consisting of Het, —$NR^7R^8$, —$NR^7$Ay and —NHHet, or any subset thereof. In one embodiment, $R^2$ is selected from the group consisting of —$NR^7R^8$9, —$NR^7$Ay and —NHHet, or any subset thereof. In another embodiment, $R^2$ is —$NR^7R^8$ or —NHHet. In one particular embodiment, $R^2$ is —$NR^7R^8$. In one embodiment, $R^2$ is not —$NR^7$Ay, more specifically, $R^2$ is not NH-phenyl.

More specifically, in one embodiment, $R^2$ is selected from the group consisting of —$NH_2$, —NH-alkyl, —NH-cycloalkyl, —N(alkyl)(alkyl), —NH-phenyl, —N(alkyl)-phenyl, Het (e.g., pyrrolidine), —NHHet and —NH-alkyl-Het, or any subset thereof. More particularly, $R^2$ is selected from the group consisting of —NH-alkyl, —NH-cycloalkyl and —NH-phenyl, or any subset thereof. In one embodiment, $R^2$ is —NH-alkyl or —NH-cycloalkyl.

Specific examples of some particular $R^2$ groups are selected from the group consisting of —$NH_2$, —NH-methyl, —NH-ethyl, —N H-propyl, —NH-isopropyl, —NH-cyclopropyl, —NH-butyl, —NH-isobutyl, —NH-cyclopentyl, —NH-cyclohexyl, —NH$(CH_2)_2OCH_3$, —NH-phenyl, —N(methyl)-phenyl, and pyrrolidine (e.g., pyrrolidine bonded through N). In one embodiment, $R^2$ is selected from the group consisting of —$NH_2$, —NH-methyl, —NH-ethyl, —NH-propyl, —NH-isopropyl, —NH-cyclopropyl, —NH-butyl, —NH-isobutyl, —NH-cyclopentyl, —NH-cyclohexyl, —NH$(CH_2)_2OCH_3$ and pyrrolidine (e.g., pyrrolidine bonded through N).

In another embodiment, the compounds of formula (I) include those compounds defined where at least one of $R^3$ and $R^4$ contain a heterocyclic or heteroaryl moiety. Another embodiment includes those compounds of formula (I) where neither $R^3$ nor $R^4$ contain a heterocyclic or heteroaryl moiety. Based on the guidance given above for $R^1$, one skilled in the art can readily determine the list of appropriate groups defining $R^3$ and $R^4$ which contain or exclude aryl, heterocyclic or heteroaryl moeities.

In one embodiment, $R^3$ is preferably selected from the group consisting of H, halo, alkyl, Ay, —$CO_2R^7$, —$OR^7$, —$NR^7R^8$, —$R^{10}OR^7$ and —$R^{10}NR^7R^8$, or any subset thereof. More particularly, $R^3$ is selected from the group consisting of H, halo, alkyl, —OR$^7$ and —NR$^7$R$^8{}_1$ or any subset thereof. In one embodiment, R$^3$ is H or alkyl. In one embodiment R$^3$ is H.

In one embodiment, R$^4$ is selected from the group consisting of H, halo, alkyl, Ay, —CO$_2$R$^7$, —OR$^7$, —NR$^7$R$^8$, —R$^{10}$OR$^7$ and —R$^{10}$NR$^7$R$^8$, or any subset thereof. More particularly R$^4$ is selected from the group consisting of H, halo, alkyl, OR$^7$ and —NR$^7$R$^8$, or any subset thereof. In one embodiment, R$^4$ is H or alkyl. In one embodiment, R$^4$ is H.

(A)

in formula (I) above is herein referred to as "Ring A."

Ring A is aryl, a 5–10 membered heterocyclic group or a 5–10 membered heteroaryl group (including 1, 2, 3 or 4 heteroatoms selected from N, O and S). Ring A may be bonded to the C-2 carbon of the fused ring through any available atom including any available heteroatom.

In one embodiment, Ring A is selected from the group consisting of aryl, a 5–6 membered heterocyclic or heteroaryl group and a 9-membered heterocyclic or heteroaryl group.

In one embodiment, Ring A is selected from the group consisting of phenyl, naphthyl, furan, pyridine, pyrimidine, thiazole, pyrazine, pyrrole, imidazole, oxazole, benzimidazole, quinoline, isoquinoline, and quinoxoline, or any subset thereof. More particularly, Ring A in formula (I) is selected from the group consisting of phenyl, furan, pyridine and pyrimidine. In one embodiment, Ring A contains at least one N atom and is bonded through N. In another embodiment, Ring A is phenyl.

In one embodiment, q is 0, 1 or 2. In one particular embodiment, q is 0. In one embodiment q is 1.

R$^5$ may be bonded to any available carbon or heteroatom of Ring A. Compounds of formula (I) include those compounds defined wherein R$^5$ contains an aryl, heterocyclic or heteroaryl moiety. In one embodiment, compounds of the present invention include those compounds defined wherein R$^5$ contains a heterocyclic or heteroaryl moiety. Another class of compounds of formula (I) includes those compounds defined wherein R$^5$ does not contain an aryl, heterocyclic or heteroaryl moiety. Yet another class of compounds include those defined wherein R$^5$ does not contain a heterocyclic or heteroaryl moiety but may contain an aryl moiety. Based on the guidance given above for R$^1$, one skilled in the art can readily determine the list of appropriate groups defining R$^5$ which contain or exclude aryl, heterocyclic or heteroaryl moeities.

In one embodiment, each R$^5$ group is the same or different and is independently selected from the group consisting of halo, alkyl, alkenyl, Ay, Het, —CO$_2$R$^9$, —C(O)NR$^7$R$^8$, —C(O)NR$^7$Ay, —OR$^7$, —OAy, —NR$^7$R$^8$, —NR$^7$Ay, —S(O)$_2$NR$^7$R$^8$, cyano, nitro and azido, or any subset thereof. More particularly, each R$^5$ group is the same or different and is independently selected from the group consisting of halo, alkyl, alkenyl, —OR$^7$, —NR$^7$R$^8$, Ay, Het, cyano and azido, or any subset thereof. In one embodiment, each R$^5$ group is the same or different and is independently selected from the group consisting of halo, alkyl, —OR$^7$, —NR$^7$R$^8$ and cyano, or any subset thereof. In one embodiment, R$^5$ is halo, alkyl or OR$^7$.

In particular, specific embodiments of the compounds of formula (I) are defined where R$^5$ is halo (e.g., fluoro, chloro or bromo), alkyl (e.g., methyl), O-alkyl (e.g., O-methyl, O-isobutyl, and

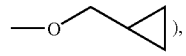

cyano, —NH—CH$_3$, and —N(CH$_3$)$_2$.

It is to be understood that the present invention includes all combinations and subsets of the particular and preferred groups defined hereinabove.

Specific compounds of formula (I) include but are not limited to:

N—Cyclopentyl-3-[2-(cyclopentylamino)pyrimidin-4yl]-2-(4-fluorophenyl)pyrazolo-[1,5-c]pyrimidin-7-amine;

N—Cyclopentyl-3-[2-(cyclopropylamino)pyrimidin-4yl]-2-(4fluorophenyl)pyrazolo-[1,5-c]pyrimidin-7-amine;

4-[2-(3-Chlorophenyl)pyrazolo[1,5-c]pyrimidin-3-yl]-N-cyclopentylpyrimidin-2-amine;

4-[2-(3-Chlorophenyl)-7-(methylthio)pyrazolo[1,5-c]pyrimidin-3-yl]-N-cyclopentylpyrimidin-2-amine;

2-(3-Chlorophenyl)-N-cyclopentyl-3-[2-(cyclopentylamino)-4-pyrimidinyl]pyrazolo[1,5-c]pyrimidin-7-amine;

4-[2-(3-Chlorophenyl)-7-(4-morpholinyl)pyrazolo[1,5-c]pyrimidin-3-yl]-N-cyclopentyl-2-pyrimidinamine;

2-(3-Chlorophenyl)-3-[2-(cyclopentylamino)-4-pyrimidinyl]-N-(2-methoxyethyl)pyrazolo[1,5-c]pyrimidin-7-amine;

2-(3-Chlorophenyl)-3-[2-(cyclopentylamino)-4-pyrimidinyl]pyrazolo[1,5-c]pyrimidin-7-ol;

N—Cyclopentyl-8-(2-fluoro-4-pyridinyl)-2-(methylsulfanyl)-7-phenyl pyrazolo[1,5-a][1,3,5]triazin-4amine;

N$^2$,N$^4$-Dicyclopentyl-8-[2-(cyclopentylamino)-4-pyridinyl]-7-phenylpyrazolo[1,5-a][1,3,5]triazine-2,4diamine; and N-Cyclopentyl-8-[2-(cyclopentylamino)-4-pyrimidinyl]-7-phenylpyrazolo[1,5-a][1,3,5]triazin-4-amine;

3-[2-(Butylamino)pyrimidin-4-yl]-N-cyclopentyl-2-(4-fluorophenyl)pyrazolo[1,5-c]pyrimidin-7-amine;

3-(2-Anilinopyrimidin-4-yl)-N-cyclopentyl-2-(4-fluorophenyl)pyrazolo[1,5-c]pyrimidin-7-amine;

3-[2-(1,3-Benzothiazol-2-ylamino)pyrimidin-4-yl]-N-cyclopentyl-2-(4-fluorophenyl)pyrazolo[1,5-c]pyrimidin-7-amine;

N-Cyclopentyl-2-(4-fluorophenyl)-3-{2-[[4-methyl-1,3-thiazol-2-yl)amino]pyrimidin-4yl}pyrazolo[1,5-c]pyrimidin-7-amine;

3-[2-(1H-Benzimidazol-2-ylamino)pyrimidin-4-yl]-N-cyclopentyl-2-(4-fluorophenyl)pyrazolo[1,5-c]pyrimidin-7-amine;

N-Cyclopentyl-3-{2-[[4-fluorobenzyl)amino]pyrimidin-4-yl}-2-(4-fluorophenyl)pyrazolo[1,5-c]pyrimidin-7-amine;

N-Cyclopentyl-2-(4-fluorophenyl)-3-{2-[(2-phenylethyl)amino]pyrimidin-4-yl}pyrazolo[1,5-c]pyrimidin-7-amine;

3-[2-(tert-Butylamino)pyrimidin-4-yl]-N-cyclopentyl-2-(4-fluorophenyl)pyrazolo[1,5-c]pyrimidin-7-amine;

N-Cyclopentyl-4-[2-(4-fluorophenyl)-7-(methylsulfanyl)pyrazolo[1,5- c]pyrimidin-3-yl]pyrimidin-2-amine;

N-Cyclopentyl-3-[2-(cyclopentylamino)pyrimidin-4-yl]-2-(4-methoxyphenyl)pyrazolo[1,5-c]pyrimidin-7-amine;

4-{7-(Cyclopentylamino)-3-[2-(cyclopentylamino)pyrimidin-4-yl]pyrazolo[1,5-c]pyrimidin-2-yl}phenol;

3-[2-(Cyclopentylamino)pyrimidin-4-yl]-N-cyclopropyl-2-(4methoxyphenyl)pyrazolo-[1,5-c]pyrimidin-7-amine;

2-(4-Butoxyphenyl)-N-cyclopentyl-3-[2-(cyclopentylamino)pyrimidin-4-yl]pyrazolo[1,5-c]pyrimidin-7-amine;

N-Cyclopentyl-3-[2-(cyclopentylamino)pyrimidin-4-yl]-2-(4-isobutoxyphenyl)pyrazolo[1,5-c]pyrimidin-7-amine;

N-Cyclopentyl-3-[2-(cyclopentylamino)pyrimidin-4-yl]-2-[4-(2-methoxyethoxy)phenyl]pyrazolo[1,5-c]pyrimidin-7-amine;

N-Cyclopentyl-3-[2-(cyclopentylamino)pyrimidin-4-yl]-2-(4-propoxyphenyl)pyrazolo[1,5-c]pyrimidin-7-amine;

N-(tert-Butyl)-3-[2-(cyclopentylamino)pyrimidin-4-yl]-2-(4-fluorophenyl)pyrazolo[1,5-c]pyrimidin-7-amine;

N-Cyclopentyl-4-[2-(4fluorophenyl)-7-pyrrolidin-1-ylpyrazolo[1,5-c]pyrimidin-3-yl]pyrimidin-2-amine; and N-Cyclopentyl-4-[2-(4-fluorophenyl)-7-piperidin-1-yl pyrazolo[1,5-c]pyrimidin-3-yl]pyrimidin-2-amine, or a pharmaceutically acceptable salt, solvate or physiologically functional derivative thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine-salts.

The term "solvate" as used herein refers to a complex of variable stoichiometry formed by a solute (a compound of formula (I)) and a solvent Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), Varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from RFA, viral infection, particularly by CMV and/or HHV-6 of the patient plays a pivotal role in the proliferation of the smooth muscle cells in the coronary vessel treated.

Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of conditions or diseases associated with hepatitis B or hepatitis C viruses, human papilloma virus (HPV) and HIV.

Thus, the present invention provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the prevention of infection, the prevention of occurrence of symptoms in an infected subject, the prevention of recurrence of symptoms in an infected subject, or a decrease in severity or frequency of symptoms of viral infection, condition or disease in the subject As used herein, the term "treatment" refers to the partial or total elimination of symptoms or decrease in severity of symptoms of viral infection, condition or disease in the subject, or the elimination or decrease of viral presence in the subject. As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome or multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome or multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the compound of formula (I) in the preparation of a medicament for the treatment of conditions or diseases associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents While it is possible that compounds of the present invention may be therapeutically administered as the raw chemical, it is preferable to present the active ingredient as a pharmaceutical formulation or composition. The pharmaceutical composition may comprise a pharmaceutically acceptable carrier or diluent. The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I). In one embodiment, the pharmaceutical composition further comprises one or more pharmaceutically acceptable carriers or diluents and optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules (including soft-gel capsules), cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the- active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described. Formulations for rectal administration may be presented as a suppository with the usual carriers such as cocoa butter, hard fat or polyethylene glycol.

Formulations suitable for topical (e.g., dermal) or intranasal application include ointments, creams, lotions, pastes, gels, sprays, aerosols and oils. Suitable carriers for such formulations include petroleum jelly, lanolin, polyethyleneglycols, alcohols and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, fameyclovir, gancyclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir and valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When a compound of formula (I) is used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations. When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein $Y^1$ is N; $R^1$ is selected from the group consisting of Het, —$OR^7$, —OAy, —OHet, —$NR^7R^8$, —$NR^7$Ay, —NHHet, —$S(O)_nR^9$, —$S(O)_n$Ay and —$S(O)_n$Het; p is 1 and $R^6$ is —$SR^9$, may be prepared by the process outlined in Scheme 1 below.

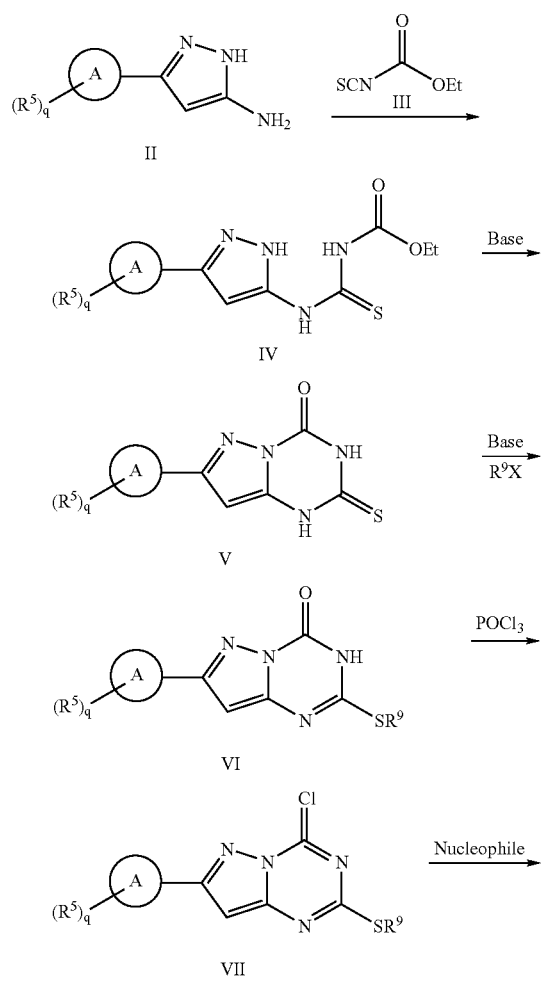

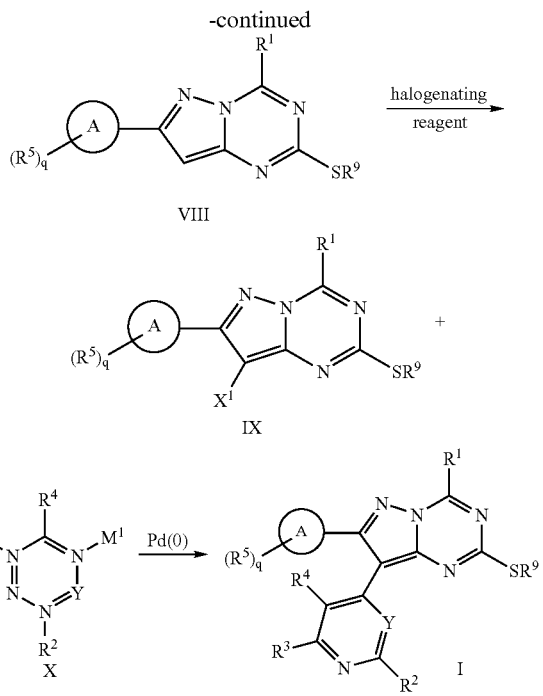

wherein:
$R^1$ is selected from the group consisting of Het, —$OR^7$, —OAy, —OHet, —$NR^7R^8$, —$NR^7$Ay, —NHHet, —$S(O)_nR^9$, —$S(O)_n$Ay and —$S(O)_n$Het;

each $R^7$ and $R^8$ are the same or different and are independently selected from the group consisting of H, alkyl, cycloalkyl, alkenyl, cycloalkenyl, —C(O)$R^9$, —$CO_2R^9$, —C(O)$NR^9R^{11}$, —C(S)$NR^9R^{11}$, —C(NH)$NR^9R^{11}$, —$SO_2R^{10}$, —$SO_2NR^9R^{11}$, —$R^{10}$cycloalkyl, —$R^{10}$Ay, —$R^{10}$Het, —$R^{10}$C(O)$R^9$, —$R^1CO_2R^9$, —$R^{10}$C(O)$NR^9R^{11}$, —$R^{10}$C(S)$NR^9R^{11}$, —$R^{10}OR^9$, —$R^{10}NR^9R^{11}$, —$R^{10}$NHCOR$^9$, —$R^{10}$NHC(NH)$NR^9R^{11}$, —$R^{10}$C(NH)$NR^9R^{11}$, —$R^{10}NHSO_2R^9$, —$R^{10}SO_2NR^9R^{11}$, —$R^{10}SO_2R^{10}$ and —$R^{10}SO_2NHCOR^9$;

each $R^9$ and $R^{11}$ are the same or different and are independently selected from the group consisting of H, alkyl, cycloalkyl, —$R^{10}$cycloalkyl, —$R^{10}$OH, —$R_{10}$(OR$^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl and alkynyl;

n is 0, 1 or 2;
Ay is aryl;
Het is a 5- or 6-membered heterocyclic or heteroaryl group;
$Y^1$ is N;
p is 1;
$R^6$ is —$SR^9$;
Y is N or CH;
$R^2$ is selected from the group consisting of halo, alkyl, cycloalkyl, alkenyl, cycloalkenyl, Ay, Het, —$OR^7_1$, —OAy, —OHet, —$NR^7R^8$, —$NR^7$Ay, —NHHet —$S(O)_nR^9$, —$S(O)_n$Ay, —$R^{10}NR^7R^8$ and —$R^{10}NR^7$Ay;

$R^3$ and $R^4$ are the same or different and are each independently selected from the group consisting of H, halo, alkyl, alkenyl, cycloalkyl, Ay, Het, —C(O)$R^7$, C(O)Ay, —$CO_2R^7$, —$CO_2$Ay, OR$^7$, —OAy, —$NR^7R^8$, —$NR^7$Ay, —NHHet, —SO$_2$NHR$^9$, —R$^{10}$OR$^7$, —R$^{10}$cycloalkyl, —R$^{10}$OAy, —R$^{10}$NR$^7$R$^8$ and —R$^{10}$NR$^7$Ay;

Ring A is selected from the group consisting of aryl, 5–10 membered heterocyclic group and a 5–10 membered heteroaryl group;

q is 0, 1, 2, 3, 4 or 5; and each R$^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O) Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_2$NR$^7$R$^8$, —S(O)$_2$NR$^7$Ay, —R$^{10}$cycloalkyl, —R$^{10}$Het, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido;

X is chloro, bromo or iodo;

X$^1$ is chloro, bromo, or iodo; and

M$^1$ is —B(OH)$_2$, —B(ORa)$_2$, —B(Ra)$_2$, —Sn(Ra)$_3$, Zn-halide, ZnRa, or Mg-halide where Ra is alkyl or cycloalkyl and halide is halo.

Generally, the process for preparing the compounds of formula (I) wherein Y$^1$ is N; R$^1$ is selected from the group consisting of Het, —OR$^7$, —OAy, —OHet, —NR$^7$R$^8$, —NR$^7$Ay, —NHHet, —S(O)$_n$R$^9$, —S(O)$_n$Ay and —S(O)$_n$Het; p is 1 and R$^6$ is —SR$^9$, (all formulas and all other variables having been defined above in connection with Scheme 1) comprises the steps of:

(a) reacting a compound of formula (II) with an isothiocyanate of formula (III) to prepare a compound of formula (IV);
(b) reacting the compound of formula (IV) with a base to prepare a compound of formula (V);
(c) reacting the compound of formula (V) with a base and an alkylating agent to prepare a compound of formula (VI);
(d) reacting a compound of formula (VI) with phosphorous oxychloride to prepare a compound of formula (VII);
(e) reacting a compound of formula (VII) with a heteroatom (N,O,S) nucleophile to prepare a compound of formula (VIII);
(f) halogenating a compound of formula (VIII) to prepare a compound of formula (IX); and
(g) reacting a compound of formula (IX) with a compound of formula (X) to prepare a compound of formula (I).

More specifically, compounds of formula (I) wherein Y$^1$ is N; R$^1$ is selected from the group consisting of Het, —OR$^7$, —OAy, —OHet, —NR$^7$R$^8$, —NR$^7$Ay, —NHHet, —S(O)$_n$R$^9$, —S(O)$_n$Ay and —S(O)$_n$Het; p is 1 and R$^6$ is —SR$^9$, can be prepared by reacting a compound of formula (IX) with a compound of formula (X).

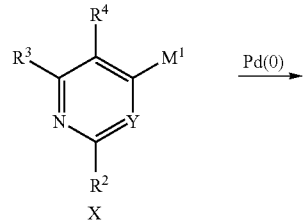

wherein all variables are as defined above in connection with Scheme 1.

The reaction may be carried out in an inert solvent, in the presence of a palladium (O) or nickel (O) catalyst. The reaction may optionally be heated to about 50–150° C. Typically the reaction is performed by reacting equimolar amounts of a compound of formula (IX) with a heteroaryl-metal compound of formula (X), but the reaction may also be performed in the presence of an excess of compound of the formula (X). The palladium or nickel catalyst is typically present in 1–10 mol % compared to the compound of formula (IX). Examples of suitable palladium catalysts include but are not limited to, tetrakis(triphenylphosphine) palladium (O), dichlorobis(triphenyl-phosphine)palladium (II), tris(dibenzylideneacetone)dipalladium (O), and bis (diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the heteroaryl-metal compound of formula (X) is an arylboronic acid or ester or an arylborinate the reaction is more conveniently carried out by adding a base in a proportion equivalent to, or greater than, that of the compound of formula (X). Heteroaryl-metal compounds of formula (X) may be obtained from commercial sources or prepared either as discreet isolated compounds or generated in situ using methods known to one skilled in the art. (Suzuki, A. *J. Organomet. Chem.* 1999, 576, 147; Stille, J. *Angew. Chem. Int. Ed. Engl.* 1986, 25, 508; Snieckus, V. *J. Org. Chem.* 1995, 60, 292.)

A compound of formula (IX) can be prepared from a compound of formula (VIII) by a halogenation procedure.

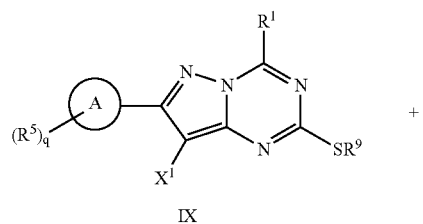

IX

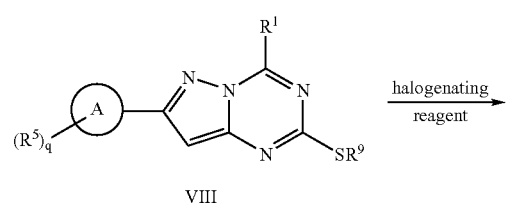

VIII

-continued

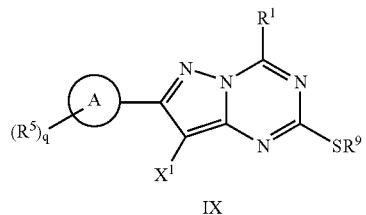

IX

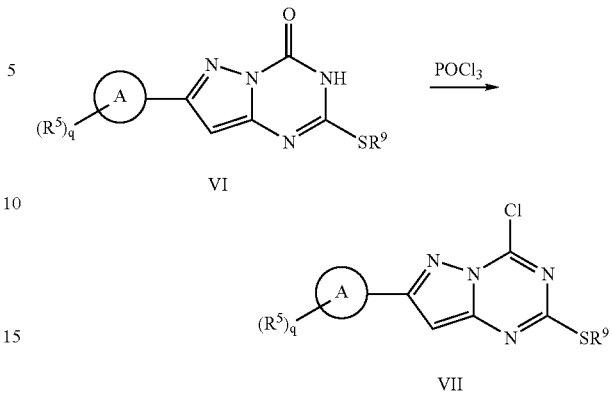

wherein all variables are as defined above in connection with Scheme 1.

Typically, the halogenation reaction is carried out by subjecting the compound of formula (VIII) to a halogenating reagent in a suitable solvent. Suitable halogenating reagents include but are not limited to, N-bromosuccinimide, trialkylammonium tribromides, bromine, N-chlorosuccinimide, N-iodosuccinimide, iodine, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

A compound of the formula (VIII) can be prepared from a compound of formula (VII) through reaction with a heteroatom (i.e., N, O or S) nucleophile selected from the group consisting of Het, —$OR^7$, —OAy, —OHet, —$NR^7R^8$, —$NR^7Ay$, —NHHet, —$S(O)_nR^9$, —$S(O)_nAy$ and —$S(O)_n$Het.

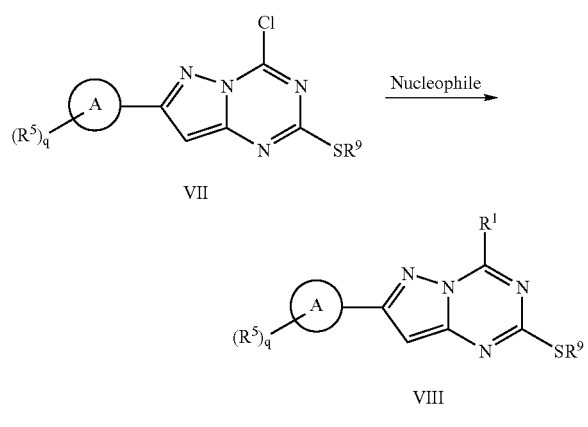

VIII wherein all variables are as defined above in connection with Scheme 1.

Typically the chloro compound of formula (VII) can be treated with the nucleophile in an inert solvent or the nucleophile when suitable can be used as the solvent. By way of example some suitable solvents include but are not limited to 1-methyl-2-pyrrolidinone, N,N-dimethylformamide, tetrahydrofuran, dimethyl sulfoxide, and the lower alcohols such as methanol, ethanol, isopropanol and the like. The reaction may be performed at or below ambient temperature or if deemed necessary the reaction may require heating to 50–200° C.

A compound of formula (VII) can be conveniently prepared from a compound of formula (VI) by treatment with phosphorous oxychloride.

wherein all variables are as defined above in connection with Scheme 1.

Conveniently, this type of transformation can be carried out using phosphorous oxychloride, optionally in the presence of a base. This is performed by treating a compound of formula (VI) with phosphorous oxychloride with optional heating. Typically an excess of the dehydrating reagent is used and the reaction can be heated up to reflux temperature of approximately 105° C. By way of example a suitable base is N,N-diethylaniline and the like.

A compound of the formula (VI) can be conveniently synthesized from a compound of formula (V) by an alkylation protocol.

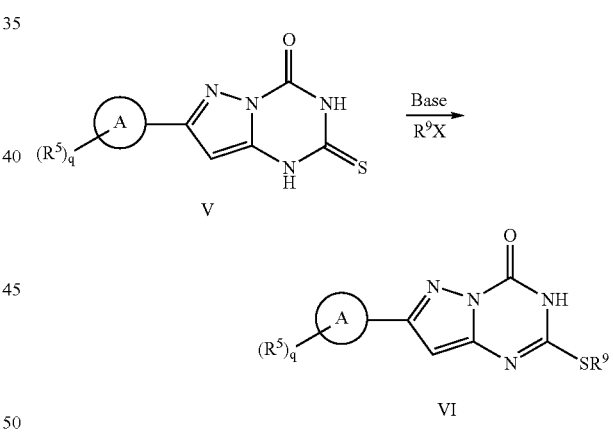

wherein all variables are as defined above in connection with Scheme 1.

This sequence can be carried out by reacting a compound of formula (V) with a base and an alkyl halide electrophile in an inert solvent at room temperature or optionally with heating. A typical base is aqueous sodium hydroxide or the like. Other bases can be used under anhydrous conditions such as potassium carbonate, sodium ethoxide, sodium hydride and the like. Electrophiles include but are not limited to alkyl halides such as methyl iodide ($R^9$=methyl) and alkyl sulfates such as dimethyl sulfate, and the like. A typical solvent system is ethanol/water, but other solvents, with or without an aqueous co-solvent, can be used, including 1-methyl-2-pyrrolidinone, N,N-dimethylformamide, tetrahydrofuran, dimethyl sulfoxide, and the lower alcohols such as methanol, ethanol, isopropanol, and the like. The reaction can optionally be heated to 50–200° C.

A compound of formula (V) can be prepared by an intramolecular condensation ring closing reaction of a compound of formula (IV).

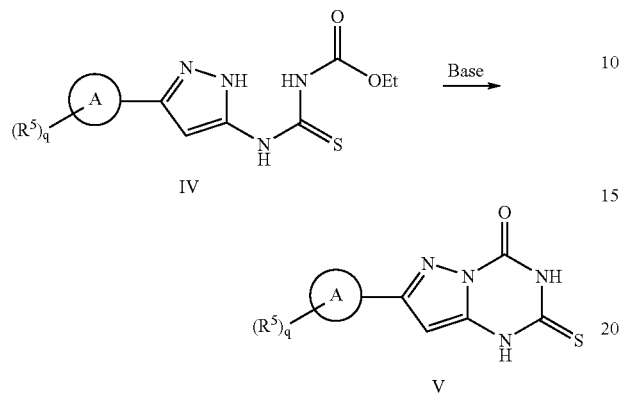

wherein all variables are as defined above in connection with Scheme 1.

This condensation can be typically carried out by treating a compound of formula (IV) with a base in an inert solvent. Typical bases include but are not limited to sodium hydroxide, sodium ethoxide, potassium carbonate, potassium tert-butoxide, and the like. Solvents include water, the lower alcohols such as ethanol, iospropanol, and the like. Additionally solvents can be chosen from 1-methyl-2-pyrrolidinone, N,N-dimethylformamide, tetrahydrofuran, dimethyl sulfoxide, and the like.

A compound of the formula (IV) can be conveniently formed by reaction of a compound of formula (II) with an isothiocyanate of formula (III).

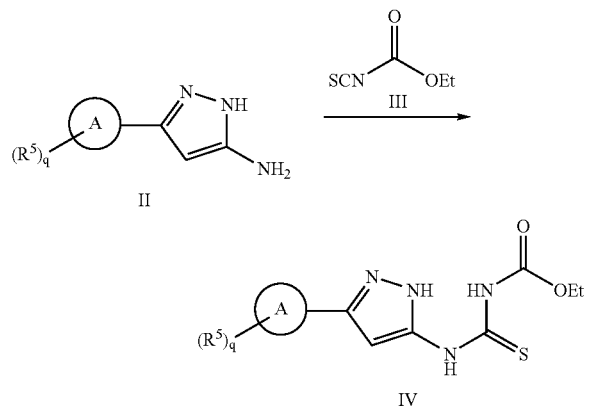

wherein all variables are as defined above in connection with Scheme 1.

This can be carried out by reacting a compound of formula (II) with a commercially available isothiocyanate such as ethoxycarbonyl isothiocyanate in a inert solvent optionally with heating. A suitable solvent includes but is not limited to toluene. The reaction may be heated to a temperature of from about 30–150° C.

Compounds of the formula (II) can be purchased from commercial sources or prepared using conventional techniques known to one skilled in the art.

In a further embodiment of the present invention, a compound of formula (I) wherein $Y^1$ is N; $R^1$ is selected from the group consisting of of Het, —$OR^7$, —OAy, —OHet, —$NR^7R^8$, —$NR^7Ay$ and —NHHet and p is 0, may be conveniently prepared by the process outlined in Scheme 2 below.

Scheme 2

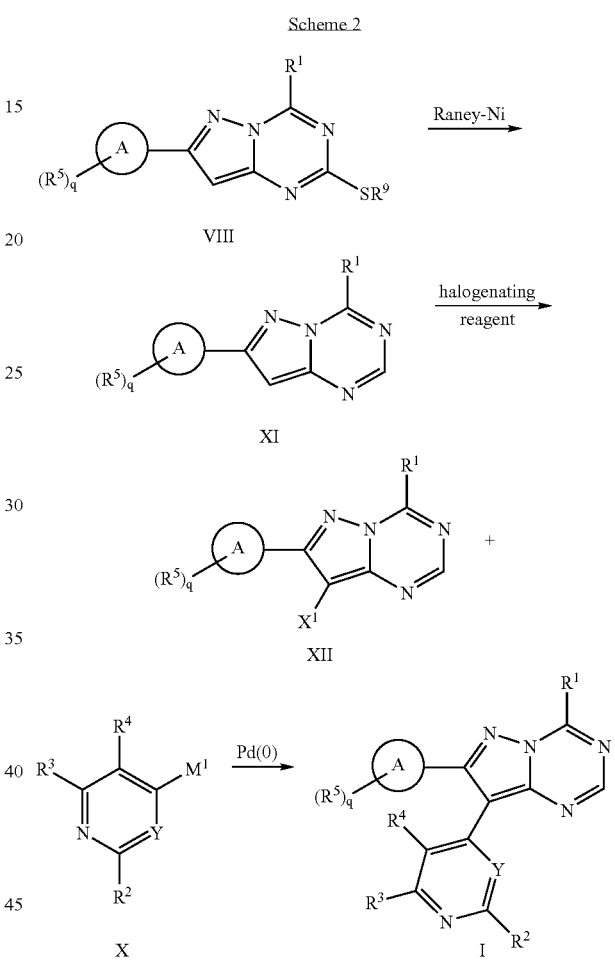

wherein:
$R^1$ is selected from the group consisting of Het, —$OR^7$, —OAy, —OHet, —$NR^7R^8$, —$NR^7Ay$ and —NHHet;
  each $R^7$ and $R^8$ are the same or different and are independently selected from the group consisting of H, alkyl, cycloalkyl, alkenyl, cycloalkenyl, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}Ay$, —$R^{10}Het$, —$R^{10}C(O)R^9$, —$R^{10}CO_2R^9$, —$R^{10}C(O)NR^9R^{11}$, —$R^{10}C(S)NR^9R^{11}$, —$R^{10}OR^9$, —$R^{10}NR^9R^{11}$, —$R^{10}NHCOR^9$, —$R^{10}NHC(NH)NR^9R^{11}$, —$R^{10}C(NH)NR^9R^{11}$, —$R^{10}NHSO_2R^9$, —$R^{10}SO_2NR^9R^{11}$, —$R^{10}SO_2R^{10}$ and —$R^{10}SO_2NHCOR^9$;
  each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

$Y^1$ is N;

p is 0;

Y is N or CH;

$R^2$ is selected from the group consisting of halo, alkyl, cycloalkyl, alkenyl, cycloalkenyl, Ay, Het, —$OR^7$, —OAy, —OHet —$NR^7R^8$, —$NR^7$Ay, —NHHet —$S(O)_nR^9$, —$S(O)_n$Ay, —$R^{10}NR^7R^8$ and —$R^{10}NR^7$Ay;

$R^3$ and $R^4$ are the same or different and are each independently selected from the group consisting of H, halo, alkyl, alkenyl, cycloalkyl, Ay, Het, —$C(O)R^7$, $C(O)$Ay, —$CO_2R^7$, —$CO_2$Ay, —$OR^7$, —OAy, —$NR^7R^8$, —$NR^7$Ay, —NHHet, —$SO_2NHR^9$, —$R^{10}OR^7$, —$R^{10}$cycloalkyl, —$R^{10}$OAy, —$R^{10}NR^7R^8$ and —$R^{10}NR^7$Ay;

Ring A is selected from the group consisting of aryl, 5–10 membered heterocyclic group and a 5–10 membered heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —$C(O)R^9$, —$C(O)$Ay, —$C(O)$Het, —$CO_2R^9$, —$C(O)NR^7R^8$, —$C(O)NR^7$Ay, —$C(S)NR^9R^{11}$, —$C(NH)NR^7R^8$, —$C(NH)NR^7$Ay, —$OR^7$, —OAy, —OHet, —$NR^7R^8$, —$NR^7$Ay, —NHHet, —$S(O)_nR^9$, —$S(O)_2NR^7R^8$, —$S(O)_2NR^7$Ay, —$R^{10}$cycloalkyl, —$R^{10}$Het, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}OR^9$, —$R^{10}NR^7R^8_1$, —$R^{10}NR^7$Ay, —$R^{10}SO_2R^9$, —$R^{10}SO_2NR^9R^{11}$, —$R^{10}SO_2NHCOR^9$, cyano, nitro and azido;

$X^1$ is chloro, bromo, or iodo; and $M^1$ is —$B(OH)_2$, —$B(ORa)_2$, —$B(Ra)_2$, —$Sn(Ra)_3$, Zn-halide, ZnRa, or Mg-halide where Ra is alkyl or cycloalkyl and halide is halo.

Generally, the process for preparing a compound of formula (I) wherein $Y^1$ is N; $R^1$ is selected from the group consisting of of Het, —$OR^7$, —OAy, —OHet, —$NR^7R^8$, —$NR^7$Ay and —NHHet and p is 0 (all formulas and all other variables having been defined above in connection with Scheme 2) comprises the steps of:

a) reducing a compound of formula (VIII) to prepare a compound of formula (XI);

b) halogenating the compound of formula (XI) to prepare a compound of formula (XII); and c) reacting a compound of formula (XII) with a compound of formula (X) to prepare a compound of formula (I).

More specifically, a compound of formula (I) wherein $Y^1$ is N; $R^1$ is selected from the group consisting of of Het, —$OR^7$, —OAy, —OHet, —$NR^7R^8$, —$NR^7$Ay and —NHHet and p is 0, can be prepared by reacting a compound of formula (XII) with a compound of formula (X).

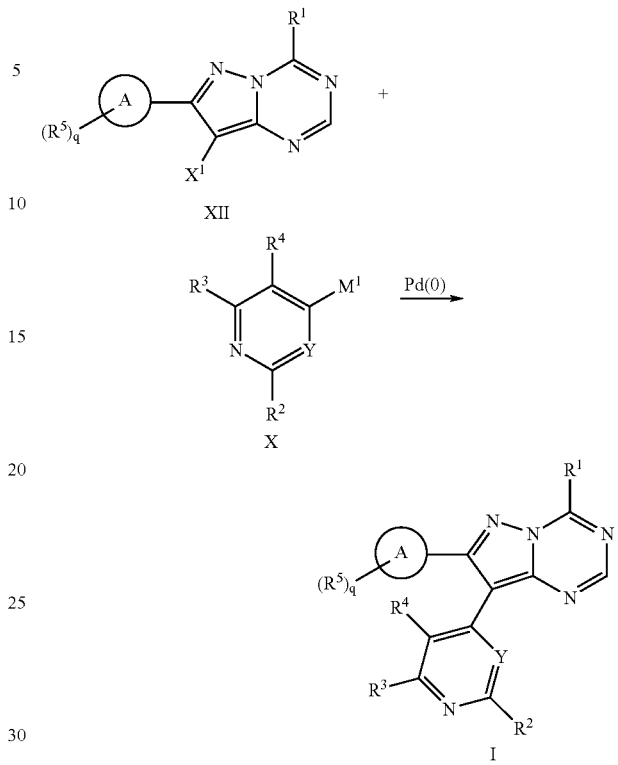

wherein all variables are as defined above in connection with Scheme 1.

This reaction may be carried out using the same procedures as described above in connection with Scheme 1, for the conversion of a compound of formula (IX) to a compound of formula (I).

A compound of formula (XII) can be prepared from a compound of formula (XI) by a halogenation procedure.

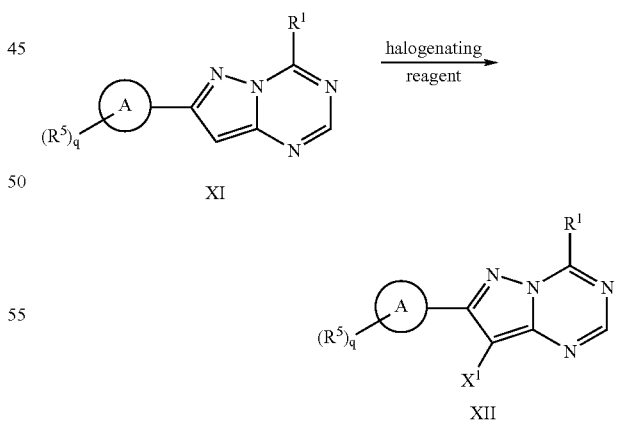

wherein all variables are as defined above in connection with Scheme 1.

Typically, the halogenation reaction is carried out by subjecting the compound of formula (XI) to a halogenating agent in a suitable solvent. Suitable halogenating agents include but are not limited to, N-bromosuccinimide, trialkylammonium tribromides, bromine, N-chlorosuccinimide, N-iodosuccinimide, iodine, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

A compound of formula (XI) can be conveniently prepared by reduction of a compound of formula (VIII).

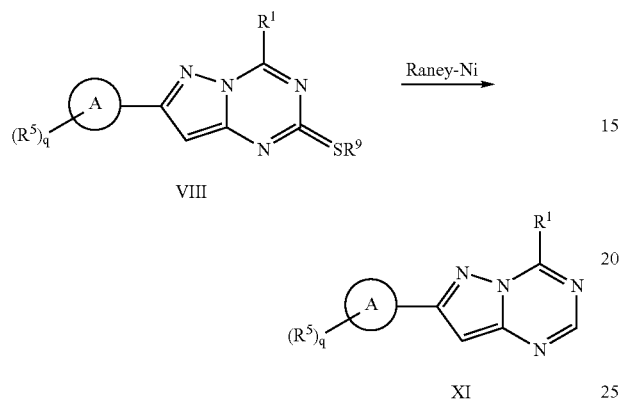

wherein all variables are as defined above in connection with Scheme 1

This method can be carried out by treating a compound of formula (VIII) with Raney-nickel in an alcohol solvent. A preferred solvent is ethanol. The reaction may optionally require heating to 50–150° C. Preparation of a compound of formula (VIII) is described in connection with Scheme 1 above.

In a further embodiment of the present invention, a compound of formula (I) wherein $Y^1$ is CH; Y is N; $R^2$ is selected from the group consisting of alkyl, cycloalkyl, alkenyl, cycloalkenyl, Ay, Het, —$OR^7$, —OAy, —OHet —$NR^7R_8$, —$NR^7$Ay, —NHHet —$S(O)_nR^9$, —$S(O)_n$Ay, —$R^{10}NR^7R^8$ and —$R^{10}NR^7$Ay; and $R^3$ and $R^4$ are H, may be conveniently prepared by the process outlined in Scheme 3 below.

Scheme 3

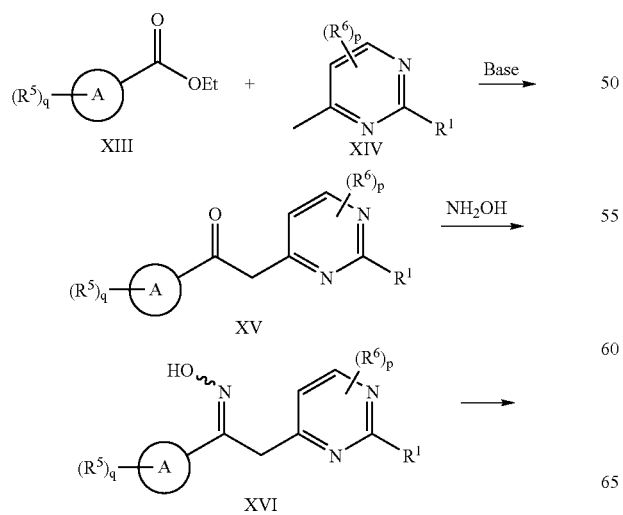

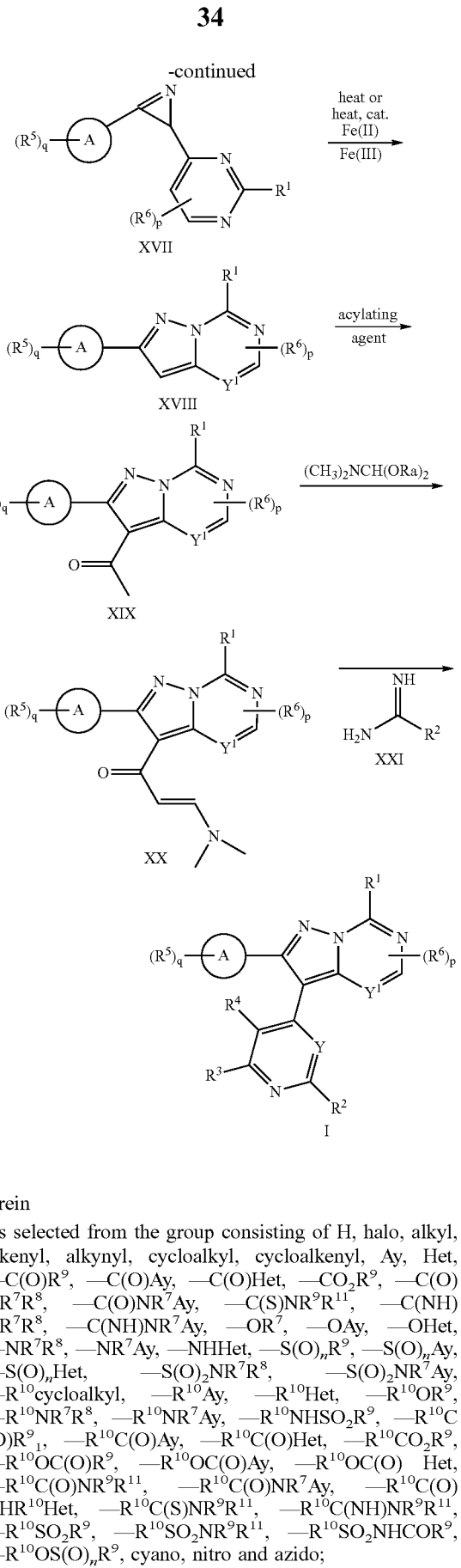

wherein $R^1$ is selected from the group consisting of H, halo, alkyl, alkenyl, alkynyl, cycloalkyl, cycloalkenyl, Ay, Het, —$C(O)R^9$, —C(O)Ay, —C(O)Het, —$CO_2R^9$, —C(O)$NR^7R^8$, —C(O)$NR^7$Ay, —C(S)$NR^9R^{11}$, —C(NH)$NR^7R^8$, —C(NH)$NR^7$Ay, —$OR^7$, —OAy, —OHet, —$NR^7R^8$, —$NR^7$Ay, —NHHet, —$S(O)_nR^9$, —$S(O)_n$Ay, —$S(O)_n$Het, —$S(O)_2NR^7R^8$, —$S(O)_2NR^7$Ay, —$R^{10}$cycloalkyl, —$R^{10}$Ay, —$R^{10}$Het, —$R^{10}OR^9$, —$R^{10}NR^7R^8$, —$R^{10}NR^7$Ay, —$R^{10}NHSO_2R^9$, —$R^{10}C(O)R^9{}_1$, —$R^{10}C(O)$Ay, —$R^{10}C(O)$Het, —$R^{10}CO_2R^9$, —$R^{10}OC(O)R^9$, —$R^{10}OC(O)$Ay, —$R^{10}OC(O)$ Het, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}OS(O)_nR^9$, cyano, nitro and azido;

each $R^7$ and $R^8$ are the same or different and are independently selected from the group consisting of H, alkyl, cycloalkyl, alkenyl, cycloalkenyl, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$Ay, —R$^{10}$Het, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$OR$^9$, —R$^{10}$NR$^9$R$^{11}$, —R$^{10}$NHCOR$^9$, —R$^{10}$NHC(NH)NR$^9$R$^{11}$, —R$^{10}$C(NH)NR$^9$R$^{11}$, —R$^{10}$NHSO$_2$R$^9$, —R$^{10}$SO$_2$NR$^9$R$^{11}$, —R$^{10}$SO$_2$R$^{10}$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1–10, and —R$^{10}$NR$^{10}$R$^{10}$;

each $R^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

p is 0, 1 or 2 when $Y^1$ is CH, p is 0 or 1 when $Y^1$ is N;

each $R^6$ is the same or different and is independently selected from the group consisting of H, halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_n$Ay, —S(O)$_n$Het, —S(O)$_2$NR$^7$R$^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$C(O)Het, —R$^{10}$CO$_2$R$^9$, —R$^{10}$OC(O)R$^9$, —R$^{10}$OC(O)Ay, —R$^{10}$OC(O)Het, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido; or when p is 2, two adjacent $R^6$ groups together with the carbon atoms to which they are bonded form a cycloalkyl or a 5- or 6-membered heterocyclic group containing 1 or 2 heteroatoms;

Y is N;

$R^2$ is selected from the group consisting of alkyl, cycloalkyl, alkenyl, cycloalkenyl, Ay, Het, —OR$^7$, —OAy, —OHet —NR$^7$R$^8$, —NR$^7$Ay, —NHHet —S(O)$_n$R$^9$, —S(O)$_n$Ay, —R$^{10}$NR$^7$R$^8$ and —R$^{10}$NR$^7$Ay;

$R^3$ and $R^4$ are both H

Ring A is selected from the group consisting of aryl, 5–10 membered heterocyclic group and a 5–10 membered heteroaryl group;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_2$NR$^7$R$^8$, —S(O)$_2$NR$^7$Ay, —R$^{10}$cycloalkyl, —R$^{10}$Het, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido; and Ra is alkyl or cycloalkyl.

Generally, the process for preparing a compound of formula (I) wherein $Y^1$ is CH; Y is N; $R^2$ is selected from the group consisting of alkyl, cycloalkyl, alkenyl, cycloalkenyl, Ay, Het, —OR$^7$, —OAy, —OHet —NR$^7$R$^8$, —NR$^7$Ay, —NHHet —S(O)$_n$R$^9$, —S(O)$_n$Ay, —R$^{10}$NR$^7$R$^8$ and —R$^{10}$NR$^7$Ay; and $R^3$ and $R^4$ are H (all formulas and all other variables having been defined above in connection with Scheme 3), comprises the steps of:

(a) reacting a 4-methylpyrimidine of formula (XIV) with an ester of formula (XIII) to prepare a compound of formula (XV);

(b) reacting the compound of formula (XV) with a hydroxylamine source to prepare a compound of formula (XVI);

(c) reacting the compound of formula (XVI) with an acylating or sulfonylating agent to prepare a compound of formula (XVII);

(d) rearranging the compound of formula (XVII) to prepare a compound of formula (XVIII);

(e) acylating the compound of formula (XVIII) to prepare a compound of formula (XIX);

(f) reacting the compound of formula (XIX) with a dimethylformamide dialkyl acetal of formula (CH$_3$)$_2$NCH(ORa)$_2$ to prepare a compound of formula (XX); and (g) reacting the compound of formula (XX) with a compound of formula (XXI) to prepare a compound of formula (I).

More specifically, a compound of formula (I) wherein wherein $Y^1$ is CH; Y is N; $R^2$ is selected from the group consisting of alkyl, cycloalkyl, alkenyl, cycloalkenyl, Ay, Het, —OR$^7$, —OAy, —OHet —NR$^7$R$^8$, —NR$^7$Ay, —NHHet —S(O)$_n$R$^9$, —S(O)$_n$Ay, —R$^{10}$NR$^7$R$^8$ and —R$^{10}$NR$^7$Ay; and $R^3$ and $R^4$ are H, can be prepared by reacting a compound of formula (XX) with a compound of formula (XXI).

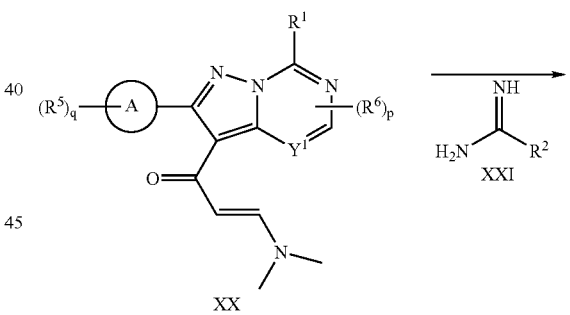

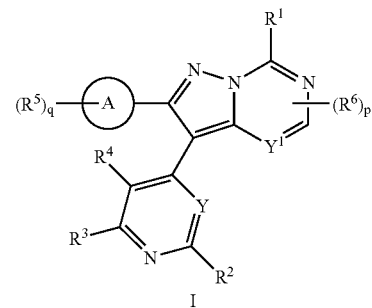

wherein all variables are as defined above in connection with Scheme 3.

This method can be readily carried out by mixing a compound of formula (XX) with a compound of formula (XXI) in a suitable solvent, optionally in the presence of a base (preferably when the amidine is in a salt form), and heating the reaction to 50–150° C. Typical solvents include lower alcohols such as methanol, ethanol, isopropanol and N,N-dimethylformamide or the like. The base is typically a sodium alkoxide, potassium carbonate, or an amine base such as triethylamine. In one embodiment, the solvent is N,N-dimethylformamide and the base is potassium carbonate, or an amine base such as triethylamine.

A compound of formula (XX) may be conveniently prepared by reacting a compound of formula (XIX) with a dimethylformamide dialkyl acetal.

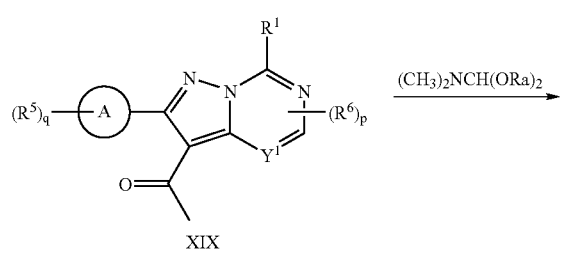

-continued

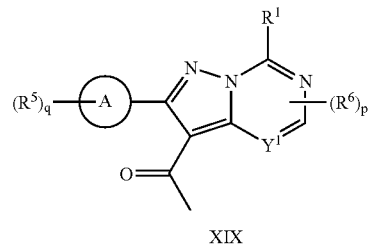

wherein all variables are as defined above in connection with Scheme 3.

Typically the acylation is carried out by treating a compound of formula (XVIII) with an acylating agent, optionally in the presence of an acid or Lewis acid catalyst in an inert solvent with optional heating. Typical acylating agents will be readily determined by those skilled in the art. One preferred acylating agent is acetic anhydride. Lewis acid catalysts are also known to those skilled in the art. One preferred Lewis acid catalyst for use in this reaction is boron trifluoride diethyl etherate. A suitable solvent is toluene. Another preferred reaction condition is catalytic sulfuric acid optionally in acetonitrile and optionally with heating.

A compound of formula (XVIII) can be conveniently prepared by rearranging an azirine compound of formula (XVII).

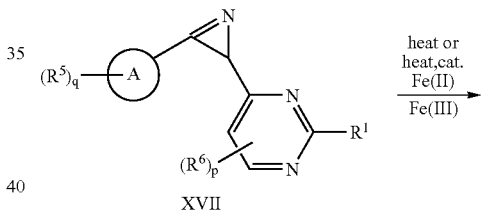

wherein all variables are as defined above in connection with Scheme 3.

Typical dimethylformamide dialkylacetal compounds for use in this method include but are not limited to dimethylformamide dimethylacetal and dimethylformamide di-tert-butylacetal. The reaction is carried out by mixing a -compound of formula (XIX) with the dimethylformamide dialkyl acetal, optionally with heating.

The foregoing procedure for the conversion of a compound of formula (XIX) to a compound of formula (I) can also be used for the conversion of a compound of formula (VIII) to a compound of formula (I) if desired.

A compound of formula (XIX) may be conveniently prepared from a compound of formula (XVIII) using an acylation procedure.

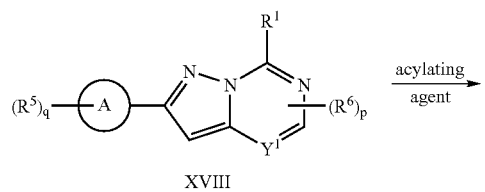

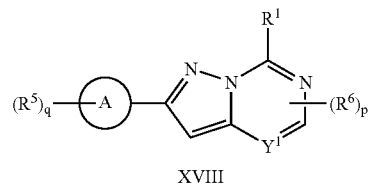

wherein all variables are as defined above in connection with Scheme 3.

The rearrangement of the azirine of formula (XVII) can be accomplished by heating a solution of the azirine of formula (XVII) in a suitable solvent at a temperature of about 160–200° C. Suitable inert solvents include, but are not limited to, 1-methyl-2-pyrrolidinone and 1,2,4-trichlorobenzene. A more preferred method for rearrangement of the azirine of formula (XVII) to a compound of formula (XVIII) involves reacting the compound of formula (XVII) with ferrous chloride ($FeCl_2$) or ferric chloride ($FeCl_3$). See, PCT Publication No. WO 01/83479, published 8 Nov. 2001 to GlaxoSmithKline Inc. This reaction is typically done in an inert solvent with heating. A preferred solvent for this reaction is 1,2-dimethoxyethane, or the like.

Typically the azirine of formula (XVII) can be prepared from an oxime compound of formula (XVI) by treatment with an acylating or sulfonylating agent in the presence of a base.

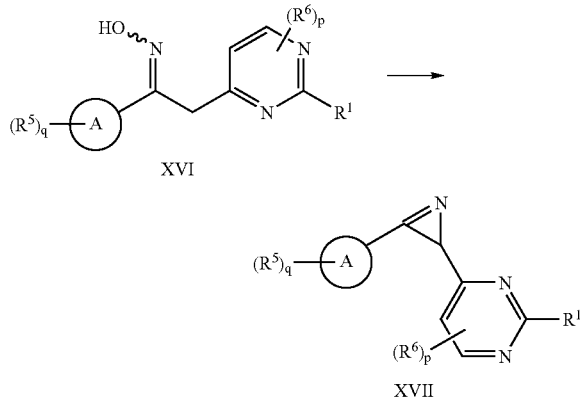

XVI

XVII wherein all variables are as defined above in connection with Scheme 3.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, and the like. The reaction may be carried out in an inert solvent such as for example, chloroform, dichloromethane, toluene or the like.

The oxime compounds of formula (XVI) are readily prepared by treating ketone compounds of formula (XV) with a hydroxylamine source, in a suitable solvent, and optionally with a base.

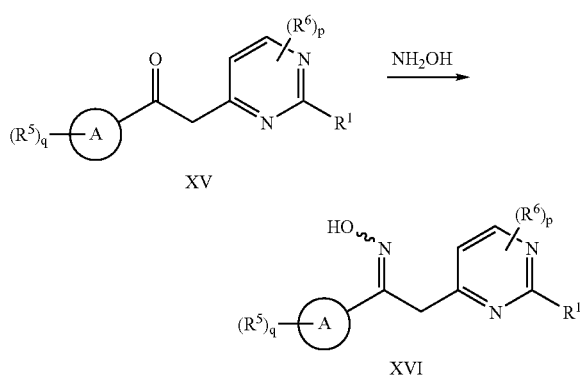

XV

XVI wherein all variables are as defined above in connection with Scheme 3.

Typically, the hydroxylamine is hydroxylamine hydrochloride and the base is an aqueous solution of sodium hydroxide. Suitable solvents include lower alcohols such as methanol, ethanol, or isopropanol.

The ketone compounds of formula (XV) can be prepared by treatment of a methylpyrimidine of formula (XIV) with an ester of formula (XIII) in the presence of a base.

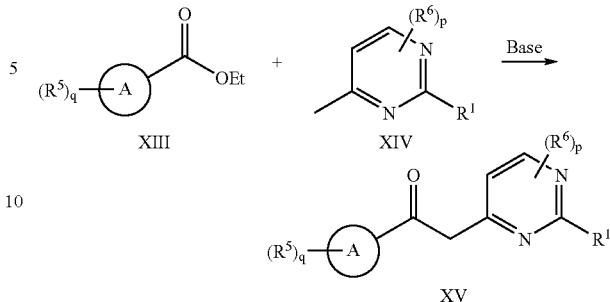

XIII    XIV

XV wherein all variables are as defined above in connection with Scheme 3.

An example of a suitable base is lithium bis(trimethylsilyl)amide in an inert solvent such as tetrahydrofuran. Ketones such as those of formula (III) can be readily prepared using procedures known to one skilled in the art and/or described in the literature (Cassity, R. P.; Taylor, L T.; Wolfe, J. F. *J.Org. Chem.* 1978, 2286).

In a further embodiment of the present invention, a compound of formula (I) wherein Y is N; $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NHHet —$S(O)_nR^9$, —$S(O)_n$Ay, —$R^{10}NR^7R^8$ and —$R^{10}NR^7$Ay; $R^3$ is selected from the group consisting of H, alkyl, alkenyl, cycloalkyl, Ay, Het, —$C(O)R^7$, $C(O)$Ay, —$CO_2R^7$, —$CO_2$Ay, —$OR^7$, —OAy, —$NR^7R^8$ (where $R^7$ and $R^8$ are not H), —$NR^7$Ay (where $R^7$ is H), —$SO_2NHR^9$, —$R^{10}OR^7$, —$R^{10}$cycloalkyl, —$R^{10}$OAy, —$R^{10}NR^7R^8$ and —$R^{10}NR^7$Ay; and $R^4$ is H, may be conveniently prepared by the process outlined in Scheme 4 below.

Scheme 4

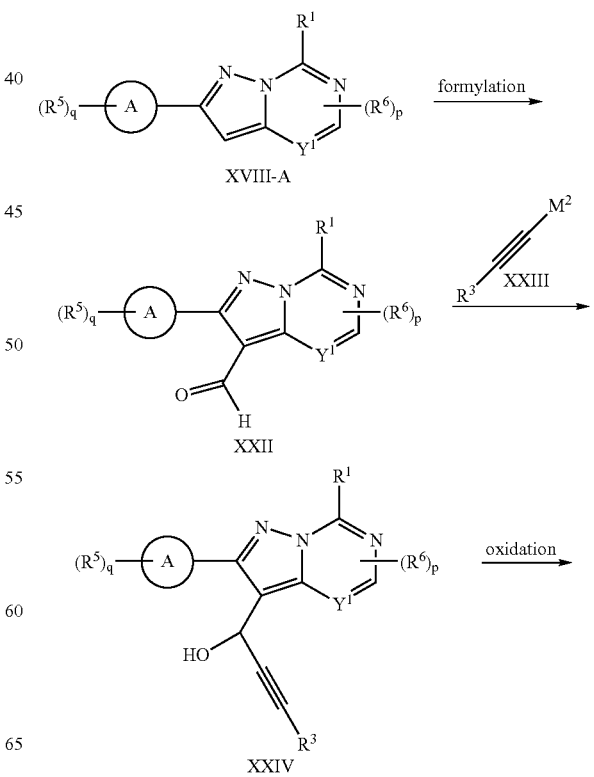

XVIII-A

XXII

XXIV

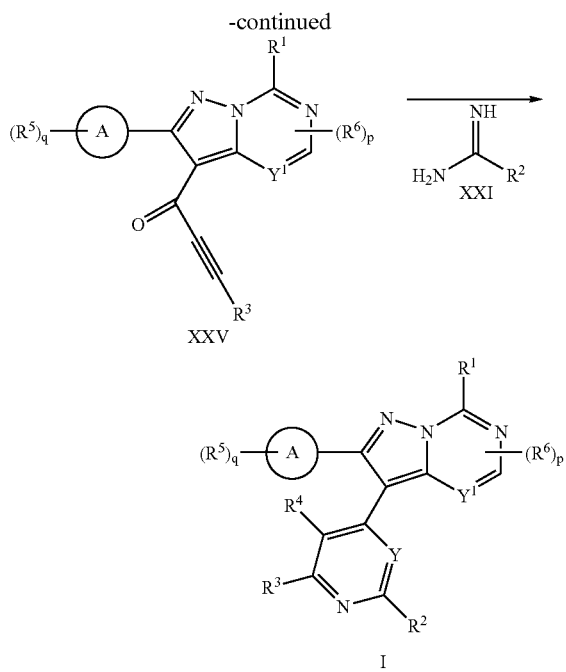

wherein:
R¹ is selected from the group consisting of H, halo, alkyl, alkenyl, alkynyl, cycloalkyl, cycloalkenyl, Ay, Het, —C(O)R⁹, —C(O)Ay, —C(O)Het, —CO₂R⁹, —C(O)NR⁷R⁸, —C(O)NR⁷Ay, —C(S)NR⁹R¹¹, —C(NH)NR⁷R⁸, —C(NH)NR⁷Ay, —OR⁷, —OAy, —OHet, —NR⁷R⁸, —NR⁷Ay, —NHHet, —S(O)ₙR⁹, —S(O)ₙAy, —S(O)ₙHet, —S(O)₂NR⁷R⁸, —S(O)₂NR⁷Ay, —R¹⁰cycloalkyl, —R¹⁰Ay, —R¹⁰Het, —R¹⁰OR⁹, —R¹⁰NR⁷R⁸, —R¹⁰NR⁷Ay, —R¹⁰NHSO₂R⁹, —R¹⁰C(O)R⁹, —R¹⁰C(O)Ay, —R¹⁰C(O)Het, —R¹⁰CO₂R⁹, —R¹⁰OC(O)R⁹, —R¹⁰OC(O)Ay, —R¹⁰OC(O)Het, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰OS(O)ₙR⁹, cyano, nitro and azido;

each R⁷ and R⁸ are the same or different and are independently selected from the group consisting of H, alkyl, cycloalkyl, alkenyl, cycloalkenyl, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰Ay, —R¹⁰Het, —R¹⁰C(O)R⁹, —R¹⁰CO₂R⁹, —R¹⁰C(O)NR⁹R¹¹, —R¹⁰C(S)NR⁹R¹¹, —R¹⁰OR⁹, —R¹⁰NR⁹R¹¹, —R¹⁰NHC(NH)NR⁹R¹¹, —R¹⁰C(NH)NR⁹R¹¹, —R¹⁰NHSO₂R⁹, —R¹⁰SO₂NR⁹R¹¹, —R¹⁰SO₂R¹⁰ and —R¹⁰SO₂NHCOR⁹;

each R⁹ and R¹¹ are the same or different and are independently selected from the group consisting of H, alkyl, cycloalkyl, —R¹⁰cycloalkyl, —R¹⁰OH, —R¹⁰(OR¹⁰)_w where w is 1–10, and —R¹⁰NR¹⁰R¹⁰;

each R¹⁰ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

Y¹ is N or CH;

p is 0, 1 or 2 when Y¹ is CH, p is 0 or 1 when Y¹ is N;

each R⁶ is the same or different and is independently selected from the group consisting of H, halo, alkyl, alkenyl, alkynyl, cycloalkyl, cycloalkenyl, Ay, Het, —C(O)R⁹, —C(O)Ay, —C(O)Het, —CO₂R⁹, —C(O)NR⁷R⁸, —C(O)NR⁷Ay, —C(S)NR⁹R¹¹, —C(NH)NR⁷R⁸, —C(NH)NR⁷Ay, —OR⁷, —OAy, —OHet, —NR⁷R⁸, —NR⁷Ay, —NHHet, —S(O)ₙR⁹, —S(O)ₙAy, —S(O)ₙHet, —S(O)₂NR⁷R⁸, —S(O)₂NR⁷Ay, —R¹⁰cycloalkyl, —R¹⁰Ay, —R¹⁰Het, —R¹⁰OR⁹, —R¹⁰NR⁷R⁸, —R¹⁰NR⁷Ay, —R¹⁰NHSO₂R⁹, —R¹⁰C(O)R⁹, —R¹⁰C(O)Ay, —R¹⁰C(O)Het, —R¹⁰CO₂R⁹, —R¹⁰OC(O)R⁹, —R¹⁰OC(O)Ay, —R¹⁰OC(O)Het, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰OS(O)ₙR⁹, cyano, nitro and azido; or when p is 2, two adjacent R⁶ groups together with the carbon atoms to which they are bonded form a cycloalkyl or a 5- or 6-membered heterocyclic group containing 1 or 2 heteroatoms;

Y is N;

R² is selected from the group consisting of alkyl, cycloalkyl, alkenyl, cycloalkenyl, Ay, Het, —OR⁷, —OAy, —OHet —NR⁷R⁸, —NR⁷Ay, —NHHet —S(O)ₙR⁹, —S(O)ₙAy, —R¹⁰NR⁷R⁸ and —R¹⁰NR⁷Ay;

R³ is selected from the group consisting of H, alkyl, alkenyl, cycloalkyl, Ay, Het, —C(O)R⁷, C(O)Ay, —CO₂R⁷, —CO₂Ay, —OR⁷, —OAy, —NR⁷R⁸ (where R⁷ and R⁸ are not H), —NR⁷Ay (where R⁷ is H), —SO₂NHR⁹, —R¹⁰OR⁷, —R¹⁰cycloalkyl, —R¹⁰OAy, —R¹⁰NR⁷R⁸ and —R¹⁰NR⁷Ay;

R⁴ is H;

Ring A is selected from the group consisting of aryl, 5–10 membered heterocyclic group and a 5–10 membered heteroaryl group;

q is 0, 1, 2, 3, 4 or 5;

each R⁵ is the same or different and is independently selected from the group consisting of halo, alkyl, alkenyl, alkynyl, cycloalkyl, cycloalkenyl, Ay, Het, —C(O)R⁹, —C(O)Ay, —C(O)Het, —CO₂R⁹, —C(O)NR⁷R⁸, —C(O)NR⁷Ay, —C(S)NR⁹R¹¹, —C(NH)NR⁷R⁸, —C(NH)NR⁷Ay, —OR⁷, —OAy, —OHet, —NR⁷R⁸, —NR⁷Ay, —NHHet, —S(O)ₙR⁹, —S(O)₂NR⁷R⁸, —S(O)₂NR⁷Ay, —R¹⁰cycloalkyl, —R¹⁰Het, —R¹⁰C(O)R⁹, —R¹⁰CO₂R⁹, —R¹⁰C(O)NR⁹R¹¹, —R¹⁰OC(O)NR⁷Ay, —R¹⁰C(O)NHR¹⁰Het, —R¹⁰C(S)NR⁹R¹¹, —R¹⁰C(NH)NR⁹R¹¹, —R¹⁰OR⁹, —R¹⁰NR⁷R⁸, —R¹⁰NR⁷Ay, —R¹⁰SO₂R⁹, —R¹⁰SO₂NR⁹R¹¹, —R¹⁰SO₂NHCOR⁹, cyano, nitro and azido; and M² is Li, Mg-halide or cerium-halide.

Generally, the process for preparing a compound of formula (I) wherein Y is N; R² is selected from the group consisting of alkyl, cycloalkyl, alkenyl, cycloalkenyl, Ay, Het, —OR⁷, —OAy, —OHet —NR⁷R⁸, —NR⁷Ay, —NHHet —S(O)ₙR⁹, —S(O)ₙAy, —R¹⁰NR⁷R⁸ and —R¹⁰NR⁷Ay; R³ is selected from the group consisting of H, alkyl, alkenyl, cycloalkyl, Ay, Het, —C(O)R⁷, C(O)Ay, —CO₂R⁷, —CO₂Ay, —OR⁷, —OAy, —NR⁷R⁸ (where R⁷ and R⁸ are not H), —NR⁷Ay (where R⁷ is H), —SO₂NHR⁹, —R¹⁰OR⁷, —R¹⁰cycloalkyl, —R¹⁰OAy, —R¹⁰NR⁷R⁸ and —R¹⁰NR⁷Ay; and R⁴ is H, comprises the following steps:

(a) formylating a compound of formula (XVIII-A) to prepare a compound of formula (XXII);

(b) reacting the compound of formula (XXII) with a compound of formula (XXIII) to prepare a compound of formula (XXIV);

(c) oxidizing the compound of formula (XXIV) to prepare a compound of formula (XXV); and (d) reacting the compound of formula (XXV) with a compound of formula (XXI) to prepare the compound of formula (I).

More specifically, a compound of formula (I) wherein Y is N; $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NHHet —$S(O)_nR^9$, —$S(O)_n$Ay, —$R^{10}NR^7R^8$ and —$R^{10}NR^7$Ay; $R^3$ is selected from the group consisting of H, alkyl, alkenyl, cycloalkyl, Ay, Het, —$C(O)R^7$, $C(O)$Ay, —$CO_2R^7{}_1$, —$CO_2$Ay, —$OR^7$, —OAy, —$NR^7R^8$ (where $R^7$ and $R^8$ are not H), —$NR^7$Ay (where $R^7$ is H), —$SO_2NHR^9$, —$R^{10}OR^7$, —$R^{10}$cycloalkyl, —$R^{10}$OAy, —$R^{10}NR^7R^8$ and —$R^{10}NR^7$Ay; and $R^4$ is H, may be prepared by reacting a compound of formula (XXV) with a compound of formula (XXI).

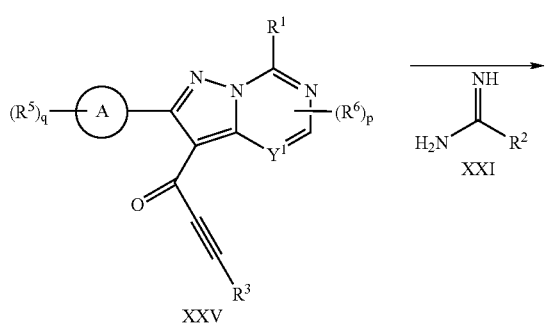

wherein all variables are as defined above in connection with Scheme 4.

This method can be readily carried out by mixing a compound of formula (XXV) with a compound of formula (XXI) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

A compound of formula (XXV) may be conveniently prepared by oxidation of a compound of formula (XXIV).

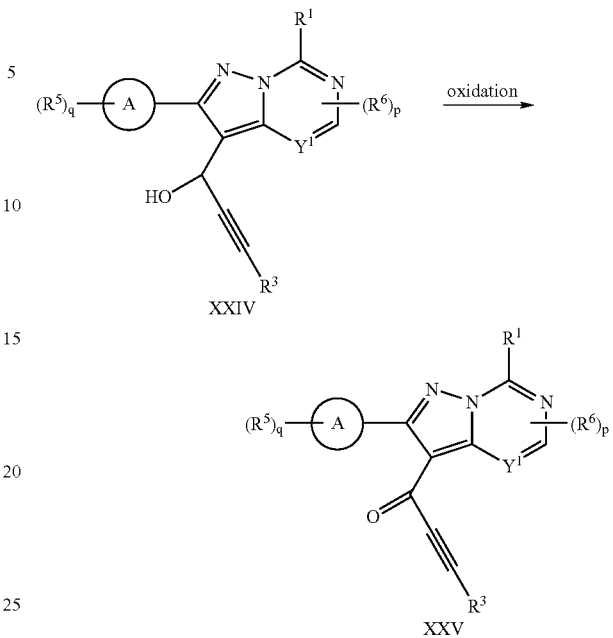

wherein all variables are as defined above in connection with Scheme 4.

Typical oxidizing agents include but are not limited to, manganese dioxide, and the like, in an inert solvent Suitable inert solvents include but are not limited to, dichloromethane, chloroform, N,N-dimethylformamide, ether, and the like.

A compound of formula (XXIV) may be conveniently prepared by reacting a compound of formula (XXII) with a compound of formula (XXIII).

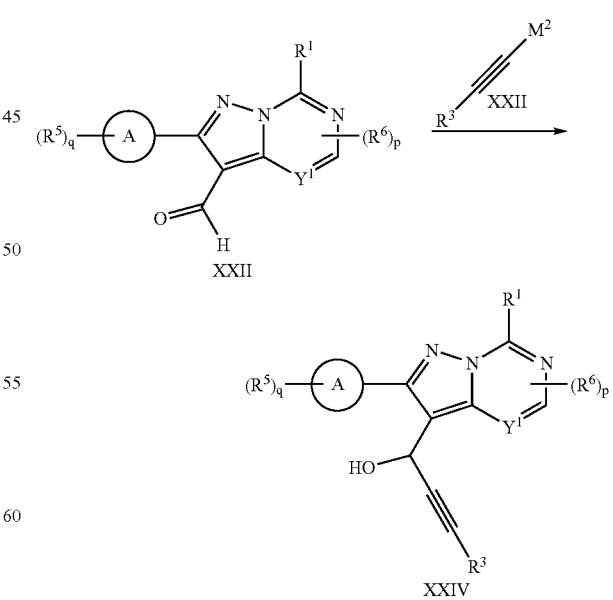

wherein all variables are as defined above in connection with Scheme 4.

Suitable metals ($M^2$) in the compounds of formula (XXIII) include but are not limited to, lithium, magnesium (II) halides, cerium(III) halides, and the like. A compound of formula (XXIII) may be purchased from commercial sources or prepared by methods known to one skilled in the art.

A compound of formula (XXII) may be conveniently prepared from a compound of formula (XVIII-A) by a formulation procedure.

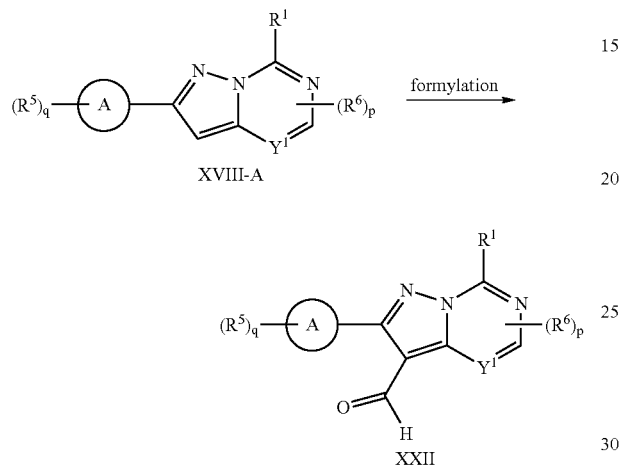

wherein all variables are as defined above in connection with Scheme 4.

Typically the formylation is carried out via the Vilsmeier-Haack reaction. The Vilsmeier-Haack reagents can be purchased from commercial sources or prepared in situ. Typical conditions include, but are not limited to treating a compound of formula (XVIII) with a premixed solution of phosphorous oxychloride in N,N-dimethylformamide optionally with heating the reaction to about 50–150° C. The compounds of formula (XVIII-A) may be prepared according to the process described in previous Schemes.

A compound of formula (I) wherein Y is N; and $R^2$ is selected from the group consisting of alkyl cycloalkyl, alkenyl, cycloalkenyl, Ay, Het, —$OR^7$, —OAy, —OHet —$NR^7R^8$, —$NR^7$Ay, —NHHet —$S(O)_nR^9$, —$S(O)_n$Ay, —$R^{10}NR^7R^8$ and —$R^{10}NR^7$Ay, may be conveniently prepared by the process outlined in Scheme 5 below.

Scheme 5

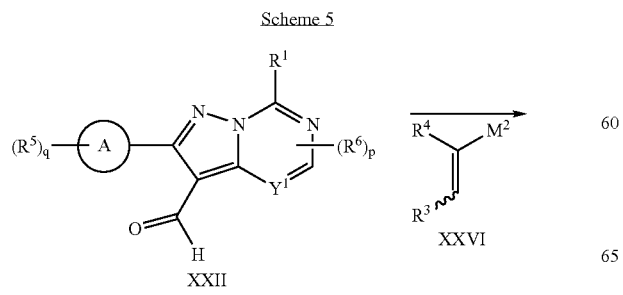

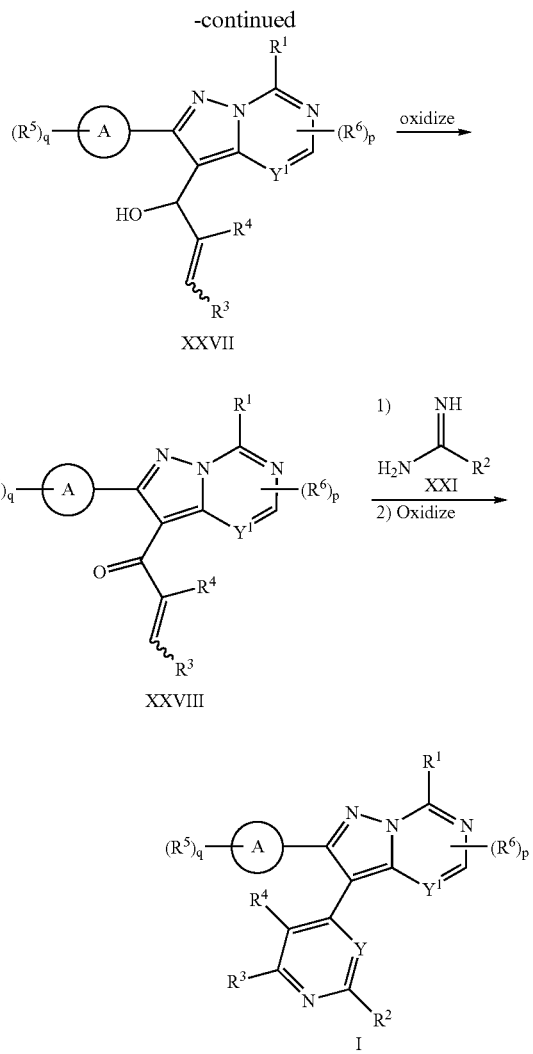

wherein:
$R^1$ is selected from the group consisting of H, halo, alkyl, alkenyl, alkynyl, cycloalkyl, cycloalkenyl, Ay, Het, —$C(O)R^9$, —C(O)Ay, —C(O)Het, —$CO_2R^9$, —$C(O)NR^7R^8$, —$C(O)NR^7$Ay, —$C(S)NR^9R^{11}$, —$C(NH)NR^7R_8$, —$C(NH)NR^7$Ay, —$OR^7$, —OAy, —OHet, —$NR^7R^8$, —$NR^7$Ay, —NHHet, —$S(O)_nR^9$; $S(O)_n$Ay, —$S(O)_n$Het, —$S(O)_2NR^7R^8$, —$S(O)_2NR^7$Ay, —$R^{10}$cycloalkyl, —$R^{10}$Ay, —$R^{10}$Het, —$R^{10}OR^9$, —$R^{10}NR^7R^8$, —$R^{10}NR^7$Ay, —$R^{10}NHSO_2R^9$, —$R^{10}C(O)R^9$, —$R^{10}C(O)$Ay, —$R^{10}C(O)$Het, —$R^{10}CO_2R^9$, —$R^{10}OC(O)R^9$, —$R^{10}OC(O)$Ay, —$R^{10}C(O)$Het, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}OS(O)_nR^9$, cyano, nitro and azido;
each $R^7$ and $R^8$ are the same or different and are independently selected from the group consisting of H, alkyl, cycloalkyl, alkenyl, cycloalkenyl, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}$Ay, —$R^{10}$Het, —$R^{10}C(O)R^9$, —$R^{10}CO_2R^9$, —$R^{10}C(O)NR^9R^{11}$, —$R^{10}C(S)NR^9R^{11}$, —$R^{10}OR^9$, —$R^{10}NR^9R^{11}$, —$R^{10}NHCOR^9$, —$R^{10}NHC(NH)$ NR$^9$R$^{11}$, —R$^{10}$C(N H)NR$^9$R$^{11}$, —R$^{10}$NHSO$_2$R$^9$, —R$^{10}$SO$_2$NR$^9$R$^{11}$, —R$^{10}$SO$_2$R$^{10}$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1–10, and —R$^{10}$NR$^{10}$R$^{10}$;

each R$^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

Y$^1$ is N or CH;

p is 0, 1 or 2 when Y$^1$ is CH, p is 0 or 1 when Y$^1$ is N;

each R$^6$ is the same or different and is independently selected from the group consisting of H, halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_n$Ay, —S(O)$_n$Het, —S(O)$_2$NR$^7$R$^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$C(O)Het, —R$^{10}$CO$_2$R$^9$, —R$^{10}$OC(O)R$^9$, —R$^{10}$OC(O)Ay, —R$^{10}$OC(O)Het, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido; or when p is 2, two adjacent R$^6$ groups together with the carbon atoms to which they are bonded form a cycloalkyl or a 5- or 6-membered heterocyclic group containing 1 or 2 heteroatoms;

Y is N;

R$^2$ is selected from the group consisting of alkyl, cycloalkyl, alkenyl, cycloalkenyl, Ay, Het, —OR$^7$, —OAy, —OHet —NR$^7$R$^8$, —NR$^7$Ay, —NHHet —S(O)$_n$R$^9$, —S(O)$_n$Ay, —R$^{10}$NR$^7$R$^8$ and —R$^{10}$NR$^7$Ay;

R$^3$ and R$^4$ are the same or different and are each independently selected from the group consisting of H, halo, alkyl, alkenyl, cycloalkyl, Ay, Het, —C(O)R$^7$, C(O)Ay, —CO$_2$R$^7$, —CO$_2$Ay, —OR$^7$, —OAy, —NR$^7$R$^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7$R$^8$ and —R$^{10}$NR$^7$Ay;

Ring A is selected from the group consisting of aryl, 5–10 membered heterocyclic group and a 5–10 membered heteroaryl group;

q is 0, 1, 2, 3, 4 or 5;

each R$^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_2$NR$^7$R$^8$, —S(O)$_2$NR$^7$Ay, —R$^{10}$cycloalkyl, —R$^{10}$Het, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido; and M$^2$ is Li, Mg-halide or cerium-halide, wherein halide is halo.

Generally, the process for preparing a compound of formula (I) wherein Y is N and R$^2$ is selected from the group consisting of alkyl, cycloalkyl, alkenyl, cycloalkenyl, Ay, Het, —OR$^7$, —OAy, —OHet —NR$^7$R$^8$, —NR$^7$Ay, —NH-Het —S(O)$_n$R$^9$, —S(O)$_n$Ay, —R$^{10}$NR$^7$R$^8$ and —R$^{10}$NR$^7$Ay, comprises the following steps:

(a) reacting a compound of formula (XXII) with a compound of formula (XXVI) to prepare a compound of formula (XXVII);

(b) oxidizing the compound of formula (XXVII) to prepare a compound of formula (XXVIII); and c) reacting a compound of formula (XXVIII) with a compound of formula (XXI) followed by oxidative aromatization to prepare a compound of formula (I).

More specifically, a compound of formula (I) wherein Y is N and R$^2$ is selected from the group consisting of alkyl, cycloalkyl, alkenyl, cycloalkenyl, Ay, Het, —OR$^7$, —OAy, —OHet —NR$^7$R$^8$, —NR$^7$Ay, —NHHet —S(O)$_n$R$^9$, —S(O)$_n$Ay, —R$^{10}$NR$^7$R$^8$ and —R$^{10}$NR$^7$Ay, can be prepared by reacting a compound of formula (XXVIII) with a compound of formula (XXI) followed by oxidative aromatization.

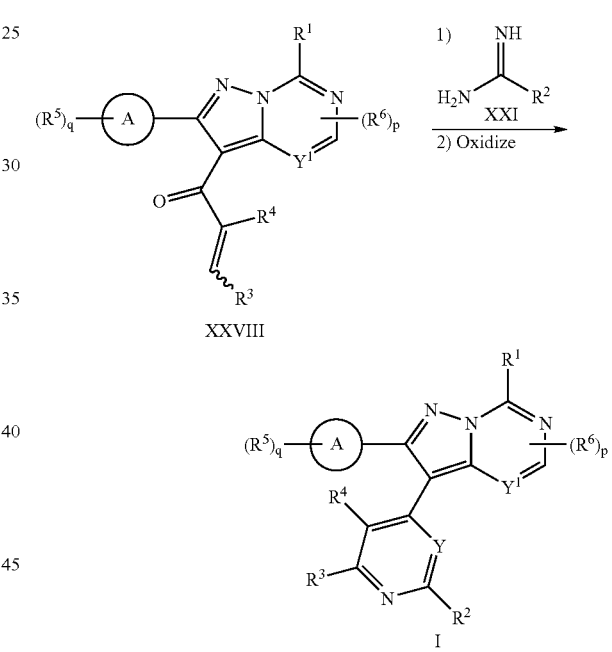

wherein all variables are as defined above in connection with Scheme 5.

The condensation is conveniently carried out by treating the compound of formula (XXVIII) with a compound of formula (XXI) in an inert solvent, optionally in the presence of a base. The reaction may be heated to about 50–150° C. or performed at ambient temperature. Suitable inert solvents include lower alcohols such as, for example, methanol, ethanol, isopropanol and the like. The base is typically a sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Conveniently in the same reaction vessel, the dihydropyrimidine intermediate may be oxidized to a compound of formula (I) by the addition of an oxidizing agent The reaction may be heated to 50–150° C. or performed at ambient temperature. Typically, the oxidizing agent is oxygen (O₂), palladium on carbon, 2,3-dichloro-5,6-dicyano-1,4-benzoquinone, or the like.

A compound of formula (XXVIII) may be conveniently prepared by oxidation of a compound of formula (XXVII).

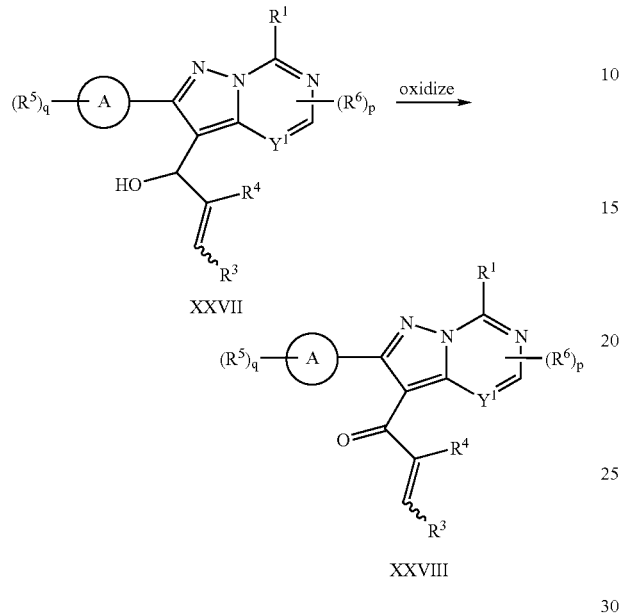

wherein all variables are as defined above in connection with Scheme 5.

Typical oxidizing agents for the oxidation of a compound of formula (XXVII) include but are not limited to manganese dioxide, and the like. The oxidation is typically carried out in an inert solvent such as for example, dichloromethane, chloroform, N,N-dimethylformamide, ether, and the like.

A compound of formula (XXVII) may be conveniently prepared by reacting a compound of formula (XXII) with a compound of formula (XXVI).

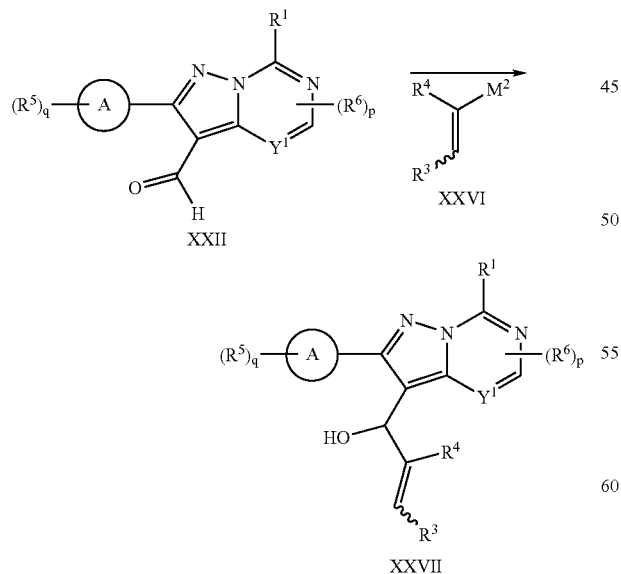

wherein all variables are as defined above in connection with Scheme 5.

A compound of formula (XXVI) may be purchased from commercial sources or prepared by methods known to one skilled in the art. A compound of formula (XXII) may be prepared using the methods described in connection with Schemes 3 and 4 above.

In a further embodiment of the invention, a compound of formula (I), may be conveniently prepared by the process outlined in Scheme 6 below.

Scheme 6

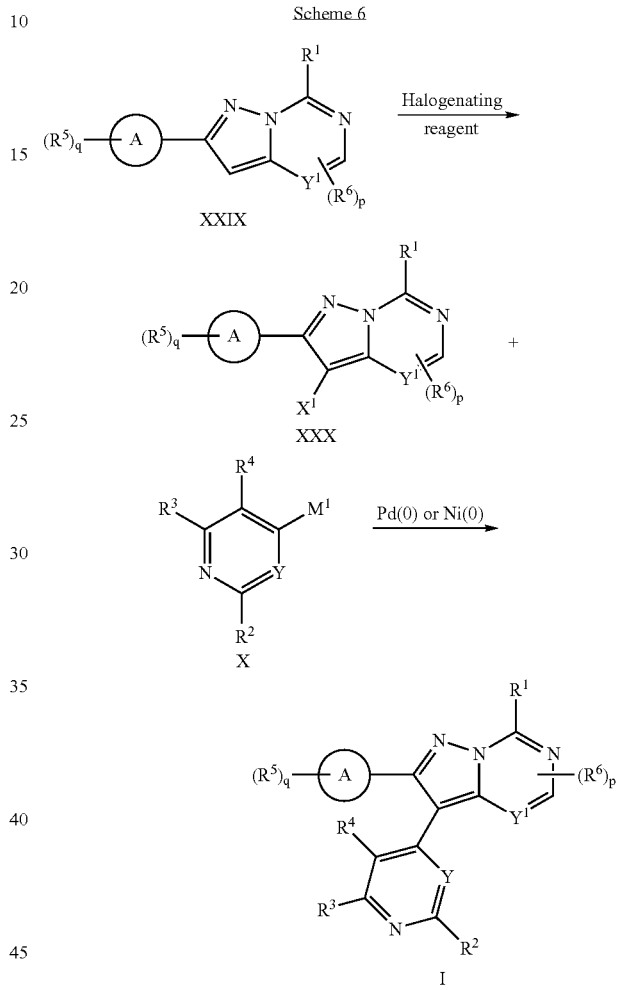

wherein
$R^1$ is selected from the group consisting of H, halo, alkyl, alkenyl, alkynyl, cycloalkyl, cycloalkenyl, Ay, Het, —C(O)R⁹, —C(O)Ay, —C(O)Het, —CO₂R⁹, —C(O)NR⁷R⁸, —C(O)NR⁷Ay, —C(S)NR⁹R¹¹, —C(NH)NR⁷R⁸, —C(NH)NR⁷Ay, —OR⁷, —OAy, —OHet, —NR⁷R⁸, —NR⁷Ay, —NHHet, —S(O)ₙR⁹, —S(O)ₙAy, —S(O)ₙHet, —S(O)₂NR⁷R⁸, —S(O)₂NR⁷Ay, —R¹⁰cycloalkyl, —R¹⁰Ay, —R¹⁰Het, —R¹⁰OR⁹, —R¹⁰NR⁷R⁸, —R¹⁰NR⁷Ay, —R¹⁰NHSO₂R⁹, —R¹⁰C(O)R⁹, —R¹⁰C(O)Ay, —R¹⁰C(O)Het, —R¹⁰CO₂R⁹, —R¹⁰OC(O)R⁹, —R¹⁰OC(O)Ay, —R¹⁰OC(O)Het, —R¹⁰C(O)NR⁹R¹¹, —R¹⁰C(O)NR⁷Ay, —R¹⁰C(O)NHR¹⁰Het, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰OS(O)ₙR⁹, cyano, nitro and azido;

each $R^7$ and $R^8$ are the same or different and are independently selected from the group consisting of H, alkyl, cycloalkyl, alkenyl, cycloalkenyl, —C(O)R⁹, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}$Ay, —$R^{10}$Het, —$R^{10}C(O)R^9$, —$R^{10}CO_2R^9$, —$R^{10}C(O)NR^9R^{11}$, —$R^{10}C(S)NR^9R^{11}$, —$R^{10}OR^9$, —$R^{10}NR^9R^{11}$, —$R^{10}NHCOR^9$, —$R^{10}NHC(NH)NR^9R^{11}$, —$R^{10}C(NH)NR^9R^{11}$, —$R^{10}NHSO_2R^9$, —$R^{10}SO_2NR^9R^{11}$, —$R^{10}SO_2R^{10}$ and —$R^{10}SO_2NHCOR^9$;

each $R^9$ and $R^{11}$ are the same or different and are independently selected from the group consisting of H, alkyl, cycloalkyl, —$R^{10}$cycloalkyl, —$R^{10}OH$, —$R_{10}(OR^{10})_w$ where w is 1–10, and —$R^{10}NR^{10}R^{10}$;

each $R^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

$Y^1$ is N or CH;

p is 0, 1 or 2 when $Y^1$ is CH, p is 0 or 1 when $Y^1$ is N;

each $R^6$ is the same or different and is independently selected from the group consisting of H, halo, alkyl, alkenyl, alkynyl, cycloalkyl, cycloalkenyl, Ay, Het, —$C(O)R^9$, —$C(O)$Ay, —$C(O)$Het, —$CO_2R^9$, —$C(O)NR^7R^8$, —$C(O)NR^7$Ay, —$C(S)NR^9R^{11}$, —$C(NH)NR^7R^8$, —$C(NH)NR^7$Ay, —$OR^7$, —$O$Ay, —$O$Het, —$NR^7R^8$, —$NR^7$Ay, —NHHet, —$S(O)_nR^9$, —$S(O)_n$Ay, —$S(O)_n$Het, —$S(O)_2NR^7R^8$, —$S(O)_2NR^7$Ay, —$R^{10}$cycloalkyl, —$R^{10}$Ay, —$R^{10}$Het, —$R^{10}OR^9$, —$R^{10}NR^7R^8$, —$R^{10}NR^7$Ay, —$R^{10}NHSO_2R^9$, —$R^{10}C(O)R^9$, —$R^{10}C(O)$Ay, —$R^{10}C(O)$Het, —$R^{10}CO_2R^9$, —$R^{10}OC(O)R^9$, —$R^{10}OC(O)$Ay, —$R^{10}OC(O)$Het, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}OS(O)_nR^9$, cyano, nitro and azido; or when p is 2, two adjacent $R^6$ groups together with the carbon atoms to which they are bonded form a cycloalkyl or a 5- or 6-membered heterocyclic group containing 1 or 2 heteroatoms;

Y is N or CH;

$R^2$ is selected from the group consisting of halo, alkyl, cycloalkyl, alkenyl, cycloalkenyl, Ay, Het, —$OR^7$, —$O$Ay, —$O$Het —$NR^7R^8$, —$NR^7$Ay, —NHHet —$S(O)_nR^9$, —$S(O)_n$Ay, —$R^{10}NR^7R^8$ and —$R^{10}NR^7$Ay;

$R^3$ and $R^4$ are the same or different and are each independently selected from the group consisting of H, halo, alkyl, alkenyl, cycloalkyl, Ay, Het, —$C(O)R^7$, $C(O)$Ay, —$CO_2R^7$, —$CO_2$Ay, —$OR^7$, —$O$Ay, —$NR^7R^8$, —$NR^7$Ay, —NHHet, —$SO_2NHR^9$, —$R^{10}OR^7$, —$R^{10}$cycloalkyl, —$R^{10}O$Ay, —$R^{10}NR^7R^8$ and —$R^{10}NR^7$Ay;

Ring A is selected from the group consisting of aryl, 5–10 membered heterocyclic group and a 5–10 membered heteroaryl group;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, —$C(O)R^9$, —$C(O)$Ay, —$C(O)$Het, —$CO_2R^9$, —$C(O)NR^7R^8$, —$C(O)NR^7$Ay, —$C(S)NR^9R^{11}$, —$C(NH)NR^7R^8$, —$C(NH)NR^7$Ay, —$OR^7$, —$O$Ay, —$O$Het, —$NR^7R^8$, —$NR^7$Ay, —NHHet, —$S(O)_nR^9$, —$S(O)_2NR^7R^8$, —$S(O)_2NR^7$Ay, —$R^{10}$cycloalkyl, —$R^{10}$Het, —$R^{10}C(O)R^9$, —$R^{10}CO_2R^9$, —$R^{10}C(O)NR^9R^{11}$, —$R^{10}C(O)NR^7$Ay, —$R^{10}C(O)NHR^{10}$Het, —$R^{10}C(S)NR^9R^{11}$, —$R^{10}C(NH)NR^9R^{11}$, —$R^{10}OR^9$, —$R^{10}NR^7R^8$, —$R^{10}NR^7$Ay, —$R^{10}SO_2R^9$, —$R^{10}SO_2NR^9R^{11}$, —$R^{10}SO_2NHCOR^9$, cyano, nitro and azido;

$X^1$ is chloro, bromo, or iodo; and $M^1$ is —$B(OH)_2$, —$B(ORa)_2$, —$B(Ra)_2$, —$Sn(Ra)_3$, Zn-halide, ZnRa, or Mg-halide where Ra is alkyl or cycloalkyl and halide is halo.

Generally, the process for preparing a compound of formula (I) (all formulas and variables having been defined above in connection with Scheme 6), comprises the following steps:

a) halogenating a compound of formula (XXIX) to prepare a compound of formula (XXX); and b) reacting the compound of formula (XXX) with a compound of formula (X) to prepare a compound of formula (I).

More specifically, this sequence of reactions may be carried out in an analogous manner as described above in connection with Scheme 2. It should be noted that a compound of formula (XXX) is in fact the same as a compound of formula (XII) described in Scheme 2 when $Y^1$ is N and $R^6$ is H. It should also be noted that a compound of formula (XXIX) is in fact the same as a compound of formula (XI) when $Y^1$ is N and p is 0, and the same as a compound of formula (XVIII) when $Y^1$ is defined as CH. A compound of the formula (XXIX) can be prepared using the methods described above in connection with Schemes 1–4 using techniques known to those in the art.

In each of the foregoing synthetic processes, the steps are described in a specific order. However, one skilled in the art will readily appreciate that various steps within each of the reaction schemes may be conducted in a different order. Hence, the order in which the steps of the process are performed is not critical to the invention. The present invention contemplates and includes analogous processes wherein the order of the steps differs from the specific embodiment described herein.

As will be apparent to those skilled in the art, a compound of formula (I) may be converted to another compound of formula (I) using techniques well known in the art, i.e., a particular compound of formula (I) may be used as an intermediate in processes for preparing other compounds of formula (I). For example, one method of converting a compound of formula (I) to another compound of formula (I) comprises the steps of:

a) oxidizing a compound of formula (I-A) to prepare a compound of formula (I-B); and b) optionally reacting a compound of formula (I-B) with an oxygen or amine nucleophile of formula $R^2$, wherein $R^2$ is selected from the group consisting of —$NR^7R^8$, —$OR^7$, Het attached through N, —NHHet, $NHR^{10}$Het, OHet and —$OR^{10}$Het to prepare a compound of formula (I) wherein $R^2$ is selected from the group consisting of Het attached through N, —$OR^7$, —$O$Het, —$NR^7R^8$ and —NHHet.

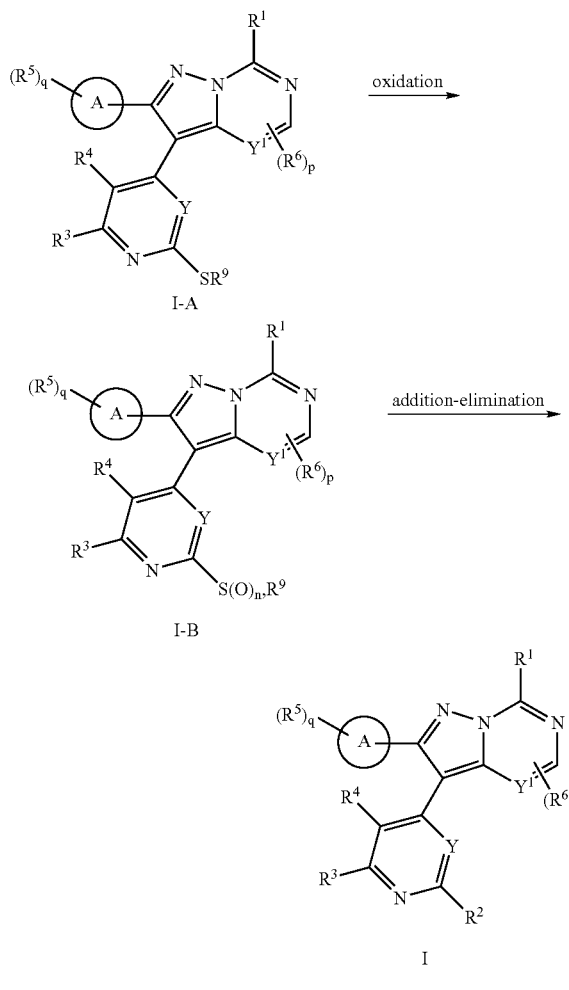

I-A

I-B

I wherein n' is 1 or 2;

R² is selected from the group consisting of Het attached through N, —OR⁷, —OHet, —NR⁷R⁸ and —NHHet, all other variables are as defined according to any process described above.

More specifically, a compound of formula (I) wherein R² is selected from the group consisting of Het attached through N, —OR⁷, —OHet, —NR⁷R⁸ and —NHHet; can be prepared by reacting a compound of formula (I-B) (i.e., a compound of formula (I) wherein R² is S(O)$_{n'}$R⁹ where n' is 1 or 2, with an oxygen or amine nucleophile of formula R², wherein R² is selected from the group consisting of Het attached through N, —OR⁷, —OHet, —NR⁷R⁸ and —NH-Het. The reaction may be carried out neat or in a suitable solvent and may be heated to about 50–150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine.

A compound of formula (I-B) may be conveniently prepared by reacting a compound of formula (I-A) (i.e., a compound of formula (I) wherein R² is: —S(O)$_n$R⁹ where n is 0) with an oxidizing agent in an inert solvent, optionally in the presence of a base. Typically the oxidizing agent is a peracid such as 3-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like. If the compound of formula (I-A) contains oxidizeable nitrogens, it may be preferred to perform the oxidation under acidic conditions. Acetic acid, or other suitable acids known to those skilled in the art can be added to make the solution acidic.

Compounds of formula (I-A) are prepared by methods described above in Schemes 1 through 6 wherein R²=SR⁹.

In an analogus procedure, a compound of formula (I) wherein at least one R⁶ is —SR⁹, may be converted to another compound of formula (I) wherein at least one R⁶ is selected from the group consisting Het attached through N, —OR⁷, —OHet —NR⁷R⁸ and —NHHet. The process comprises the steps of: a) oxidizing a compound of formula (I-AA) to prepare a compound of formula (I-BB); and b) optionally reacting a compound of formula (I-BB) with an oxygen or amine nucleophile of formula R⁶, wherein R⁶ is selected from the group consisting of Het attached through N, —OR⁷, —OHet —NR⁷R⁸ and —NHHet to prepare a compound of formula I wherein at least one R⁶ is selected from the group consisting Het attached through N, —OR⁷, —OHet —NR⁷R⁸ and —NHHet.

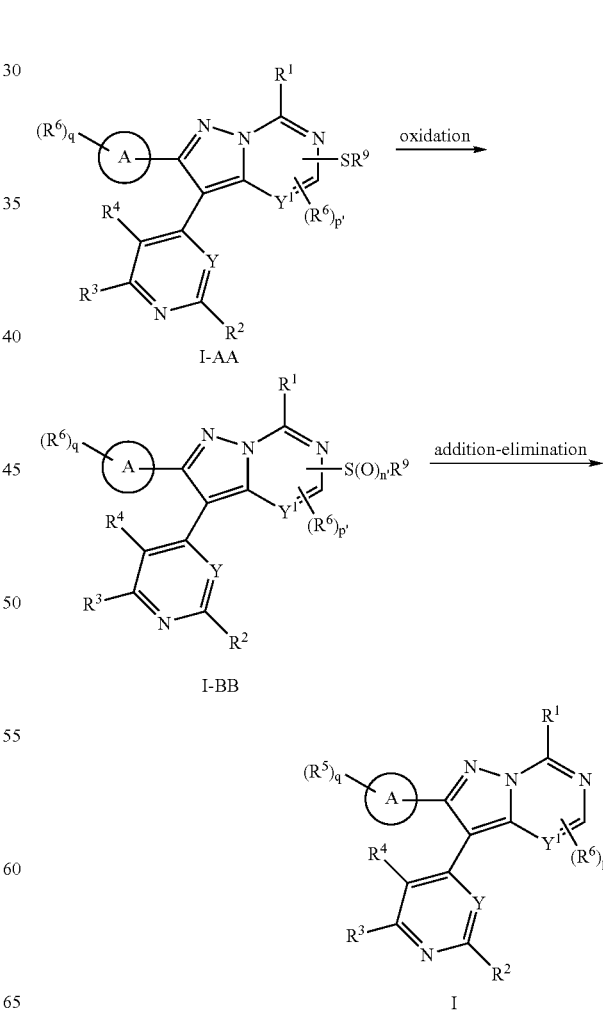

I-AA

I-BB

I wherein p' is 0 when $Y^1$ is N or p' is 0 or 1 when $Y^1$ is CH;

at least one $R^6$ is selected from the group consisting of Het attached through N, —$OR^7$, —OHet —$NR^7R^8$ and —NHHet; and all other variables are as defined according to any process described above.

Compounds of formula (I-AA) are prepared by methods described above in Schemes 1 through 6 wherein at least one $R^6$=$SR^9$.

Another particularly useful method for converting a compound of formula (I) to another compound of formula (I) comprises reacting a compound of formula (I-C) (i.e., a compound of formula (I) wherein $R^2$ is fluoro) with an amine, and optionally heating the mixture to about 50–150° C. to prepare a compound of formula (I-D) (i.e., a compound of formula (I) wherein $R^2$ is Het bonded through N, —$NR^7R^8$, —$NR^7$Ay and —NHHet).

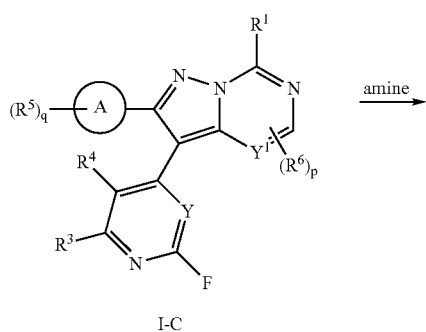

I-C

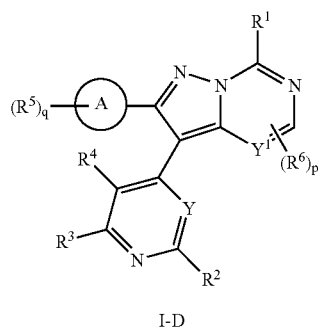

I-D wherein all other variables are as defined in any process described above.

This procedure may be carried out by mixing a compound of formula (I-C) in a neat amine (i.e., $R^2$), or in a suitable solvent with an excess of an amine to produce a compound of formula (I-D). Typically the solvent is a lower alcohol such as methanol, ethanol, isopropanol or the like. Other suitable solvents may include N,N-dimethylformamide, 1-methyl-2-pyrrolidine or the like.

As a further example, a compound of formula (I-E) may be converted to a compound of formula (I-F) using either of two methods.

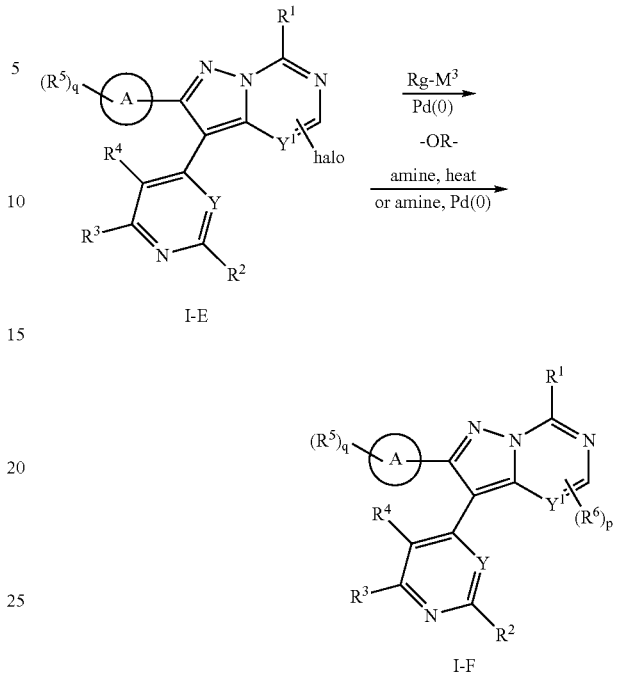

wherein $M^3$ is $B(OH)_2$, $B(ORa)_2$, $B(Ra)_2$, $Sn(Ra)_3$, Zn-halide; Zn—Ra or Mg-halide, Rg is Ay or Het, and all other variables are as defined in any process described above.

Thus, the present invention provides a process for converting a compound of formula (I-E) to a compound of formula (I-F) which comprises either: (1) replacing a halogen of the compound of formula (I-E) with an amine; or (2) coupling the compound of formula (I-E) with a metal compound of the formula Rg-$M^3$ where $M^3$ is $B(OH)_2$, $B(ORa)_2$, $B(Ra)_2$, $Sn(Ra)_3$, Zn-halide; Zn-Ra or Mg-halide.

As a further example, a compound of formula (I-G) (i.e., a compound of formula (I) wherein q is 1 or more and at least one $R^5$ is O-methyl) may be converted to a compound of formula (I-H) (i.e., a compound of formula (I) wherein q is 1 or more and at least one $R^5$ is OH) using conventional demethylation techniques. Additionally, a compound of formula (I-H) may optionally be converted to a compound of formula (I-J) (i.e., a compound of formula (I) wherein q is 1 or more and at least one $R^5$ is $OR^{10}$). For example, the foregoing conversions are represented schematically as follows:

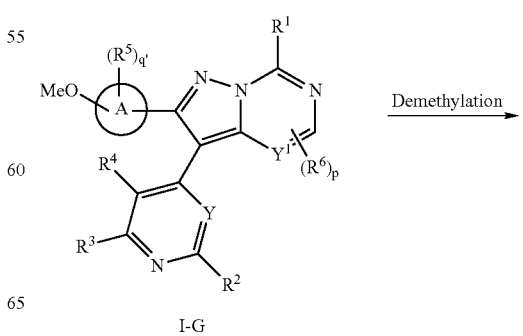

I-G

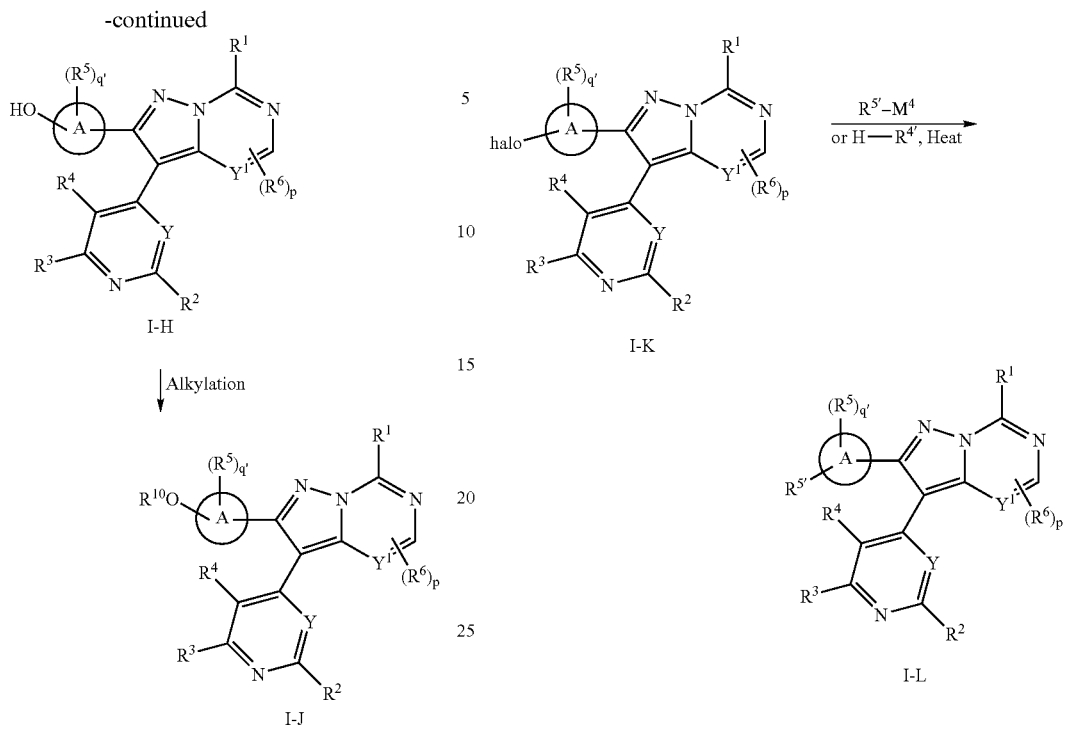

wherein q' is 0, 1, 2, 3 or 4; Me is methyl and all other variables are defined according to any process described above.

The demethylation reaction may be carried out by treating a compound of formula (I-G) in a suitable solvent with a Lewis acid at a temperature of about −78° C. to room temperature, to produce a compound of formula (I-H). Typically the solvent is an inert solvent such as dichloromethane, chloroform, acetonitrile, toluene or the like. The Lewis acid may be boron tribromide, trimethylsilyl iodide or the like.

Optionally, the compound of formula (I-H) may be further converted to a compound of formula (I-J) by an alkylation reaction. The alkylation reaction may be carried out by treating a compound of formula (I-H) in suitable solvent with an alkyl halide of formula $R^{10}$-halo where $R^{10}$ is as defined above, to form another compound of formula (I-J). The reaction is typically carried out in the presence of a base and with optionally heating to about 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

As a further example of methods for converting a compound of formula (I) to another compound of formula (I), a compound of formula (I-K) (i.e., a compound of formula (I) wherein q is 1 or more and at least one $R^5$ is halo) may be converted to a compound of formula (I-L) (i.e., a compound of formula (I) wherein q is 1 or more and at least one $R^5$ is Ay, Het or a nitrogen-linked substituent). for example, the conversion of a compound of formula (I-K) to a compound of formula (I-L) is shown schematically below.

wherein:

q' is 0, 1, 2, 3 or 4;

$R^{5'}$ is selected from the group consisting of Ay, Het, —$NR^7R^8$, —$NR^7$Ay and —NHHet;

$M^4$ is selected from the group consisting of —$B(OH)_2$, —$B(ORa)_2$, —$B(Ra)_2$, and —$Sn(Ra)_2$ wherein Ra is alkyl or cycloalkyl; and all other variables are as defined according to any process described above.

The conversion of a compound of formula (I-K) to a compound of formula (I-L) is carried out by heating a compound of formula (I-K) with a compound of formula H—$R^{5'}$ or coupling the compound of formula (I-K) with a compound of formula $R^{5'}$-$M^4$, where $M^4$ is —$B(OH)_2$, —$B(ORa)_2$, —$B(Ra)_2$, —$Sn(Ra)_2$ wherein Ra is alkyl or cycloalkyl. The reaction may be carried out in an inert solvent, in the presence of a palladium (O) source. The reaction may optionally be heated to about 50–150° C. Preferably the reaction is performed by reacting equimolar amounts of a compound of formula (I-K) with a compound of formula $R^{5'}$-$M^4$. The reaction may also be performed in the presence of an excess $R^{5'}$-$M^4$. The palladium (O) catalyst is typically present in 1–25 mol % compared to the compound of formula (I-K). Examples of suitable palladium catalysts include but are not limited to, tetrakis(triphenylphosphine)palladium (O), dichlorobis(triphenyl-phosphine)palladium(II), and bis(diphenylphosphinoferrocene) palladium (II) dichloride. Suitable solvents include but are not limited to, N,N-dimethylformamide, toluene, tetrahydrofuran, dioxane, and 1-methyl-2-pyrrolidinone. When the compound of formula $R^{5'}$-$M^4$ is a boronic acid or ester or a borinate the reaction is more conveniently carried out by adding a base in a proportion equivalent to, or greater than, that of the compound of formula $R^{5'}$-$M^4$. Compounds of formula $R^{5'}$-$M^4$ may be obtained from commercial sources or prepared either as discreet isolated compounds or generated in situ using methods known to one skilled in the art (Suzuki, A. *J. Organomet. Chem.* 1999, 576, 147; Stille, J. *Angew. Chem. Int. Ed. Engl.* 1986, 25, 508; Snieckus, V. *J. Org. Chem.* 1995, 60, 292.)

In yet another example, a compound of formula (I-K) (i.e., a compound of formula (I) wherein q is 1 or more and at least one $R^5$ is halo) are converted to a compound of formula (I-N) (i.e., a compound of formula (I) wherein q is 1 or more and at least one $R^5$ is $NH_2$). Optionally, a compound of formula (I-N) may then be converted to a compound of formula (I-O) (i.e., a compound of formula (I) wherein q is 1 or more and at least one $R^5$ is —$NR^7R^8$ where $R^7$ and $R^8$ are not both H). For example, the foregoing conversions are represented schematically as follows:

of base, optionally with heating may be used to prepare a compound of formula (I-O). Typically the base is triethylamine or pyridine and the solvent is N,N-dimethylformamide and the like. Other transformations well known to those skilled in the art for use with anilines may be used to convert a compound of formula (I-N) to a compound of formula (I-O).

Additional compounds of formula (I-O) can be obtained by reductive amination of a compound of formula (I-N) with ketones or aldehydes. See, K Abdel-Magid, et al., *J. Org. Chem.* 61:3849–3862 (1996). Typically a compound of formula (I-N) is treated with an aldehyde or a ketone in the

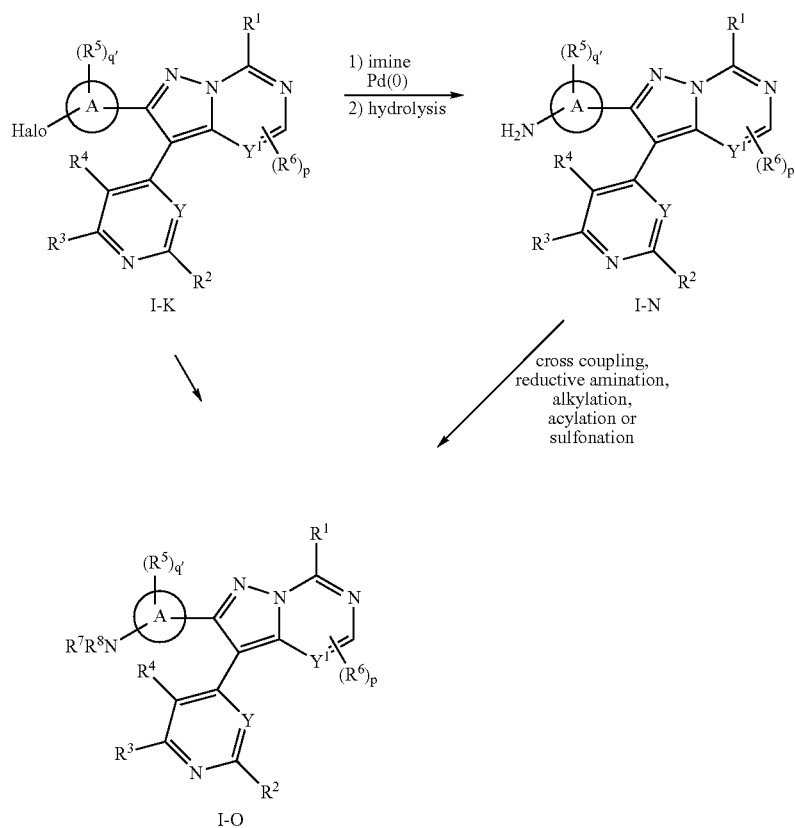

wherein q' is 0, 1, 2, 3 or 4, and all other variables are defined according to any process described above.

The process of converting a compound of formula (I-K) to a compound of formula (I-N) is carried out by reacting a compound of formula (I-K) with an imine in the presence of a palladium (0) source, a base and a suitable ligand, followed by hydrolysis to give a compound of formula (I-N). See J. Wolfe, et al., *Tetrahedron Letters* 38:6367–6370 (1997). Typically the imine is benzophenoneimine, the palladium (O) source is tris(dibenzylideneacetone)dipalladium (O), the base is sodium tert-butoxide and the ligand is racemic-2,2'-bis(diphenylphosphino)-1,1'-binaphthyl. Suitable solvents include N,N-dimethylformamide and the like.

Reaction of a compound of formula (I-N) with compound of formula $R^7$-halogen in a suitable solvent in the presence presence of an acid, such as acetic acid, and a reducing agent, such as sodium triacetoxyborohydride and the like, in an inert solvent such as dichloroethane and the like.

As previously described, another method for converting a compound of formula (I-K) directly to a compound of formula (I-O) involves heating a compound of formula (I-K) with a amine to thermally displace the halogen.

In the embodiment where a compound of formula (I),is defined where $R^1$ is H, the compound of formula (I-P) may be converted to a compound of formula (I-Q). For example, a compound of formula (I-P) may be converted to a compound of formula (I-Q) by a deprotonation/electrophile quench protocol. For example, reaction of a compound of formula (I-P) with a base, such as n-butyllithium, followed by reacting with an electrophilic agent gives a compound of formula (I-Q).

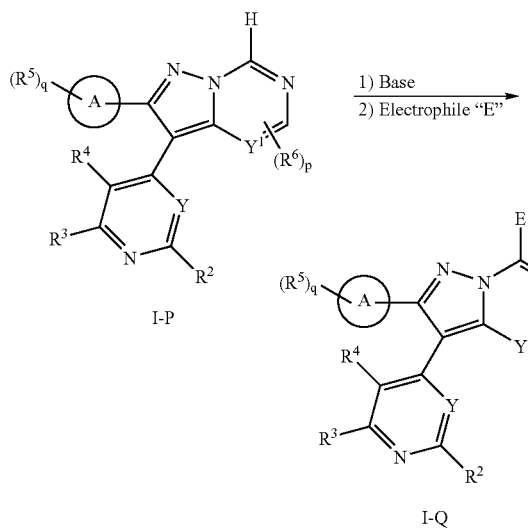

I-P

I-Q

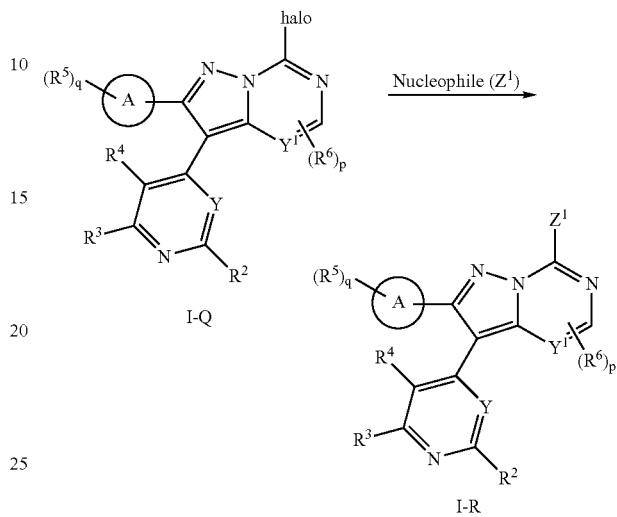

I-Q

I-R wherein E is selected from halo, alkyl, —C(O)R$^9$, —C(O)Ay, —C(O)Het, —CO$_2$R$^9$, —C(O)NR$^7$R$^8$, —C(O)NR$^7$Ay, —S(O)$_n$R$^9$ and —R$^{10}$cycloalkyl, and all other variables are as defined in connection with any processes described above.

Electrophiles which may be used in this process include, but are not limited to: halogens (E=iodo, bromo, chloro), alkyl halides (E=methyl, benzyl etc.); aldehydes (E=CH(OH)R$^{10}$); dimethylformamide (E=CHO); dialkyl disulfide (E=SMe, SEt, S-isopropyl etc); carbon dioxide (E=CO$_2$H); dimethylcarbamoyl chloride (E=C(O)NMe$_2$) and the like.

Typically a compound of formula (I-P) in an inert solvent such as tetrahydrofuran at about −78° C. is treated with a nonnucleophilic base. This reaction is subsequently quenched by addition of an electrophile. Suitable nonnucleophilic bases include, but are not limited to, n-butyl-lithium, lithium diisopropylamide, lithium tetramethylpiperidide and the like.

Further, a compound of formula (I) wherein R$^1$ is H, may be converted to another compound of formula (I), by a deprotonation/electrophile quench/nucleophilic displacement protocol. For example, reaction of a compound of formula (I-P) with a base, such as n-butyllithium, followed by quenching with an electrophilic halogenating agent gives a compound of formula (I-Q where E is halogen) as outlined in the previous scheme. Treatment of a compound of formula (I-Q, where E is halogen) with a nucleophile (Z') in a suitable solvent optionally with heating and optionally in the presence of a base gives a compound of formula (I-R).

wherein Z$^1$ is selected from the group consisting of Het, —OR$^7$, —OAy, —OHet, —NR$^7$R$^8$, —NR$^7$Ay, —NHHet —S(O)$_n$R$^9$ (where n is 0) and cyano and all other variables are as defined according to any process described above.

Solvents for use in this reaction include but are not limited to tetrahydrofuran, diethylether, and 1-methyl-2-pyrrolidinone. The base may be sodium hydride, sodium-tert-butoxide, potassium carbonate or the like.

As another example, one method of converting a compound of formula (I) to another compound of formula (I) comprises a) oxidizing the compound of formula (I-S), where R$^1$ is —SR$^{15}$ and R$^{15}$ is alkyl, cycloalkyl or Ay, to prepare a compound of formula (I-T) and then b) optionally reacting a compound of formula (I-T) with a nucleophile Z$^1$ selected from the group consisting of Het, —OR$^7$, —OAy, —OHet, —NR$^7$R$^8$, —NR$^7$Ay, —NHHet —S(O)$_n$R$^9$ (where n is 0) and cyano, to prepare a compound of formula (I-U).

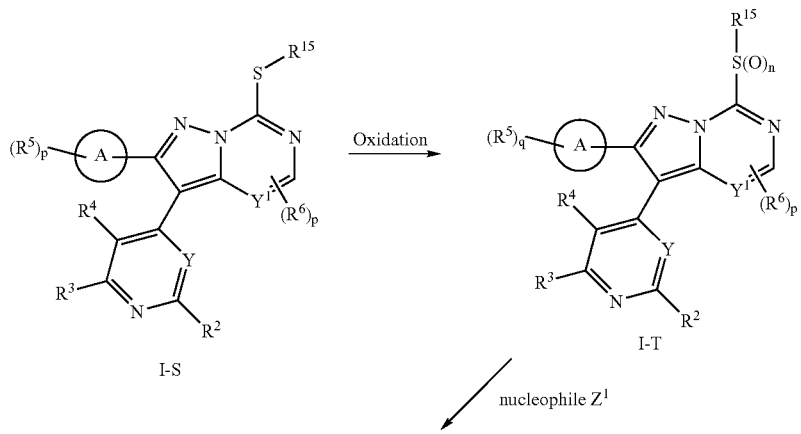

I-S

I-T nucleophile Z$^1$

-continued

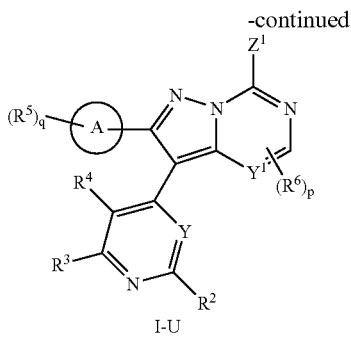

I-U wherein $Z^1$ is selected from the group consisting of Het, —$OR^7$, —OAy, —OHet, —$NR^7R^8$ —$NR^7Ay$, —NHHet —$S(O)_nR^9$(where n is 0) and cyano; $R^{15}$ is alkyl, cycloalkyl or Ay; and all other variables are as defined according to any processes described above.

An analogous method can be used for the conversion of a compound of formula (I) wherein at least one $R^5$ is —$SR^{15}$ to a compound of formula (I) wherein at least one $R^5$ is $Z^1$.

Based upon this disclosure and the examples contained herein one skilled in the art can readily convert compounds of formula (I) or a pharmaceutically acceptable salt, solvate or physiologically functional derivative thereof into other compounds of formula (I), or salts, solvates or physiologically functional derivatives thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated.

The radiolabeled compounds of formula (I) and the biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or a biotinylated compound of formula (I) to the target protein. More specifically, suitable assay methods will include competition binding assays. The radiolabeled compounds of formula (I) and biotinylated compounds of formula (I) can be employed in assays according to the methods conventional in the art.

The following examples are intended for illustration only and are not intended to limit the scope of the invention in any way. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

Example 1

N-Cyclopentyl-3-[2-(cyclopentylamino)pyrimidin-4-yl]-2-(4-fluorophenyl)pyrazolo[1,5-c]pyrimidin-7-amine

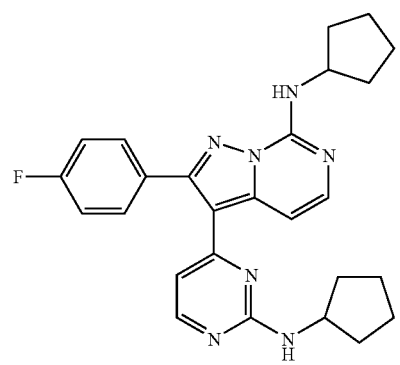

a) 4-Methyl-2-(methylsulfanyl)pyrimidine.

4-Methylpyrimidine-2-thiol (79.4 g. 488 mmol) was added to 1M aqueous sodium hydroxide (NaOH) (1.02 L, 1.02 mol). To the stirring mixture was added iodomethane (76.2 g, 540 mmol) and the reaction-stirred at room temperature overnight. The mixture was extracted with dichloromethane (3×300 mL). The organic phase was dried over magnesium sulfate and concentrated to yield 66.8 g (98%)

of 4-methyl-2-(methylsulfanyl)pyrimidine. $^1$H NMR (CDCl$_3$): δ 8.39 (d, 1H), 6.84 (d, 1H), 2.59 (s, 3H), 2.48 (s, 3H); MS m/z 141 (M+1).

b) 1-(4-Fluorophenyl)-2-[2-(methylsulfanyl)pyrimidin-4-yl]ethanone. To a 0° C. solution of 4methyl-2-(methylsulfanyl)pyrimidine (66.8 g, 477 mmol) and ethyl 4-fluorobenzoate (80.2 g, 477 mmol) in tetrahydrofuran (390 mL) was added a solution of 1M lithium bis(trimethylsilyl)amide (954 mL, 954 mmol) in tetrahydrofuran (THF) dropwise via an addition funnel. The reaction was stirred for 10 minutes and allowed to warm to room temperature. The reaction was stirred at room temperature for 1.5 hours and then carefully quenched with water. The mixture was extracted with ethyl acetate (3×300 mL) before the organic phase was dried over magnesium sulfate, filtered and concentrated. The residue was recrystallized from dichloromethane and hexanes to yield 91.4 g (75%) of 1-(4-fluorophenyl)-2-[2-(methylsulfanyl)pyrimidin-4-yl]ethanone as a mixture of tautomers. Tautomer A: $^1$H NMR (CDCl$_3$): δ 8.50 (d, 1H), 8.12 (dd, 2H), 7.18 (m, 2H), 7.02 (d, 1H), 4.39 (s, 2H), 2.56 (s, 3H). MS m/z263 (M+1). Tautomer B: $^1$H NMR (CDCl$_3$): δ 8.35 (d, 1H), 7.87 (dd, 2H), 7.16 (m, 3H), 6.68 (d, 1H), 5.96 (s, 1H), 2.65 (s, 3H). MS m/z 263 (M+1).

c) 1-(4Fluorophenyl)-2-[2-(methylsulfanyl)pyrimidin-4-yl]ethanone oxime.

To a solution of 1-(4-fluorophenyl)-2-[2-(methylsulfanyl)pyrimidin-4-yl]ethanone (91.49 g,48 mmol) in acetonitrile (1.8 L) was added hydroxylamine hydrochloride (121 g, 91.7 mol) and sodium acetate (139 g, 1.7 mol). The reaction was stirred for 24 hours before 100 mL of water was added. The reaction was stirred for 24 hours. The mixture was filtered through a glass frit and the filtrate partitioned between dichloromethane and water. The layers were separated and the aqueous phase extracted with dichloromethane (2×500 mL). The organic layers were combined, washed with saturated aqueous sodium bicarbonate (300 mL), washed with brine (300 mL), dried over magnesium sulfate, filtered and concentrated. The residue was recrystalized from dichloromethane and hexanes to yield 66.4 g (69%) of 1-(4-fluorophenyl)-2-[2-(methylsulfanyl)pyrimidin-4-yl]ethanone oxime. $^1$H NMR (CDCl$_3$): δ 8.75 (m, 1H), 8.42 (d, 1H), 7.75 (dd, 2H), 7.09 (t, 2H), 6.98 (d, 1H), 4.29 (s, 2H), 2.54 (s, 3H). MS m/z 278 (M+1).

d) 2-(4-Fluorophenyl)-7-(methylsulfanyl)pyrazolo[1,5-c]pyrimidine.

To a 0° C. solution of 1-(4-fluorophenyl)-2-[2-(methylsulfanyl)pyrimidin-4-yl]ethanone oxime(4.0 g, 14 mmol) in ethylene glycol dimethyl ether (40 mL) was added trifluoroacetic anhydride (3.0 g, 14 mmol) dropwise. The reaction was allowed to warm to 20° C., then re-cooled to 0° C. Triethylamine (2.9 g, 29 mmol) was added dropwise so that the internal reaction temperature did not exceed 10° C. The reaction was allowed to warm to room temperature and was stirred for 2 hours. Iron (II) chloride (18 mg, 0.14 mmol) was added and the mixture heated to 80° C. for 2 hours. An additional portion of iron (II) chloride (18 mg, 0.14 mmol) was added and the mixture heated at 80° C. for 2 hours. An additional portion of iron (II) chloride (18 mg, 0.14 mmol) was added and the mixture heated at 80° C. for 4 hours. The reaction was allowed to cool to room temperature and stirred overnight. The mixture was partitioned between ethyl acetate and water. The aqueous phase was extracted with ethyl acetate (2×20 mL) and the organic layers combined. The organic phase was washed with brine, dried over magnesium sulfate, filtered and concentrated. The residue was purified by silica chromatography eluting with 1% acetone in dichloromethane to yield 2.54 g (68%) of 2-(4fluorophenyl)-7-(methylsulfanyl)-pyrazolo[1,5-c]pyrimidine. $^1$H NMR (CDCl$_3$): δ 8.04 (dd, 2H),7.80 (d, 1H), 7.20 (m, 3H), 6.79 (s, 1H), 2.76 (s, 3H). MS m/z 260 (M+1).

e) 1-[2-(4-Fluorophenyl)-7-(methylsulfanyl)pyrazolo[1,5-c]pyrimidin-3-yl]ethanone.

To a solution of 2-(4-fluorophenyl)-7-(methylsulfanyl)pyrazolo[1,5-c]pyrimidine (150 mg, 0.58 mmol) in toluene (10 mL) was added acetic anhydride (0.065 mL, 0.69 mmol), followed by boron trifluoride diethyl etherate (0.080 ml, 0.64 mmol). An additional 10 mL of toluene was added and the mixture heated to 90° C. Acetonitrile (10 mL) was added to the reaction and the mixture heated at 70° C. for additional 16 hours. Additional acetic anhydride (0.11 mL, 1.1 mmol) and boron trifluoride diethyl etherate (0.15 ml, 1.2 mmol) were added dropwise to the reaction mixture at 90° C. The reaction was stirred for 1 hour, cooled to room temperature, stirred for 16 hours, and partitioned between ethyl acetate and saturated aqueous sodium bicarbonate. The ethyl acetate layer was washed with brine, dried over magnesium sulfate, filtered, concentrated, and the residue purified by silica gel chromatography eluting with 10% ethyl acetate in hexanes to yield 110 mg (63%) of 1-[2-(4-fluorophenyl)-7-(methylsulfanyl)pyrazolo[1,5-c]pyrimidin-3-yl]ethanone. $^1$H NMR (CDCl$_3$): δ 8.13 (d, 1H), 7.98 (d, 1H), 7.65 (dd, 2H), 7.27 (m, 2H), 2.77 (s, 3H), 2.23 (s, 3H). MS m/z 302 (M+1).

ee) 1-[2-(4fluorophenyl)-7-(methylsulfanyl)pyrazolo[1,5-c]pyrimidin-3-yl]ethanone.

To a slurry of 2-(4-fluorophenyl)-7-(methylsulfanyl)pyrazolo[1,5-c]pyrimidine (11.8 g, 45.5 mmol) in acetic anhydride (250 mL) was added 10 drops of sulfuric acid (H$_2$SO$_4$). The mixture was heated at reflux for 2 hours. Additional 20 drops of sulfuric acid were added and the reaction heated at reflux for additional 2 hours. The mixture was allowed to cool and was poured into water (300 mL). The mixture was extracted with ethyl acetate (3×200 mL). The organic phase was washed with saturated aqueous sodium bicarbonate and brine, dried over magnesium sulfate, filtered and concentrated. The residual was co-evaporated with toluene and then dissolved in methylene chloride (CH$_2$Cl$_2$). The solution was diluted with hexanes and the resulting precipitate collected by filtration. The solids were dissolved in dichloromethane, passed through a silica plug with 2% acetone in dichloromethane. The wash was concentrated to yield 7.5 g of product The filtrate from the initial filtration was concentrated and the residue purified by silica chromatography, eluting with 2% acetone in dichloromethane to yield additional 1.3 g of product The two portions were combined to yield 8.8 g (64%) of 1-[2-(4fluorophenyl)-7-(methylsulfanyl)pyrazolo[1,5-c]pyrimidin-3-yl]ethanone.

f) 1-[7-(Cyclopentylamino)-2-(4-fluorophenyl)pyrazolo[1,5-c]pyrimidin-3-yl]ethanone.

To a 0° C. solution of 1-[2-(4-fluorophenyl)-7-(methylsulfanyl)pyrazolo[1,5-c]pyrimidin-3-yl]ethanone (400 mg, 1.33 mmol) in dichloromethane (10 mL) was added sodium bicarbonate (110 mg, 1.33 mmol) and 3-chloroperoxybenzoic acid (340 mg, 2.00 mmol). The reaction was allowed to warm to room temperature and stirred for 2 hours. The mix was diluted with dichloromethane and the organic phase was washed with saturated aqueous sodium bicarbonate. The phases were separated and the organic phase concentrated. The residue was dissolved in cyclopentylamine (10 mL) and stirred for 2 hours. The reaction was concentrated and the residue purified by silica gel chromatography eluting with 2% acetone in dichloromethane to give 200 mg (44%) of 1-[7-(cyclopentylamino)-2-(4-fluorophenyl)pyrazolo[1,5-c]pyrimidin-3-yl]ethanone. $^1$H NMR (CDCl$_3$): δ 7.93 (d, 1H), 7.64 (dd, 2H), 7.47 (d, 1H), 7.26 (m, 2H), 6.44 (d, 1H), 4.56 (q, 1H), 2.23 (m, 5H), 1.56–1.90 (m, 6H). MS m/z 339 (M+1).

g) 1-[7-(Cyclopentylamino)-2-(4-fluorophenyl)pyrazolo[1,5-c]pyrimidin-3-yl]-3-(dimethylamino)prop-2-en-1-one.

To 1-[7-(cyclopentylamino)-2-(4fluorophenyl)pyrazolo[1,5- c]pyrimidin-3-yl]ethanone (200 mg, 0.59 mmol) was added 1,1-di-tert-butoxy-N,N-dimethylmethanamine (4 mL) and the mixture heated to 80° C. for 30 minutes. The reaction was let cool to room temperature and was partitioned between ethyl acetate and water. The aqueous layer was extracted with ethyl acetate and the combined organic layers washed with water and brine. The ethyl acetate solution was dried over magnesium sulfate, filtered and concentrated. The resulting residue was purified by silica chromatography eluting with ethyl acetate to yield 160 mg (69%) of 1-[7-(cyclopentylamino)-2-(4-fluorophenyl)pyrazolo[1,5-c]pyrimidin-3-yl]-3-(dimethylamino)prop-2-en-1-one. $^1$H NMR (CDCl$_3$): δ 7.77 (m, 4H), 7.44 (d, 1H), 7.19 (t, 2H), 6.41 (d, 1H), 5.09 (d, 1H), 4.57 (m,1H), 3.07 (m, 3H), 2.60 (m, 3H), 2.25 (m, 2H), 1.85 (m, 6H). MS m/z 394 (M+1).

h) N-Cyclopentyl-3-[2-(cyclopentylamino)pyrimidin-4-yl]-2-(4-fluorophenyl)-pyrazolo[1,5-c]pyrimidin-7-amine.

To a solution of 1-[7-(cyclopentylamino)-2-(4-fluorophenyl)pyrazolo[1,5-c]pyrimidin-3-yl]-3-(dimethylamino) prop-2-en-1-one (160 mg, 0.41 mmol) in N,N-dimethylformamide (10 mL) was added N-cyclopentylguanidine hydrochloride (130 mg, 0.82 mmol). Freshly ground anhydrous potassium carbonate (56 mg, 0.41 mmol) was added and the reaction heated to 140° C. for 4 hours. Additional freshly ground anhydrous potassium carbonate (120 mg, 0.87 mmol) and N-cyclopentylguanidine hydrochloride (75 mg, 0.46 mmol) were added and the reaction heated for additional 3 hours. The reaction was allowed to cool and was stirred at room temperature for 16 hours. The mixture was quenched with water, extracted with ethyl acetate (2×), washed with brine, concentrated, and the residue purified by silica chromatography eluting with 5% acetone in dichloromethane to yield 140 mg (75%) of N-cyclopentyl-3-[2-(cyclopentylamino)pyrimidin-4-yl]-2-(4-fluorophenyl)pyrazolo[1,5-c]pyrimidin-7-amine. $^1$H NMR (CDCl$_3$): δ 8.09 (d, 1H), 7.80 (d, 1H), 7.66 (dd, 2H), 7.54 (d, 1H), 7.19 (t, 2H), 6.42 (d, 1H), 6.30 (d, 1H), 5.14 (d, 1H), 4.57 (m, 1H), 4.34 (m, 1H), 2.22 (m, 2H), 2.09 (m, 2H), 1.52–1.89 (m, 12H).

Example 2

N-Cyclopentyl-3-[2-(cyclopropylamino)pyrimidin-4yl]-2-(4-fluorophenyl)pyrazolo[1,5-c]pyrimidin-7-amine

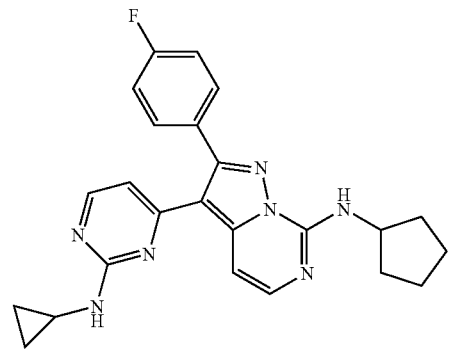

The title compound was prepared in a similar manner as described in Example 1 to give a light yellow solid. $^1$H NMR (CDCl$_3$): δ 8.09 (d, 1H), 7.77 (d, 1H), 7.68–7.61 (m, 3H), 7.17 (t, 2H), 6.38 (d, 1H), 6.33 (d, 1H), 5.43 (broad, 1H), 4.55 (m, 1H), 2.85 (m, 1H), 2.19 (m, 2H), 1.83–1.62 (m, 6 H), 0.87 (m, 2 H), 6.63 (m, 2H); $^{19}$F NMR (CDCl$_3$) δ −112.35; MS m/z 430 (M+1).

Example 3

4-[2-(3-Chlorophenyl)pyrazolo[1,5-c]pyrimidin-3-yl]-N-cyclopentylpyrimidin-2-amine

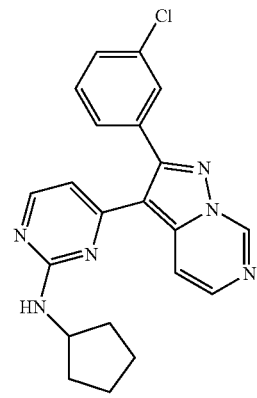

a) 1-(3-Chlorophenyl)-2-(4pyrimidinyl)ethenol.

To a cold (0° C.) solution of 4-methylpyrimidine (4.56 mL 50.1 mmol) and ethyl 3-chlorobenzoate (7.90 mL 50.1 mmol) in tetrahydrofuran (50 mL) was added lithium bis(trimethylsilyl)amide (100 mL, 1.0M in tetrahydrofuran, 100 mmol) dropwise over 30 minutes. The resultant mixture was warmed to room temperature and stirred 16 hours. The reaction mixture was concentrated in vacuo. The resultant oil was diluted with methanol. Upon standing, a solid precipitated, which was collected on a filter to provide 1-(3-chlorophenyl)-2-(4-pyrimidinyl)ethenol (11.2 g, 93%) as a yellow solid. $R_f$ 0.31 (3:1 hexanes:ethyl acetate); $^1$H NMR (d$_6$-DMSO) δ 8.37 (s, 1H), 7.98 (m, 1H), 7.81–7.76 (m, 2H), 7.38–7.32 (m, 2H), 6.71 (br, 1H), 5.65 (s, 1H); MS m/z 233 (M+1).

b) 1-(3-Chlorophenyl)-2-(4-pyrimidinyl)ethanone oxime.

To a suspension of 1-(3-chlorophenyl)-2-(4-pyrimidinyl) ethenol (9.0 g, 38.7 mmol) in methanol (100 mL) was added hydroxylamine hydrochloride (11.5 g, 165 mmol) and sodium hydroxide (60 mL, 2.8 M in water, 166 mmol). The reaction mixture was refluxed 4 hours. After cooling, the excess methanol was removed in vacuo. Ice water (~300 mL) was added to the resultant mixture and the ice was allowed to melt. The aqueous mixture was extracted with ethyl acetate. The organic layer was washed with water and brine, then dried over magnesium sulfate. Filtration and concentration followed by flash chromatography (3:1 to 2:1 hexanes:ethyl acetate) provided 1-(3-chlorophenyl)-2-(4-pyrimidinyl)ethanone oxime (6.5 g, 68%) as a white solid. $R_f$ 0.14 (3:1 hexanes:ethyl acetate): $^1$H NMR (CDCl$_3$) δ 9.50 (br, 1H), 9.18 (s, 1H), 8.61 (d, 1H), 7.78 (s, 1H), 7.58 (d, 1H), 7.38–7.25 (m, 3H), 4.38 (s, 2H); MS m/z 248 (M+1).

c) 2-(3-Chlorophenyl)pyrazolo[1,5-c]pyrimidine.

To a cold (0° C.) solution of 1-(3-chlorophenyl)-2-(4-pyrimidinyl)ethanone oxime (5.0 g, 20.2 mmol) in ethylene glycol dimethyl ether (50 mL) was added trifluoroacetic anhydride (2.85 ml, 20.2 mmol) dropwise. The reaction mixture was warmed to room temperature and stirred 10 minutes then recooled to 0° C. A solution of triethylamine (5.63 mL, 40.4 mmol) in ethylene glycol dimethyl ether was added and the resultant solution was stirred at room temperature 1.5 hours. Iron (II) chloride (25 mg, 0.20 mmol) was added and the reaction mixture was refluxed 3 hours. The reaction mixture was cooled to room temperature and the excess ethylene glycol dimethyl ether was removed in vacuo. The resultant oil was chromatographed (9:1 to 4:1 hexanes:ethyl acetate) to provide 2-(3-chlorophenyl)pyrazolo[1,5-c]pyrimidine (3.2 g, 69%) as a pale yellow solid. $R_f$ 0.27 (4:1 hexanes:ethyl acetate); $^1$H NMR (CDCl$_3$) δ 9.25 (s, 1H), 8.00 (s, 1H), 7.88–7.81 (m, 2H), 7.46–7.39 (m, 3H), 6.81 (s, 1H); MS m/z 230 (M+1).

d) 2-(3-Chlorophenyl)pyrazolo[1,5-c]pyrimidine-3-carbaldehyde.

To a cold (0° C.) solution of phosphorus oxychloride (1.22 mL, 13.1 mmol) in N,N-dimethylformamide (50 mL) was added a solution of 2-(3-chlorophenyl)pyrazolo[1,5-c] pyrimidine (2.00 g, 8.71 mmol) in N,N-dimethylformamide (25 mL). The reaction mixture was stirred at room temperature overnight. To the reaction mixture was added a cold (0° C.) solutions of phosphorus oxychloride (1.22 mL, 13.1 mmol) in N,N-dimethylformamide (50 mL) and the resultant mixture was stirred at room temperature 4 days. The reaction contents were poured onto ice. After the ice had melted, the precipitated solids were collected on a filter to provide 2-(3-chlorophenyl)pyrazolo[1,5c]pyrimidine-3-carbaldehyde (1.5 g, 67%) as a white solid. $^1$H NMR (DMSO-d$_6$) δ 10.11 (s, 1H), 9.86 (s, 1H), 8.37 (d, 1H), 8.22 (d, 1H), 7.99 (s, 1H), 7.91 (d, 1H), 7.70–7.59 (m, 2H); MS m/z 258 (M+1).

e) 1-[2-(3-Chlorophenyl)pyrazolo[1,5-c]pyrimidin-3-yl]-2-propyn-1-ol.

To a solution of 2-(3-chlorophenyl)pyrazolo[1,5-c]pyrimidine-3-carbaldehyde (1.5 g, 5.82 mmol) in tetrahydrofuran (50 mL) was added ethynylmagnesium bromide (17 mL, 0.5 M in tetrahydrofuran, 8.73 mmol). The reaction mixture was stirred 4 hours at room temperature then quenched with water. The mixture was extracted with ethyl acetate. The organic layer was washed with water and brine, then dried over magnesium sulfate. Filtration and concentration followed by flash chromatography (2:1 hexanes:ethyl acetate) provided 1-[2-(3-chlorophenyl)pyrazolo[1.5-c]pyrimidin-3-yl]-2-propyn-1-ol (1.41 g, 85%). $R_f$ 0.17 (2:1 hexanes:ethyl acetate); $^1$H NMR (CDCl$_3$) δ 9.27 (s, 1H), 7.93–7.90 (m, 2H), 7.83 (s, 1H), 7.73 (d, 1H), 7.50–7.41 (m, 2H), 5.78 (s, 1H), 2.99 (br, 1H), 2.71 (s, 1H); MS m/z 284 (M+1).

f) 1-[2-(3-Chlorophenyl)pyrazolo[1,5-c]pyrimidin-3-yl]-2-propyn-1-one.

To a cold (0° C.) solution of 1-[2-(3-chlorophenyl)pyrazolo[1,5-c]pyrimidin-3-yl]-2-propyn-1-ol (1.41 g, 4.97 mmol) in chloroform (600 mL) was added manganese dioxide (30.3 g, 0.348 mol). The reaction mixture was stirred at 0° C. for 10 minutes then filtered through a pad of celite. The filtrate was concentrated in vacuo to provide 1-[2-(3-chlorophenyl)pyrazolo[1,5-c]pyrimidin-3-yl]-2-propyn-1-one (1.40 g, 100%) as a white solid. $R_f$ 0.37 (2:1 hexanes:ethyl acetate); $^1$H NMR (CDCl$_3$) δ 9.39 (s, 1H), 8.37 (d, 1H), 8.28 (d, 1H), 7.78 (s, 1H), 7.62 (d.1H), 7.52–7.40 (m, 2H), 3.17 (s, 1H); MS m/z 282 (M+1).

g) 4-[2-(3-Chlorophenyl)pyrazolo[1,5-c]pyrimidin-3-yl]-N-cyclopentyl pyrimidin-2-amine.

To a mixture of cyclopentyl guanidine hydrochloride (1.05g, 6.43 mmol) in ethanol (60 mL) was added sodium ethoxide (2.15 mL, 3 M in ethanol, 6.43 mmol). The mixture was stirred at room temperature for 30 minutes then cooled to 0° C. A solution of 1-[2-(3-chlorophenyl)pyrazolo[1,5-c] pyrimidin-3-yl]-2-propyn-1-one (1.4 g, 4.97 mmol) in ethanol (100 mL) was added and the reaction mixture was stirred at room temperature 16 hours. The reaction mixture was diluted with water (200 mL) then concentrated to about two thirds the original volume. The precipitated solids were collected on a filter to provide 4-[2-(3-Chlorophenyl)pyrazolo[1,5-c]pyrimidin-3-yl]-N-cyclopentylpyrimidin-2-amine (1.25 g, 64%) as a white solid. $R_f$ 0.19 (4:1 hexanes:ethyl acetate); $^1$H NMR (CDCl$_3$) δ9.32 (s,1H), 8.22 (d,1H), 8.13 (d, 1H), 8.01 (d, 1H), 7.72 (s,1H), 7.55–7.39 (m, 3H), 6.38 (d,1H), 5.19 (d, 1H), 4.33 (m, 1H), 2.08 (m, 2H), 1.80–1.52 (m, 6H); MS m/z 391 (M+1).

Example 4

4-[2-(3-Chlorophenyl)-7-(methylthio)pyrazolo[1,5-c]pyrimidin-3-yl]-N-cyclopentylpyrimidin-2-amine

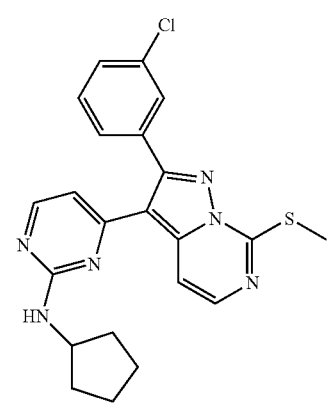

To a cold (−78° C.) solution of 4-[2-(3-chlorophenyl) pyrazolo[1,5-c]pyrimidin-3-yl]-N-cyclopentyl-2-pyrimidinamine (267 mg, 0.683 mmol) in tetrahydrofuran (8 mL) was added lithium diisopropylamide (12.8 mL, 0.16 M in tetrahydrofuran, 2.05 mmol, made from 5 mL n—BuLi (1.6 M in hexanes) and 1.19 mL diisopropylamine in 43.5 mL tetrahydrofuran at 0° C.) dropwise. The reaction mixture was stirred at −78° C. for 10 minutes followed by the addition of methyl disulfide (246 μL, 2.73 mmol). The resultant mixture was stirred at −78° C. for 10 minutes then quenched with water. Upon warming to room temperature, the mixture was extracted with ethyl acetate. The organic layer was washed with water and brine, then dried over magnesium sulfate. Filtration and concentration followed by flash chromatography (4:1 to 3:1 hexanes:ethyl acetate) provided 4-[2-(3-chlorophenyl)-7-(methylthio)pyrazolo[1,5-c]pyrimidin-3-yl]-N-cyclopentylpyrimidin-2-amine (171 mg, 57%) as a white solid. $R_f$ 0:10 (4:1 hexanes:ethyl acetate); $^1$H NMR (CDCl$_3$) δ 8.12 (d, 1H), 7.99–7.91 (m, 2H), 7.73 (s,1H), 7.51 (d, 1H), 7.48–7.34 (m, 2H), 6.35 (d,1H), 5.19 (d, 1H), 4.30 (m, 1H), 2.76 (s, 3H), 2.05 (m, 2H), 1.82–1.50 (m, 6H); MS m/z 437 (M+1).

Example 5

2-(3-Chlorophenyl)-N-cyclopentyl-3-[2-(cyclopentylamino)-4-pyrimidinyl]pyrazolo[1,5-c]pyrimidin-7-amine

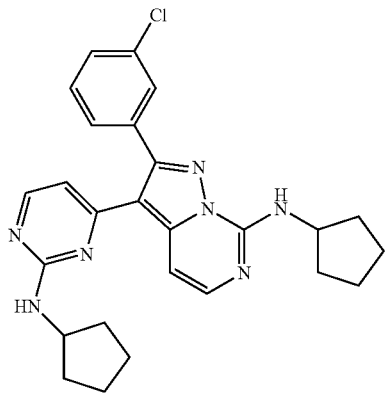

To a cold (0° C.) solution of 4-[2-(3-chlorophenyl)-7-(methylthio)pyrazolo[1,5-c]pyrimidin-3-yl]-N-cyclopentylpyrimidin-2-amine (40 mg, 0.0915 mmol) in dichloromethane (3 mL) was added m-chloroperoxybenzoic acid (24 mg, 0.139 mmol). The reaction mixture was stirred 1.5 hours at 0° C. then diluted with dichloromethane and washed with saturated aqueous sodium bicarbonate solution. The organic layer was washed with water and brine, then dried over magnesium sulfate. Filtration and concentration provided a crude oil which was heated in cyclopentylamine (2 mL, 20 mmol) at 85° C. in a sealed tube for 16 hours. The reaction mixture was diluted with ethyl acetate and washed with saturated aqueous sodium bicarbonate solution. The organic layer was washed with brine and dried over magnesium sulfate. Filtration and concentration followed by flash chromatography (4:1 to 3:1 hexanes:ethyl acetate) provided 2-(3-chlorophenyl)-N-cyclopentyl-3-[2-(cyclopentylamino)-4-pyrimidinyl]pyrazolo[1,5-c]pyrimidin-7-amine (28 mg, 65%) as a beige solid. $R_f$ 0.27 (3:1 hexanes: ethyl acetate); $^1$H NMR (CDCl$_3$) δ 8.09 (d, 1H), 7.78 (d, 1H), 7.71 (s, 1H), 7.51–7.35 (m, 4H), 6.41 (d, 1H), 6.30 (d, 1H), 5.15 (d, 1H), 4.53 (m, 1H), 4.29 (m, 1H), 2.20 (m, 2H), 2.04 (m, 2H), 1.83–1.50 (m, 12 H); MS m/z 474 (M+1).

Example 6

4-[2-(3-Chlorophenyl)-7-(4-morpholinyl)pyrazolo[1,5-c]pyrimidin-3-yl]-N-cyclopentyl-2-pyrimidinamine

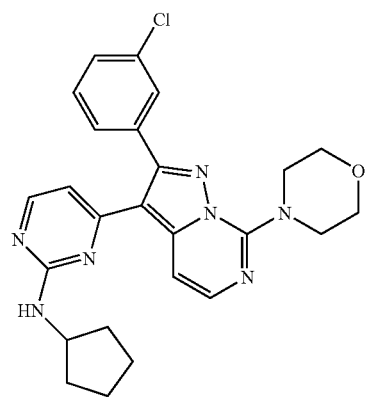

In a similar manner as described in Example 5 from 4-[2-(3-chlorophenyl)-7-(methylthio)pyrazolo[1,5-c]pyrimidin-3-yl]-N-cyclopentylpyrimidin-2-amine (40 mg, 0.091 mmol), 4-[2-(3-chlorophenyl)-7-(4-morpholinyl)pyrazolo[1,5-c]pyrimidin-3-yl]-N-cyclopentyl-2-pyrimidinamine (29 mg, 67%) was obtained as a yellow solid. $R_f$ 0.18 (2:1 hexanes:ethyl acetate); $^1$H NMR (CDCl$_3$) δ 8.10 (d, 1H), 7.78–7.73 (m, 2H), 7.68 (t, 1H), 7.52–7.37 (m, 3H), 6.32 (d, 1H), 5.19 (d, 1H), 4.30 (m, 1H), 4.04 (m, 4H), 3.93 (m, 4H), 2.05 (m, 2H), 1.79–1.50 (m, 6H); MS m/z 476 (M+1).

Example 7

2-(3-Chlorophenyl)-3-[2-(cyclopentylamino)-4-pyrimidinyl]-N-(2-methoxyethyl)pyrazolo[1,5-c]pyrimidin-7-amine

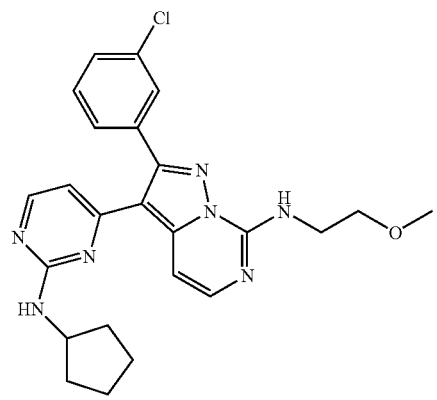

In a similar manner as described in Example 5 from 4-[2-(3-chlorophenyl)-7-(methylthio)pyrazolo[1,5-c]pyrimidin-3-yl]-N-cyclopentylpyrimidin-2-amine (40 mg, 0.091 mmol), 2-(3-chlorophenyl)-3-[2-(cyclopentylamino)-4-pyrimidinyl]-N-(2-methoxyethyl)pyrazolo[1,5-c]pyrimidin-7-amine (22 mg, 52%) was obtained as a white solid. R$_f$ 0.05 (3:1 hexanes:ethyl acetate); $^1$H NMR (CDCl$_3$) δ 8.09 (d, 1H), 7.76–7.69 (m, 2H), 7.52–7.36 (m, 4H), 6.74 (t, 1H), 6.32 (d, 1H), 5.13 (d, 1H), 4.29 (m,1H), 3.87 (m, 2H), 3.68 (t, 2H), 3.43 (s, 3H), 2.05 (m, 2H), 1.79–1.48 (m, 6H); MS m/z 464 (M+1).

Example 8

2-(3-Chlorophenyl)-3-[2-(cyclopentylamino)-4-pyrimidinyl]pyrazolo[1,5-c]pyrimidin-7-ol

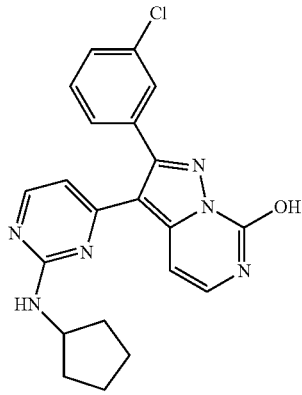

To a cold (0° C.) solution of 4-[2-(3-chlorophenyl)-7-(methylthio)pyrazolo[1,5-c]pyrimidin-3-yl]-N-cyclopentylpyrimidin-2-amine (90 mg, 0.206 mmol) in dichloromethane (10 mL) was added m-chloroperoxybenzoic acid (54 mg, 0.313 mmol). The reaction mixture was stirred 1.5 hours at 0° C. then diluted with dichloromethane and washed with saturated aqueous sodium bicarbonate. The organic layer was washed with water and brine, then dried over magnesium sulfate. Filtration and concentration provided a crude oil. In a separate flask, a solution of sodium butoxide was prepared by reacting sodium (35 mg, 1.52 mmol) with n-butanol (2 mL). The sodium butoxide solution was added to the crude oil and the resulting solution was heated in a sealed tube at 120° C. for 16 hours. The reaction mixture was cooled and concentrated in vacuo. The resulting oil was partitioned between water and ethyl acetate. The organic layer was washed with water and brine, then dried over magnesium sulfate. Filtration and concentration provided a crude oil which was diluted with ethyl acetate (~5 mL). Upon standing 7 hours, a solid had precipitated, which was collected on a filter to provide 2-(3-chlorophenyl)-3-[2-(cyclopentylamino)-4-pyrimidinyl]pyrazolo[1,5-c]pyrimidin-7-ol (22 mg, 26%) as a pale yellow solid. $^1$H NMR (CDCl$_3$) δ 8.00 (d, 1H), 7.60 (s, 1H), 7.42 (d, 1H), 7.36 (d, 1H), 7.30 (d, 1H), 7.25 (s, 1H), 7.14 (d, 1H), 7.02 (d, 1H), 6.24 (d, 1H), 4.19 (m, 1H), 1.99 (m, 2H), 1.78–1.42 (m, 6H); MS m/z 407 (M+1).

Example 9

N-Cyclopentyl-8-(2-fluoro-4-pyridinyl)-2-(methylsulfanyl)-7-phenylpyrazolo[1,5-a][1,3,5]triazin-4-amine

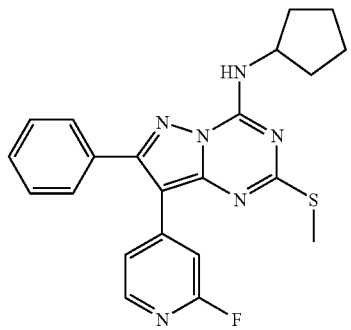

a) Ethyl [(3-phenyl-1H-pyrazol-5-yl)amino]carbothioylcarbamate.

To a cold (0° C.) solution of 3-amino-5-phenylpyrazole (10.0 g, 62.8 mmol) in toluene (100 mL) was added ethoxycarbonyl isothiocyanate (8.3 mL, 70 mmol) dropwise via a pressure equalizing funnel. Upon complete addition, the cold bath was removed and the resulting solution was stirred at room temperature for 15hours, at which time a heavy white precipitate had formed. The precipitate was collected by filtration and dried to give ethyl [(3-phenyl-1H-pyrazol-5-yl)amino]carbothioylcarbamate (11 g, 60%) as a white solid. $^1$H-NMR (DMSO-d$_6$): δ 13.25 (s, 1H), 12.06 (s, 1H), 11.40 (s, 1H), 7.75 (d, 2H), 7.5–7.3 (m, 4H), 4.25 (q, 2H), 1.29 (t, 3H); MS m/z 291 (M+1).

b) 7-Phenyl-2-thioxo-2,3-dihydropyrazolo[1,5-a][1,3,5]triazin-4(1H)-one.

Ethyl [(3-phenyl-1H-pyrazol-5-yl)amino]carbothioylcarbamate (8.4 g, 29 mmol) was dissolved in aqueous sodium hydroxide (100 mL, 2N solution) and the resulting solution was stirred at room temperature overnight. This solution was acidified to pH=1 with concentrated sulfuric acid, resulting in heavy precipitation. This precipitate was collected by filtration and dried to give 7-phenyl-2-thioxo-2,3-dihydropyrazolo-[1,5-a][1,3,5]triazin-4(1H)-one (5.7 g, 80%) as a white solid. $^1$H-NMR (DMSO-d$_6$): δ 7.97 (m, 2H), 7.48 (m, 3H), 6.41 (s, 1H); MS m/z 245 (M+1).

c) 2-(Methylsulfanyl)-7-phenylpyrazolo[1,5-a][1,3,5]triazin-4(3H)-one.

7-Phenyl-2-thioxo-2,3-dihydropyrazolo[1,5-a][1,3,5]triazin-4(1H-one (6.4 g, 26.2 mmol) was dissolved in absolute ethanol (150 mL). To this solution was added aqueous sodium hydroxide (2.1 g, 53 mmol in 50 mL of water) and finally iodomethane (1.7 mL, 27.3 mmol) was added dropwise. The resulting solution was stirred at room temperature for 3 hours and then concentrated to a white solid. This solid was suspended in water and the mixture acidified (to pH=1) with concentrated sulfuric acid. The resulting precipitate was collected by filtration, washed with water and dried to give 2-(methylsulfanyl)-7-phenylpyrazolo[1,5-a][1,3,5]triazin-4(3H)-one (5.5 g, 81%) as a white solid. $^1$H-NMR (DMSO-d$_6$): δ 7.99 (d, 2H), 7.5 (m, 3H), 6.93 (s, 1H), 2.58 (s, 3H); MS m/z 259 (M+1).

d) 4-Chloro-2-(methylsulfanyl)-7-phenylpyrazolo[1,5-a][1,3,5]triazine.

2-(Methylsulfanyl)-7-phenylpyrazolo[1,5-a][1,3,5]triazin-4(3H)-one (5.4 g, 21 mmol) was added to a mixture of phosphorous oxychloride (100 mL) and diethylaniline (2.5 mL). The resulting mixture was heated at reflux for 3 hours. The excess phosphorous oxychloride was removed in vacuo and the dark syrup residue was added slowly to crushed ice with good stirring. Dichloromethane and water were added and the phases separated. The organic phase was washed with water and brine, dried over magnesium sulfate, filtered and concentrated to give a crude solid (5 g, 86%). A portion of this solid was purified by silica gel chromatography (ethyl acetate:hexane 1:1) go give a white solid. $^1$H-NMR (CDCl$_3$): δ 8.04 (m, 2H), 7.54 (m, 3H), 6.83 (s, 1H), 2.66 (s, 3H); MS m/z 277 (M+1).

e) N-Cyclopentyl-2-(methylsulfanyl)-7-phenylpyrazolo[1,5-a][1,3,5]triazin-4-amine.

4-Chloro-2-(methylsulfanyl)-7-phenylpyrazolo[1,5-a][1,3,5]triazine (2.5 g, 9 mmol) was dissolved in cyclopentylamine (30 mL) and the resulting solution heated to 80° C. for 2 hours. Excess cyclopentylamine was removed in vacuo and the residue was dissolved in ethyl acetate. The organic phase was washed with water and brine, dried over magnesium sulfate, filtered and concentrated to give a foam. This foam was purified by silica gel chromatography (ethyl acetate:hexane 1:1) go give 2.3 g (78%) of N-cyclopentyl-2-(methylsulfanyl)-7-phenylpyrazolo[1,5-a][1,3,5]triazin-4amine as a solid. $^1$H-NMR (CDCl$_3$): δ 7.96 (m, 2H), 7.47 (m, 3H), 6.63 (d, 1H), 6.56 (s,1H), 4.54 (m, 1H), 2.61 (s, 3H), 2.2–2.0 (m, 2H), 1.9–1.5 (m, 6H); MS m/z 326 (M+1).

f) 8—Bromo-N-cyclopentyl-2-(methylsulfanyl)-7-phenylpyrazolo[1,5-a][1,3,5]triazin-4-amine.

N-Cyclopentyl-2-(methylsulfanyl)-7-phenylpyrazolo[1,5-a][1,3,5]triazin-4-amine (0.49 g, 1.5 mmol) was dissolved in dichloromethane. To this solution was added N-bromosuccinimide (330 mg, 1.85 mmol) and the resulting solution was stirred at room temperature for 30 minutes. Additional dichloromethane was added and the reaction mixture was extracted with 1N aqueous sodium hydroxide and with water. The organic phase was dried (magnesium sulfate), filtered and concentrated to give a solid. This solid was purified by silica gel chromatography (ethyl acetate:hexane 1:2) to give 0.5 g (82%) of 8-bromo-N-cyclopentyl-2-(methylsulfanyl)-7-phenylpyrazolo[1,5-a][1,3,5]triazin-4-amine as a solid. $^1$H-NMR (CDCl$_3$): δ 8.05 (m,2H), 7.55 (m,3H), 6.52 (d, 1H), 4.60 (m,1H), 2.66 (s, 3H), 2.3–2.1 (m, 2H), 2.0–1.6 (m, 6H); MS m/z 405 (M+1).

g) N-Cyclopentyl-8-(2-fluoro-4-pyridinyl)-2-(methylsulfanyl)-7-phenylpyrazolo[1,5-a][1,3,5]triazin-4-amine.

8—Bromo-N-cyclopentyl-2-(methylsulfanyl)-7-phenylpyrazolo[1,5-a][1,3,5]triazin-4-amine (0.20 g, 0.50 mmol) was dissolved in N,N-dimthylformamide. To this solution was added dichlorobis(triphenylphosphine)palladium (II) (70 mg, 0.2 equiv), anhydrous sodium carbonate (105 mg, 2 equiv), 2-fluoro-4-pyridinylboronic acid (91 mg, 1.3 equiv) and a few drops of water. The reaction mixture was heated at 100° C. for 12 hours, at which time no starting material remained in the reaction mixture. Ethyl acetate and water were added to the reaction mixture. The phases were separated and the organic phase was washed with water, dried over magnesium sulfate, filtered and concentrated. Purification by silica gel chromatography (ethyl acetate: hexane 1:1) gave 70 mg (33%) of N-cyclopentyl-8-(2-fluoro-4pyridinyl)-2-(methylsulfanyl)-7-phenylpyrazolo[1,5-a][1,3,5]triazin-4-amine as a white foam. $^1$H-NMR (CDCl$_3$): δ 8.10 (d, 1H), 7.60 (m, 2H), 7.52 (m, 3H), 7.37 (m, 1H), 7.29 (s, 1H), 6.55 (d, 1H), 4.63 (m, 1H), 2.66 (s, 3H), 2.3–2.1 (m, 2H), 2.0–1.6 (m, 6H);F-NMR (CDCl$_3$): δ −69.01; MS m/z 421 (M+1).

Example 10

N$^2$,N$^4$-Dicyclopentyl-8-[2-(cyclopentylamino)-4-pyridinyl]-7-phenylpyrazolo[1,5-a][1,3,5]triazine-2,4-diamine

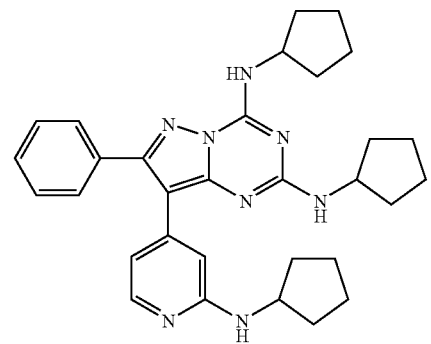

N-Cyclopentyl-8-(2-fluoro-4-pyridiny)-2-(methylsulfanyl)-7-phenylpyrazolo[1,5-a][1,3,5]triazin -4amine 60 mg, 0.14 mmol) was dissolved in cyclopentylamine and heated at 160° C. in a glass pressure vessel for 24 hours. The resulting solution was concentrated in vacuo to give a residue that was purified by silica gel chromatography (ethyl acetate:hexane 1:1 to ethyl acetate) to yield 25 mg (34%) of N$^2$,N$^4$-dicyclopentyl-8-[2-(cyclopentylamino)-4-pyridinyl]-7-phenylpyrazolo[1,5-a][1,3,5]triazine-2,4-diamine as a foam. $^1$H-NMR (CDCl$_3$): δ 7.94 (d, 1H), 7.60 (m, 2H), 7.45 (m, 3H), 6.81 (d, 1H), 6.36 (m, 1H), 5.13 (d, 1H), 4.60 (m, 1H), 4.44 (m, 2H), 3.74 (m, 1H), 2.1–1.4 (m, 24H); MS m/z 523 (M+1).

Example 11

N-Cyclopentyl-8-[2-(cyclopentylamino)-4-pyrimidinyl]-7-phenylpyrazolo[1,5-a][1,3,5]triazin-4-amine

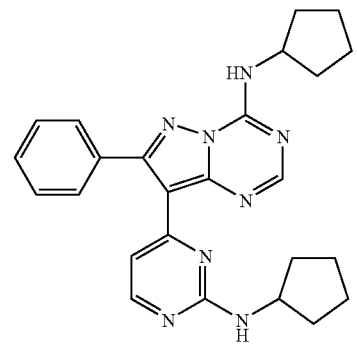

a) N-Cyclopentyl-7-phenylpyrazolo[1,5-a][1,3,5]triazin-4-amine.

N-Cyclopentyl-2-(methylsulfanyl)-7-phenylpyrazolo[1,5-a][1,3,5]triazin-4-amine (300 mg, 0.92 mmol, from Example 9) was dissolved in absolute ethanol (30 mL). To this mixture was added Raney nickel (approximately 2–3 g) and the reaction was heated at reflux for 6 hours. The Raney nickel was removed by filtering the reaction mixture through a Celite pad, and the Celite was washed with ethanol (150 mL). The combined organic phase was concentrated to dryness. The resulting residue was purified by silica gel chromatography (ethyl acetate:hexane 1:1) to give 200 mg (78%) of N-cyclopentyl-7-phenylpyrazolo[1,5-a][1,3,5]triazin-4-amine as a yellow foam. $^1$H-NMR (CDCl$_3$): δ 8.24 (s, 1H), 7.98 (m, 2H), 7.51 (m, 3H), 6.75 (s, 1H), 6.67 (d, 1H), 4.60 (m, 1H), 2.3–2.1 (m, 2H), 2.0–1.6 (m, 6H); MS m/z 280 (M+1).

b) N—Cyclopentyl-8-iodo-7-phenylpyrazolo[1,5-a][1,3,5]triazin-4amine.

N-Cyclopentyl-7-phenylpyrazolo[1,5-a][1,3,5]triazin-4amine (0.25 g, 0.90 mmol) was dissolved in dichloromethane. To this solution was added N-iodosuccinimide (300 mg, 1.33 mmol) and the resulting solution was stirred at room temperature for 30 minutes. Additional dichloromethane was added and the reaction mixture was extracted with 1N aqueous sodium hydroxide and with water. The organic phase was dried (magnesium sulfate), filtered and concentrated to give a solid. This solid was purified by silica gel chromatography (ethyl acetate:hexane 1:1) to give 310 mg (85%) of N-cyclopentyl-8-iodo-7-phenylpyrazolo[1,5-a][1,3,5]triazin-4-amine as a yellow solid. $^1$H-NMR (CDCl$_3$): δ 8.35 (s, 1H), 7.98 (m, 2H), 7.55 (m, 3H), 6.64 (d, 1H), 4.60 (m, 1H), 2.3–2.1 (m, 2H), 2.0–1.6 (m, 6H); MS m/z 406 (M+1).

c) N-Cyclopentyl-8-[2-(cyclopentylamino)-4-pyrimidinyl]-7-phenylpyrazolo[1,5-a][1,3,5]triazin-4-amine.

N-Cyclopentyl-8-iodo-7-phenylpyrazolo[1,5-a][1,3,5]triazin-4-amine (80 mg, 0.20 mmol) was dissolved in anhydrous toluene (5 mL). To this solution was added 2-(methylsulfanyl)-4-(tributylstannyl)pyrimidine (100 mg, 0.24 mmol,) and dichlorobis(triphenylphosphine)palladium (II) (14 mg, 0.1 equiv) and the resulting mixture heated at 100° C. for 24 hours. Ethyl acetate and water were added to the reaction mixture. The phases were separated and the organic phase washed with water, dried over magnesium sulfate, filtered and concentrated. Purification by silica gel chromatography (ethyl acetate:hexane 1:1) gave an inseparable mixture of the desired N-cyclopentyl-8-[2-(methylsulfanyl)-4-pyrimidinyl]-7-phenylpyrazolo[1,5-a][1,3,5]triazin-4-amine contaminated with N-cyclopentyl-7-phenylpyrazolo[1,5-a][1,3,5]triazin-4-amine. This mixture was dissolved in dichloromethane (15 mL) and 3-chloroperoxybenzoic acid (113 mg, 57–86%) was added. The resulting reaction mixture was stirred at room temperature for 1 hour. Dichloromethane and saturated aqueous potassium carbonate were added and the phases separated. The organic phase was washed with additional saturated aqueous potassium carbonate, water, dried over magnesium sulfate, filtered and concentrated to give a foam. This foam was dissolved in cyclopentylamine and the solution was heated at 60° C. for 3 hours. The mixture was concentrated in vacuo and the residue purified by silica gel chromatography (ethyl acetate: hexane 1:1) to give 20 mg (23% for 3 steps) of N-cyclopentyl-8-[2-(cyclopentylamino)-4-pyrimidinyl]-7-phenylpyrazolo[1,5-a][1,3,5]triazin-4-amine as a white foam. $^1$H-NMR (CDCl$_3$): δ 8.39 (s, 1H), 8.28 (d, 1H), 7.67 (m, 2H), 7.46 (3H), 6.71 (d, 1H), 5.01 (d, 1H), 4.64 (m, 1H), 3.80 (m, 1H), 1.2–2.3 (m, 16H); MS m/z 441 (M+1).

Example 12

3-[2-(Butylamino)pyrimidin-4-yl]-N-cyclopentyl-2-(4-fluorophenyl)pyrazolo[1,5-c]pyrimidin-7-amine

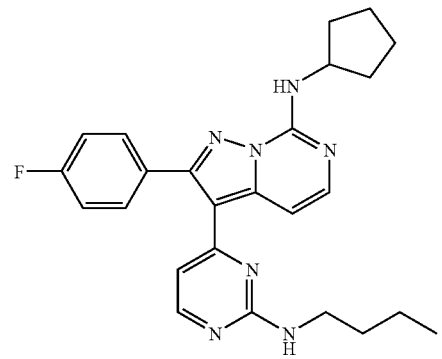

In a similar manner as described in Example 1 above, 3-[2-(butylamino)pyrimidin-4-yl]-N-cyclopentyl-2-(4-fluorophenyl)pyrazolo[1,5-c]pyrimidin-7-amine (80 mg, 72%) was prepared from 1-[7-(cyclopentylamino)-2-(4-fluorophenyl)pyrazolo[1,5-c]pyrimidin-3-yl]-3-(dimethylamino)prop-2-en-1-one and N-butylguanidine. $^1$H NMR (CDCl$_3$): δ 8.04 (d, 1H), 7.74 (d, 1H), 7.60 (dd, 2H), 7.48 (d, 1H), 7.13 (t, 2H), 6.36 (d, 1H), 6.25 (d, 1H), 5.05 (t, 1H), 4.51 (m, 1H), 3.42 (qt, 2H), 2.16 (m, 2H), 1.78 (m, 2H), 1.56–1.70 (m, 6H), 1.43 (m, 2H), 0.95 (t, 3H). MS m/z 446 (M+1).

Example 13

3-(2-Anilinopyrimidin-4-yl)-N-cyclopentyl-2-(4-fluorophenyl)pyrazolo-[1,5-c]pyrimidin-7-amine

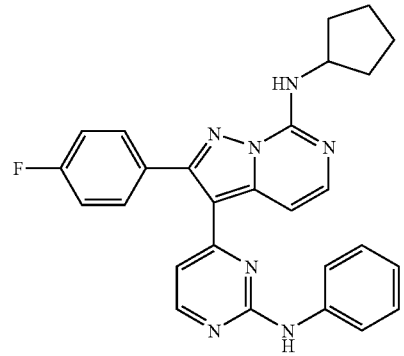

In a similar manner as described above, 3-(2-anilinopyrimidin-4-yl)-N-cyclopentyl-2-(4-fluorophenyl)pyrazolo[1,5-c]pyrimidin-7-amine (70 mg, 60%) was prepared from 1-[7-(cyclopentylamino)-2-(4-fluorophenyl)pyrazolo[1,5-c]pyrimidin-3-yl]-3-(dimethylamino)prop-2-en-1-one and N-cyclopentylguanidine. $^1$H NMR (CDCl$_3$): δ 8.19 (d, 1H), 7.72 (d, 1H), 7.62 (dd, 2H), 7.57 (dd, 2H), 7.44 (d, 1H), 7.30 (t, 2H), 7.15 (t, 2H), 7.08 (s, 1H), 7.03 (t, 1H), 6.47 (d, 1H), 6.38 (d, 1H), 4.52 (m, 1H), 2.12–2.24 (m, 2H), 1.79 (m, 2H), 1.60–1.72 (m, 4H). MS m/z 466 (M+1).

Example 14

3-[2-(1,3-Benzothiazol-2-ylamino)pyrimidin-4-yl]-N-cyclopentyl-2-(4-fluorophenyl)pyrazolo[1,5-c]pyrimidin-7-amine

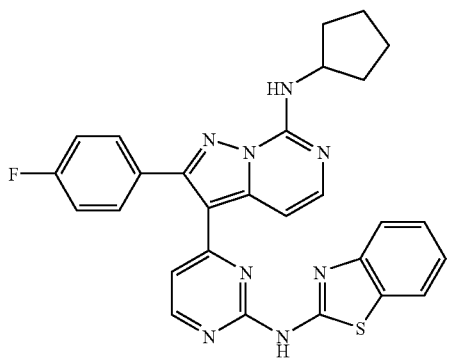

In a similar manner as described above, 3-[2-(1,3-benzothiazol-2-ylamino)pyrimidin-4-yl]-N-cyclopentyl-2-(4-fluorophenyl)pyrazolo[1,5-c]pyrimidin-7-amine (38 mg, 29%) was prepared from 1-[7-(cyclopentylamino)-2-(4-fluorophenyl)pyrazolo[1,5-c]pyrimidin-3-yl]-3-(dimethylamino)prop-2-en-1-one and N-(1,3-benzothiazol-2-yl)guanidine. $^1$H NMR (CDCl3): δ 10.58 (bs, 1H), 8.49 (d, 1H), 7.90 (d, 1H), 7.75 (d, 1H), 7.73 (d, 1H), 7.64 (dd, 2H), 7.47 (d, 1H), 7.40 (t, 1H), 7.23 (t, 1H), 7.15 (t, 2H), 6.69 (d, 1H), 6.41 (d, 1H), 4.54 (m, 1H), 2.14–2.24 (m, 2H), 1.58–1.85 (m, 6H). MS m/z 523 (M+1).

Example 15

N-Cyclopentyl-2-(4-fluorophenyl)-3-{2-[(4-methyl-1,3-thiazol-2-yl)amino]pyrimidin-4-yl}pyrazolo[1,5-c]pyrimidin-7-amine

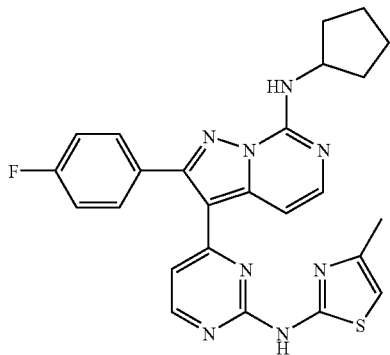

In a similar manner as described above, N-cyclopentyl-2-(4-fluorophenyl)-3-{2-[(4-methyl-1,3-thiazol-2-yl)amino]pyrimidin-4-yl}pyrazolo[1,5-c]pyrimidin-7-amine (65 mg, 53%) was prepared from 1-[7-(cyclopentylamino)-2-(4-fluorophenyl)pyrazolo[1,5-c]pyrimidin-3-yl]-3-(dimethylamino)prop-2-en-1-one and N-(4-methyl-1,3-thiazol-2-yl)guanidine. $^1$H NMR (CDCl3): δ 9.16 (s, 1H), 8.33 (d, 1H), 7.76 (d, 1H), 7.61 (dd, 2H), 7.45 (d, 1H), 7.14 (t, 2H), 6.58 (d, 1H), 6.40 (s, 1H), 6.39 (d, 1H), 4.53 (m, 1H), 2.35, (s, 3H), 2.13–2.24 (m, 2H), 1.60–1.84 (m, 6H). MS m/z 487 (M+1).

Example 16

3-[2-(1H-Benzimidazol-2-ylamino)pyrimidin-4-yl]-N-cyclopentyl-2-(4-fluorophenyl)pyrazolo[1,5-c]pyrimidin-7-amine

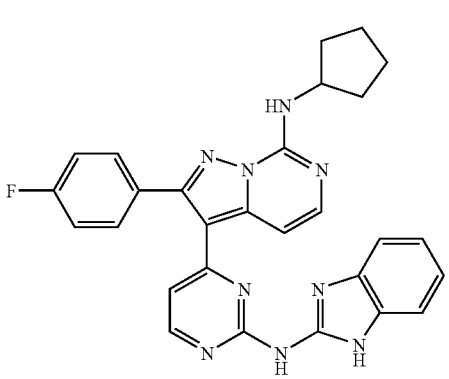

In a similar manner as described above, 3-[2-(1H-benzimidazol-2-ylamino)pyrimidin-4-yl]-N-cyclopentyl-2-(4fluorophenyl)pyrazolo[1,5-c]pyrimidin-7-amine (18 mg, 14%) was prepared from 1-[7-(cyclopentylamino)-2-(4-fluorophenyl)pyrazolo[1,5-c]pyrimidin-3-yl]-3-(dimethylamino)prop-2-en-1-one and N-(1H-benzimidazol-2-yl)guanidine. $^1$H NMR (CDCl$_3$): δ 8.40 (m, 1H), 7.80 (d, 1H), 7.66 (m, 3H), 7.37 (m, 1H), 7.17 (m, 7H), 6.71 (m, 1H), 6.44 (m, 1H), 4.56 (m, 1H), 2.18 (m, 2H), 1.62–1.87 (m, 6H). MS m/z 506 (M+1).

Example 17

N-Cyclopentyl-3-{2-[(4-fluorobenzyl)amino]pyrimidin-4-yl}-2-(4-fluorophenyl)pyrazolo[1,5-c]pyrimidin-7-amine

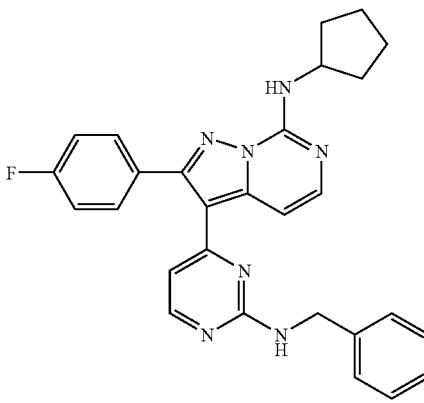

In a similar manner as described above, N-cyclopentyl-3-{2-[(4-fluorobenzyl)amino]pyrimidin-4-yl}-2-(4fluorophenyl)pyrazolo[1,5-c]pyrimidin-7-amine (21 mg, 17%) was prepared from 1-[7-(cyclopentylamino)-2-(4-fluorophenyl)pyrazolo[1,5-c]pyrimidin-3-yl]-3-(dimethylamino)

prop-2-en-1-one and N-(4-fluorobenzyl)guanidine trifluoroacetate. ¹H NMR (CDCl₃): δ 8.07 (d, 1H), 1.64 (d, 1H), 7.59 (dd, 2H), 7.33 (dd, 2H), 7.21 (bs, 1H), 7.13 (t, 2H), 7.02 (t, 2H), 6.34 (d, 1H), 6.31 (d, 1H), 5.42 (t, 1H), 4.62 (d, 2H), 4.49 (m, 1H), 2.11–2.20 (m, 2H) 1.74–1.83 (m, 2H), 1.59–1.72 (m, 4H). MS m/z 498 (M+1).

Example 18

N-Cyclopentyl-2-(4-fluorophenyl)-3-{2-[(2-phenylethyl)amino]pyrimidin-4-yl}pyrazolo[1,5-c]pyrimidin-7-amine

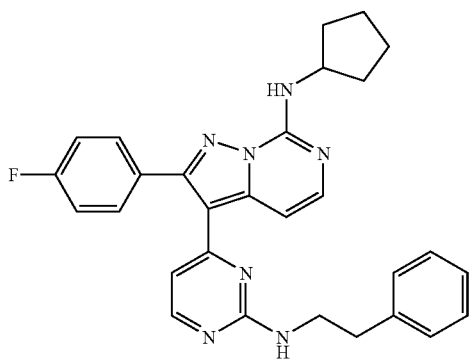

In a similar manner as described above, N-cyclopentyl-2-(4-fluorophenyl)-3-{2-[(2-phenylethyl)amino]pyrimidin-4-yl }pyrazolo[1,5-c]pyrimidin-7-amine (9 mg, 7%) was prepared from 1-[7-(cyclopentylamino)-2-(4-fluorophenyl)pyrazolo[1,5-c]pyrimidin-3-yl]-3-(dimethylamino)prop-2-en-1-one and N-(2-phenylethyl)guanidine sulfate. ¹H NMR (CDCl₃): δ 8.05 (d, 1H), 7.73 (d, 1H), 7.61 (dd, 2H), 7.48 (d, 1H), 7.31 (m, 2H), 7.23 (m, 3H), 7.13 (t, 2H), 6.37 (d, 1H), 6.28 (d, 1H). 5.14 (t, 1H), 4.51 (m, 1H), 3.71 (q, 2H), 2.94 (t, 2H), 2.16 (m, 2H), 1.75–1.85 (m, 2H), 1.62–1.73 (m, 4H). MS m/z 494 (M+1).

Example 19

3-[2-(tert-Butylamino)pyrimidin-4-yl]-N-cyclopentyl-2-(4-fluorophenyl)pyrazolo[1,5-c]pyrimidin-7-amine

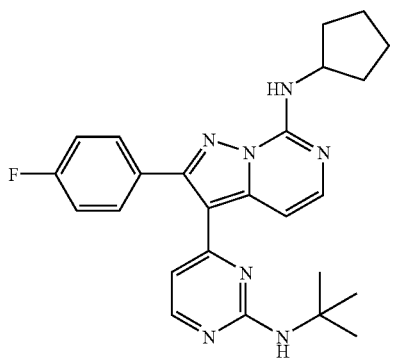

a) Methyl N-(tert-butyl)imidothiocarbamate hydroiodide

To a solution of t-butylthiourea (1.35 g, 10.2 mmol) in methanol (150 mL) was added iodomethane (2.13 g, 15.0 mmol). The solution was stirred overnight at room temperature. The reaction mixture was concentrated under reduced pressure to yield the title compound (2.8 g, >99%) as a yellow solid. ¹H NMR (CDCl₃): δ 9.07 (s, 1H), 8.6 (bs, 2H), 2.63 (s, 3H), 1.40 (s, 9H). MS m/z 147 (M+1).

b) N-(tert-Butyl)guanidine hydroiodide

N-(tert-Butyl)imidothiocarbamate hydroiodide (2.8 g, 10 mmol) was dissolved in a 2M NH3 solution in methanol (100 mL). The reaction mixture was heated to reflux for 3 hours and then removed from heat to stir at room temperature for 48 hours. The reaction mixture was concentrated under reduced pressure to leave the title compound (2.4 g, >99%) as a solid.

c) 3-[2-(tert-Butylamino)pyrimidin-4-yl]-N-cyclopentyl-2-(4-fluorophenyl)pyrazolo[1,5-c]pyrimidin-7-amine In a similar manner as described above, 3-[2-(tert-butylamino)pyrimidin-4-yl]-N-cyclopentyl-2-(4-fluorophenyl) pyrazolo[1,5-c]pyrimidin-7-amine (29 mg, 26%) was prepared from 1-[7-(cyclopentylamino)-2-(4-fluorophenyl) pyrazolo[1,5-c]pyrimidin-3-yl]-3-(dimethylamino)prop-2-en-1-one and N-(tert-butyl)guanidine hydroiodide. ¹H NMR (CDCl₃): δ 58.10 (d, 1H), 7.78 (d, 1H), 7.64 (dd, 2H), 7.45 (d, 1H), 7.17 (t, 2H), 6.42 (d, 1H), 6.31 (d, 1H), 5.16 (s, 1H), 4.56 (m, 1H), 2.22 (m, 2H), 1.63–1.90 (m, 15H). MS m/z 446 (M+1).

Example 20

N-Cyclopentyl-4-[2-(4-fluorophenyl)-7-(methylsulfanyl)pyrazolo[1,5-c]pyrimidin-3-yl]pyrimidin-2-amine

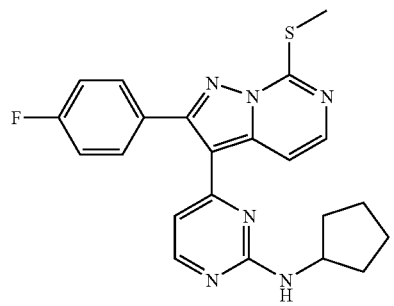

a) 1-[2-(4Fluorophenyl)-7-methylsulfanyl)pyrazolo[1,5-c]pyrimidin-3-yl]ethanone

To a slurry of 2-(4-fluorophenyl)-7-(methylsulfanyl)pyrazolo[1,5-c]pyrimidine (1.5 g, 5.9 mmol) in acetic anhydride (10 mL) was added 4 drops of sulfuric acid. The reaction mixture was heated to 80° C. for 2 hours, to 110° C. for 2 hours, and to reflux for 2 hours. The solution was allowed to cool to room temperature and stirred for 4 days. The mixture was poured into water (350 mL) and extracted with ethyl acetate (2×75 mL). The organic phase was washed with brine and concentrated under reduced pressure. The residue was purified by silica gel chromatography eluting with 2:98 acetone:dichloromethane to yield 1-[2-(4-fluorophenyl)-7-(methylsulfanyl)pyrazolo[1,5-c]pyrimidin-3-yl]ethanone (1.24 g, 70%). ¹H NMR (DMSO): δ 8.12 (d, 1H), 7.98 (d, 1H), 7.65 (dd, 2H), 7.24 (m, 2H), 2.77 (s, 3H), 2.23 (s, 3H). MS m/z 302 (M+1).- b) (2E)-3-(Dimethylamino)-1-[2-(4-fluorophenyl)-7-(methylsulfanyl)pyrazolo-[1,5-c]pyrimidin-3-yl]prop-2-en-1-one To 1-[2-(4-fluorophenyl)-7-(methylsulfanyl)pyrazolo[1,5-c]pyrimidin-3-yl]ethanone (1.24 g, 4.12 mmol) was added 1,1-di-tert-butoxy-N,N-dimethylmethanamine (15 mL) and the mixture heated to 120° C. for 1 hour. The reaction was allowed to cool to room temperature and stirred for 16 hours. The mixture was diluted with hexanes. The precipitate was collected by filtration and air dried to yield (2E)-3-(dimethylamino)-1-[2-(4-fluorophenyl)-7-(methylsulfanyl)pyrazolo[1,5-c]pyrimidin-3-yl]prop-2-en-1-one (880 mg, 60%). $^1$H NMR (DMSO): δ 8.03 (d, 1H), 7.72–7.82 (m, 3H), 7.57 (d, 1H), 7.37 (t, 2H), 5.08 (d, 1H), 3.04 (bs, 3H), 2.71 (s, 3H), 2.52 (bs, 3H). MS m/z 357 (M+1).

c) N-cyclopentyl-4-[2-(4-fluorophenyl)-7-(methylsulfanyl)pyrazolo[1,5-c]pyrimidin-3-yl]pyrimidin-2-amine To a solution of (2E)-3-(dimethylamino)-1-[2-(4-fluorophenyl)-7-(methylsulfanyl)pyrazolo[1,5-c]pyrimidin-3-yl]prop-2-en-1-one (660 mg, 1.85 mmol) and N-cyclopentylguanidine hydrochloride (600 mg, 3.71 mmol) in N,N-dimethylformamide (10 mL) was added potassium carbonate (760 mg, 5.55 mmol). The reaction mixture was heated to 100° C. for 1 hour and then to 115° C. for 4 hours. The reaction was allowed to cool to room temperature and diluted with water. The mixture was extracted with ethyl acetate, washed with brine, dried over magnesium sulfate, filtered and concentrated. The residue was purified using silica gel chromatography eluting with 50% acetone in dichloromethane to yield N-cyclopentyl-4-[2-(4-fluorophenyl)-7-(methylsulfanyl)pyrazolo[1,5-c]pyrimidin-3-yl]pyrimidin-2-amine (210 mg, 32%). $^1$H NMR (CDCl$_3$): δ 8.05 (d,1H), 7.94 (m, 2H), 7.64 (dd, 2H), 7.13 (t, 2H), 6.29 (d, 1H), 5.21 (bs, 1H), 4.31 (m, 1H), 2.72 (s, 3H), 2.06 (m, 2H), 1.49–1.82 (m, 6H). MS m/z 421 (M+1).

Example 21

N-Cyclopentyl-3-[2-(cyclopentylamino)pyrimidin-4-yl]-2-(4-methoxyphenyl)pyrazolo[1,5-c]pyrimidin-7-amine

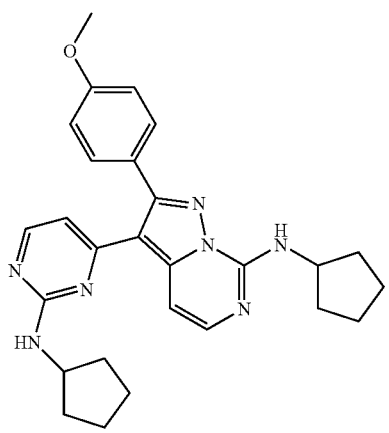

In a similar manner as described above N-cyclopentyl-3-[2-(cyclopentylamino)pyrimidin-4-yl]-2-(4-methoxyphenyl)pyrazolo[1,5-c]pyrimidin-7-amine (610 mg, 66%) was prepared as a brown solid. $^1$H NMR (CDCl$_3$) δ 8.02 (d, 1H), 7.73 (d, 1H), 7.57–7.52 (m, 3H), 6.98 (d, 2H), 6.40 (d, 1H), 6.30 (d, 1H), 5.12 (d, 1H), 4.51 (m, 1H), 4.32 (m, 1H), 3.87 (s, 3H), 2.18–2.03 (m, 4H), 1.81–1.49 (m, 12H); MS m/z 470 (M+1).

Example 22

4-{7-(Cyclopentylamino)-3-[2-(cyclopentylamino)pyrimidin-4-yl]pyrazolo[1,5-c]pyrimidin-2-yl}phenol

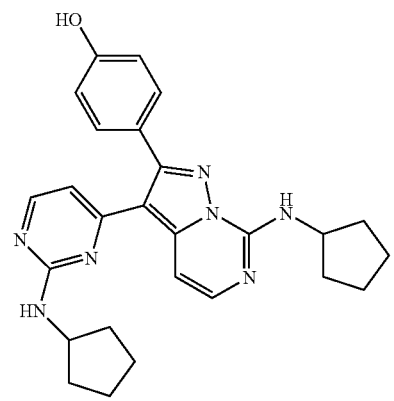

In a similar manner as described above 4-{7-(cyclopentylamino)-3-[2-(cyclopentylamino)pyrimidin-4-yl]pyrazolo[1,5-c]pyrimidin-2-yl}phenol (535 mg, 90%) was prepared as a yellow solid. $^1$H NMR (DMSO) δ 9.82 (s, 1H), 8.02 (d, 1H), 7.84–7.77 (m, 2H), 7.40 (d, 2H), 6.88 (d, 2H), 6.27 (m, 1H), 4.51–4.44 (m, 1H), 1.99–1.93 (m, 3H), 1.73–1.55 (m, 11H), 1.27–1.24 (m, 3H), 0.88–0.83 (m, 2H); MS m/z 456 (M+1).

Example 23

N-Cyclopentyl-3-[2-(cyclopentylamino)pyrimidin-4-yl]-2-[4-(cyclopropylmethoxy)phenyl]pyrazolo[1,5-c]pyrimidin-7-amine

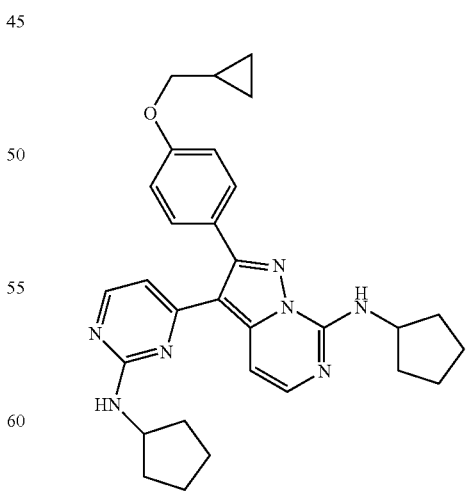

In a similar manner as described above N-cyclopentyl-3-[2-(cyclopentylamino)pyrimidin-4-yl]-2-[4-(cyclopropylmethoxy)phenyl]pyrazolo[1,5-c]pyrimidin-7-amine (170 mg, 76%) was prepared as a brown solid. $^1$H NMR (CDCl$_3$) δ 8.02 (d, 1H), 7.73 (d, 1H), 7.55–7.52 (m, 3H), 6.99–6.96 (m, 2H), 6.39 (d, 1H), 6.30 (d, 1H), 5.05 (d, 1H), 4.54–4.49 (m, 1H), 4.35–4.30 (m, 1H), 3.86 (d, 2H), 2.18–2.05 (m, 3H), 1.80–1.60 (m, 7H), 1.56–1.51 (m, 7H), 0.68–0.65 (m, 2H), 0.39–0.37 (m, 2H); MS m/z 510 (M+1).

Example 24

3-[2-(Cyclopentylamino)pyrimidin-4-yl]-N-cyclopropyl-2-(4-methoxyphenyl)pyrazolo[1,5-c]pyrimidin-7-amine

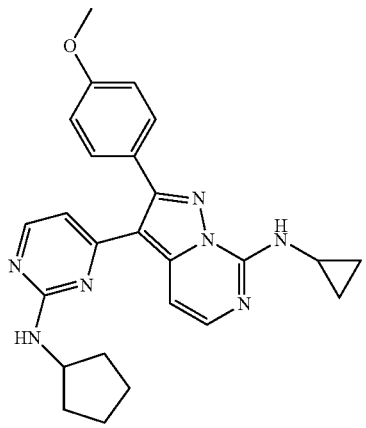

In a similar manner as described above 3-[2-(cyclopentylamino)pyrimidin-4-yl]-N-cyclopropyl-2-(4methoxyphenyl)pyrazolo[1,5-c]pyrimidin-7-amine (150 mg, 56%) was prepared as a white solid. $^1$H NMR (CDCl$_3$) δ 8.03 (d, 1H), 7.813 (d, 1H), 7.60 (m, 1H), 7.55–7.52 (m, 2H), 6.99–6.96 (m, 2H), 6.63 (m,1H), 6.30 (d, 1H), 5.09 (m, 1H), 4.33 (m, 1H), 3.87 (s, 3H), 2.99 (m, 1H), 2.09–2.04 (m, 3H), 1.77–1.65 (m, 5H), 0.97–0.92 (m, 2H), 0.78–0.74 (m, 2H); MS m/Z 442 (M+1).

Example 25

2-(4-Butoxyphenyl)-N-cyclopentyl-3-[2-(cyclopentylamino)pyrimidin-4-yl]pyrazolo[1,5-c]pyrimidin-7-amine

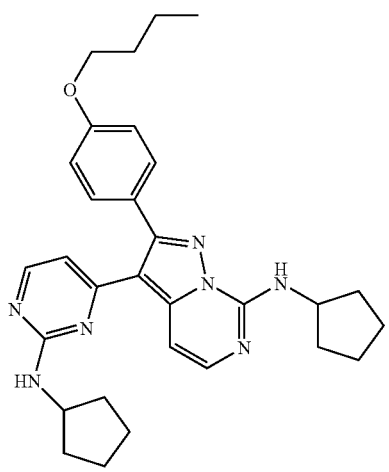

In a similar manner as described above 2-(4-butoxyphenyl)-N-cyclopentyl-3-[2-(cyclopentylamino) pyrimidin-4-yl]pyrazolo[1,5-c]pyrimidin-7-amine was prepared as a white solid. $^1$H NMR (CDCl$_3$) δ 8.02 (d, 1H), 7.73 (d, 1H), 7.55–7.52 (m, 3H), 6.97 (m, 2H), 6.40 (d, 1H), 6.31 (d, 1H), 5.09 (d, 1H), 4.51 (m, 1H), 4.32 (m, 1H), 4.02 (t, 2H), 2.19–2.04 (m, 5H), 1.85–1.48 (m, 15H), 0.99 (m, 3H); MS m/z 512 (M+1).

Example 26

N-Cyclopentyl-3-[2-(cyclopentylamino)pyrimidin-4-yl]-2-(4-isobutoxyphenyl)pyrazolo[1,5-c]pyrimidin-7-amine

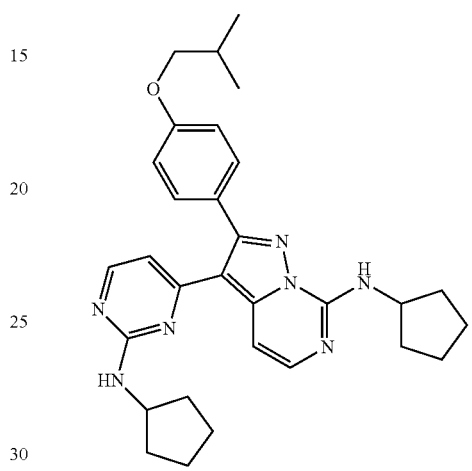

In a similar manner as described above N-cyclopentyl-3-[2-(cyclopentylamino)pyrimidin-4-yl]-2-(4-isobutoxyphenyl)pyrazolo[1,5-c]pyrimidin-7-amine was prepared as a tan solid. $^1$H NMR (CDCl$_3$), δ 8.02 (d, 1H), 7.73 (d, 1H), 7.55–7.52 (m, 3H), 6.97 (m, 2H), 6.39 (d, 1H), 6.31 (d, 1H), 5.07 (d, 1H), 4.51 (m, 1H), 4.33 (m, 1H), 3.77 (d, 2H), 2.19–2.04 (m, 5H), 1.79–1.49 (m, 12H), 1.05(d, 6H); MS m/z 512 (M+1).

Example 27

N-Cyclopentyl-3-[2-(cyclopentylamino)pyrimidin-4-yl]-2-[4-(2-methoxyethoxy)phenyl]pyrazolo[1,5-c]pyrimidin-7-amine

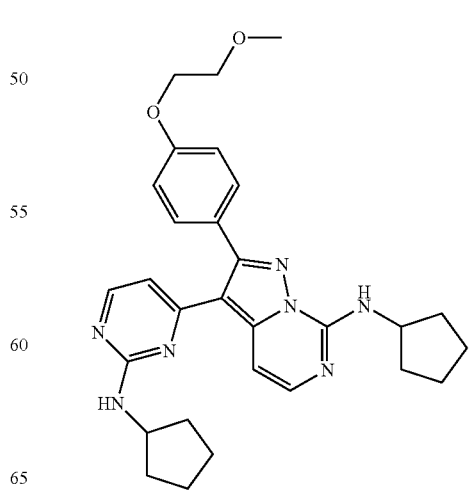

In a similar manner as described above N-cyclopentyl-3-[2-(cyclopentylamino)pyrimidin-4-yl]-2-[4-(2-methoxyethoxy)phenyl]pyrazolo[1,5-c]pyrimidin-7-amine was prepared as a yellow solid. $^{1}$H NMR (CDCl$_{3}$) δ 8.02 (d, 1H), 7.73 (d, 1H), 7.55–7.52 (m, 3H), 7.00 (m, 2H), 6.39 (d, 1H), 6.27 (d, 1H), 5.10 (d, 1H), 4.51 (m, 1H), 4.33 (m, 1H), 4.18 (m, 2H), 3.78 (m, 2H), 3.47 (s, 3H), 2.18–2.03 (m, 4H), 1.78–1.49 (m, 12H); MS m/z 514 (M+1).

Example 28

N-Cyclopentyl-3-[2-(cyclopentylamino)pyrimidin-4-yl]-2-(4-propoxyphenyl)pyrazolo[1,5-c]pyrimidin-7-amine

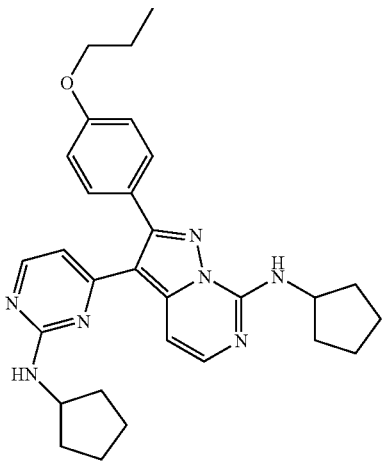

In a similar manner as described above N-cyclopentyl-3-[2-(cyclopentylamino)pyrimidin-4yl]-2-(4-propoxyphenyl)pyrazolo[1,5-c]pyrimidin-7-amine was prepared as a yellow solid. $^{1}$H NMR (CDCl$_{3}$) δ 8.02 (d, 1H), 7.73 (d, 1H), 7.55–7.52 (m, 3H), 6.97 (m, 2H), 6.40 (d, 1H), 6.31 (d, 1H), 5.10 (d, 1H), 4.5 (m, 1H), 4.33 (m, 1H), 3.98 (t, 2H), 2.19–2.05 (m, 1H), 1.87–1.5 (m, 14H), 1.06 (t, 3H); MS m/z 498 (M+1).

Example 29

N-(tert-Butyl)-3-[2-(cyclopentylamino)pyrimidin-4-yl]-2-(4-fluorophenyl)pyrazolo[1,5-c]pyrimidin-7-amine

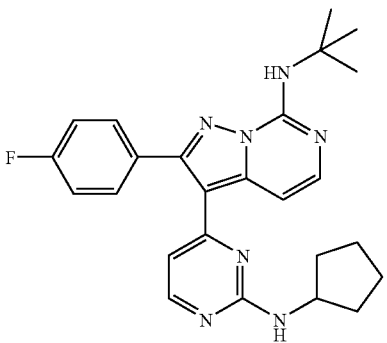

To a solution of N-cyclopentyl-4-[2-(4-fluorophenyl)-7-(methylsulfanyl)pyrazolo[1,5-c]pyrimidin-3-yl]pyrimidin-2-amine (40 mg, 0.095 mmol) in dichloromethane (2 mL) was added 3-chloroperoxybenzoic acid (12 mg, 0.14 mmol) and the reaction mixture stirred at room temperature for 1 hour. t-Butylamine (3 mL) was added and heated to reflux for 3 hours. The reaction was allowed to cool and diluted with water. The mixture was extracted with ethyl acetate and the organic phase washed with brine before being concentrated under vacuum. The residue was purified by silica gel chromatography eluting with SO/5 acetone in dichloromethane to yield a 1:1 mixture of starting material and product. The residue was dissolved in dichloromethane (2 mL) and 3-chloroperoxybenzoic acid (18 mg, 0.21 mmol) was added. The mixture was stirred for 2 hours and then t-butylamine (3 mL) was added. The reaction mixture was stirred for 3 hours, diluted with water, extracted with ethyl acetate, washed with brine, concentrated, and the residue purified by silica gel chromatography eluting with 5% acetone in dichloromethane to yield N-(tert-butyl)-3-[2-(cyclopentylamino)pyrimidin-4-yl]-2-(4-fluorophenyl)pyrazolo[1,5-c]pyrimidin-7-amine (6 mg, 14%), $^{1}$H NMR (CDCl$_{3}$): δ 8.02 (d, 1H), 7.72 (d, 1H), 7.60 (dd, 2H), 7.47 (d, 1H), 7.13 (t, 2H), 6.42 (s, 1H), 6.25 (d, 1H), 5.14 (bs, 1H), 4.28 (m, 1H), 2.04 (m, 2H), 1.45–1.78 (m, 15H). MS m/z 446 (M+1).

Example 30

N-Cyclopentyl-4-[2-(4-fluorophenyl)-7-pyrrolidin-1-ylpyrazolo[1,5-c]pyrimidin-3-yl]pyrimidin-2-amine

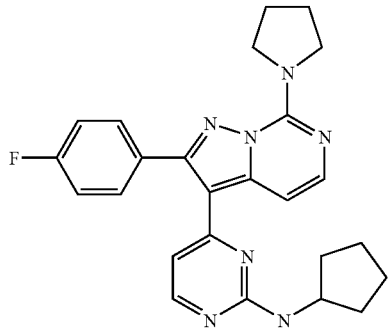

To a solution of N-cyclopentyl-4-[2-(4-fluorophenyl)-7-(methylsulfanyl)pyrazolo[1,5-c]pyrimidin-3-yl]pyrimidin-2-amine (24 mg, 0.057 mmol) in dichloromethane (3 mL) was added 3-chloroperoxybenzoic acid (15mg, 0.086 mmol) and the reaction mixture stirred for 1 hour. Pyrrolidine (3 mL) was added and the reaction mixture stirred for 2 hours before being diluted with dichloromethane. The organic phase was washed with saturated sodium bicarbonate, washed with brine, and concentrated under reduced pressure. The residue was purified by silica gel chromatography eluting with 5% acetone in dichloromethane to yield N-cyclopentyl-4-[2-(4-fluorophenyl)-7-pyrrolidin-1-ylpyrazolo[1,5-c]pyrimidin-3-yl]pyrimidin-2-amine (15 mg, 59%). $^{1}$H NMR (CDCl$_{3}$): δ 8.05 (d, 1H), 7.65 (d, 1H), 7.60 (dd, 2H), 7.43 (d,1H), 7.10 (t, 2H), 6.27 (d, 1H), 5.05 (d, 1H), 4.29 (m, 1H), 4.09 (t, 4H), 1.99 (m, 6H), 1.45–1.78 (m, 6H). MS m/z 444 (M+1).

Example 31

N-Cyclopentyl-4-[2-(4-fluorophenyl)-7-piperidin-1-ylpyrazolo[1,5-c]pyrimidin-3-yl]pyrimidin-2-amine

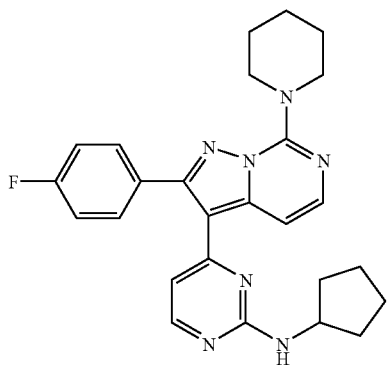

In a similar manner as described above, N-cyclopentyl-4-[2-(4-fluorophenyl)-7-piperidin-1-ylpyrazolo[1,5-c]pyrimidin-3-yl]pyrimidin-2-amine (25 mg, 45%) was prepared from N-cyclopentyl-4-[2-(4-fluorophenyl)-7-(methylsulfanyl)pyrazolo[1,5-c]pyrimidin-3-yl]pyrimidin-2-amine and piperidine. $^1$H NMR (CDCl$_3$): δ 8.06 (d, 1H), 7.73 (d, 1H), 7.63 (m, 3H), 7.11 (t, 2H), 6.29 (d,1H), 5.08 (m,1H) 4.29 (m,1H),3.91 (m, 4H), 2.05 (m, 2H), 1.68–1.80 (m, 9H), 1.63 (m, 1H), 1.51 (m,2H). MS m/z 458 (M+1).

Example 32

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "T" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of detection DNA.

For the detection probe, a gel-purified, digoxigenin-labeled, 710-bp PCR fragment of the HSV UL-15 sequence was utilized. PCR conditions included 0.5 μM primers, 180 μM dTTP, 20 μM dUTP-digoxigenin (Boehringer Mannheim 1558706), 200 μM each of dATP, dCTP, and dGTP, 1×PCR Buffer II (Perkin Elmer), 2.5 mM, MgCl$_2$, 0.025 units/μL of AmpliTaq Gold polyerase (Perkin Elmer), and 5 ng a gel-purified HSV DNA per 100 μL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of capture plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μl/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5× Denhardt's solution, 0.25× APE, and 5 ng of the digoxigenin-labeled detection probe). APE is 1.5 M NH$_4$-acetate, 0.15 M NH$_4$H$_2$phosphate, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Vietor reader.

e) Results.

The following results were obtained for HSV-1.

| Example No. | IC$_{50}$ (μM) |
| --- | --- |
| 1 | 0.72 |
| 2 | 5.5 |
| 3 | 3.9 |
| 4 | 11.3 |
| 5 | 0.46 |
| 6 | 0.20 |
| 7 | 0.30 |
| 8 | 2.5 |
| 9 | 7.1 |
| 10 | 0.12 |
| 11 | 6.4 |
| 12 | 1 |
| 13 | 1.5 |
| 14 | >40 |
| 15 | >40 |

-continued

| Example No. | IC$_{50}$ (μM) |
| --- | --- |
| 16 | >40 |
| 17 | 2 |
| 18 | 3.5 |
| 19 | 3 |
| 20 | >40 |
| 21 | 0.4 |
| 22 | 4 |
| 23 | 0.5 |
| 24 | 1 |
| 25 | 0.6 |
| 26 | 0.5 |
| 27 | 1 |
| 28 | 0.5 |
| 29 | 7 |
| 30 | 2 |
| 31 | 1 |

The results demonstrate that the compounds of the present invention are useful for the treatment and prophylaxis of herpes viral infections.

The invention claimed is:

1. A compound of formula (I):

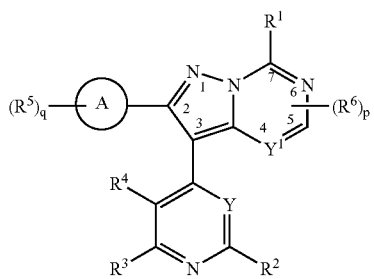

I wherein:
R$^1$ is selected from the group consisting of H, halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_n$Ay, —S(O)$_n$Het, —S(O)$_2$NR$^7$R$^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$C(O)Het, —R$^{10}$CO$_2$R$^9$, —R$^{10}$OC(O)R$^9$, —R$^{10}$OC(O)Ay, —R$^{10}$OC(O)Het, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido;

each R$^7$ and R$^8$ are the same or different and are independently selected from the group consisting of H, alkyl, cycloalkyl, alkenyl, cycloalkenyl, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$Ay, —R$^{10}$Het, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$OR$^9$, —R$^{10}$NR$^9$R$^{11}$, —R$^{10}$NHCOR$^9$, —R$^{10}$NHC(NH)NR$^9$R$^{11}$, —R$^{10}$C(NH)NR$^9$R$^{11}$, —R$^{10}$NHSO$_2$R$^9$, —R$^{10}$SO$_2$NR$^9$R$^{11}$, —R$^{10}$SO$_2$R$^{10}$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$^{10}$(OR$^{10}$), where w is 1–10, and —R$^{10}$NR$^{10}$R$^{10}$;

each R$^{10}$ is the same or different and is independently selected from the group consisting of alkyl, cycloalkyl, alkenyl, cycloalkenyl, and alkynyl;

n is 0, 1 or 2;

Ay is aryl;

Het is a 5- or 6-membered heterocyclic or heteroaryl group;

Y$^1$ is CH;

p is 0, 1 or 2 when Y$^1$ is CH, each R$^6$ is the same or different and is independently selected from the group consisting of H, halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_n$Ay, —S(O)$_n$Het, —S(O)$_2$NR$^7$R$^8$, —S(O)$_2$NR$^7$Ay, —R$^{10}$cycloalkyl, —R$^{10}$Ay, —R$^{10}$Het, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$C(O)Het, —R$^{10}$CO$_2$R$^9$, —R$^{10}$OC(O)R$^9$, —R$^{10}$OC(O)Ay, —R$^{10}$OC(O)Het, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido;

Y is N or CH;

R$^2$ is selected from the group consisting of halo, alkyl, cycloalkyl, alkenyl, cycloalkenyl, Ay, Het, —OR$^7$, —OAy, —OHet —NR$^7$R$^8$, —NR$^7$Ay, —NHHet, —S(O)$_n$R$^9$, —S(O)$_n$Ay, —R$^{10}$NR$^7$R$^8$ and —R$^{10}$NR$^7$Ay;

R$^3$ and R$^4$ are the same or different and are each independently selected from the group consisting of H, halo, alkyl, alkenyl, cycloalkyl, Ay, Het, —C(O)R$^7$, C(O)Ay, —CO$_2$R$^7$, —CO$_2$Ay, —OR$^7$, —OAy, —NR$^7$R$^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7$R$^8$ and —R$^{10}$NR$^7$Ay;

Ring A is selected from the group consisting of aryl, 5–10 membered heterocyclic group and a 5–10 membered heteroaryl group;

q is 0, 1, 2, 3, 4 or 5; and each R$^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —NR$^7$R$^8$, —NR$^7$Ay, —NHHet, —S(O)$_n$R$^9$, —S(O)$_2$NR$^7$R$^8$, —S(O)$_2$NR$^7$Ay, —R$^{10}$cycloalkyl, —R$^{10}$Het, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido; or a pharmaceutically acceptable salt, thereof.

2. The compound according to claim 1 wherein R$^1$ is selected from the group consisting of halo, alkyl, cycloalkyl, Ay, Het, —OR$^7$, —OAy, —NR$^7$R$^8$, —NR$^7$Ay, —NHHet, —S(O)$_n$R$^9$, —R$^{10}$cycloalkyl, —R$^{10}$OR$^9$, —R$^{10}$NR$^7$R$^8$ and —R$^{10}$NR$^7$Ay.

3. The compound according to claim 1 wherein R$^1$ is selected from the group consisting of alkyl, Het, —OR$^7$, —NR$^7$R$^8$, —NR$^7$Ay and —S(O)$_n$R$^9$.

4. The compound according to claim 1 wherein p is 0 or 1.

5. The compound according to claim 1 wherein each $R^6$ is the same or different and is independently selected from the group consisting of halo, alkyl, Ay, Het, —C(O)Het, —CO$_2$R$^9$, —C(O)NR$^7$R$^8$, —C(O)NR$^7$Ay, —OR$^7$, —OAy, —NR$^7$R$^8$, —NR$^7$Ay, —NHHet, —S(O)$_n$R$^9$, —S(O)$_n$Ay, —S(O)$_n$Het, —R$^{10}$OR$^9$ and cyano.

6. The compound according to claim 1 wherein each $R^6$ is the same or different and is independently selected from the group consisting of halo, alkyl, Het, —NR$^7$R$^8$, —NHHet and —S(O)$_n$R$^9$.

7. The compound according to claim 1 wherein Y is CH.

8. The compound according to claim 1 wherein Y is N.

9. The compound according to claim 1 wherein $R^2$ is selected from the group consisting of Ay, Het, —OR$^7$, —OAy, —OHet, —NR$^7$R$^8$, —NR$^7$Ay, —NHHet, —S(O)$_n$R$^9$, —S(O)$_n$Ay, —R$^{10}$NR$^7$R$^8$ and —R$^{10}$NR$^7$Ay.

10. The compound according to claim 1 wherein $R^2$ is selected from the group consisting of —NR$^7$R$^8$, —NR$^7$Ay and —NHHet.

11. The compound according to claim 1 wherein $R^3$ and $R^4$ are the same or different and are each independently selected from the group consisting of H, halo, alkyl, Ay, —CO$_2$R$^7$, —OR$^7$, —NR$^7$R$^8$, —R$^{10}$NR$^7$ and —R$^{10}$NR$^7$R$^8$.

12. The compound according to claim 1 wherein $R^3$ and $R^4$ are both H.

13. The compound according to claim 1 wherein Ring A is selected from the group consisting of aryl, a 5–6 membered heterocyclic or heteroaryl group and a 9-membered heterocyclic or heteroaryl group.

14. The compound according to claim 1 wherein Ring A is selected from the group consisting of phenyl, naphthyl, furan, pyridine, pyrimidine, thiazol, pyrazine, pyrrole, imidazole, oxazole, benzimidazole, quinoline, isoquinoline and quinoxoline.

15. The compound according to claim 1 wherein Ring A is selected from the group consisting of phenyl, furan, pyridine and pyrimidine.

16. The compound according to claim 1 wherein Ring A is phenyl.

17. The compound according to claim 1 wherein q is 0, 1 or 2.

18. The compound according to claim 1 wherein each $R^5$ is the same or different and is independently selected from the group consisting of halo, alkyl, alkenyl, Ay, Het, —CO$_2$R$^9$, —C(O)NR$^7$R$^8$, —C(O)NR$^7$Ay, —OR$^7$, —OAy, —NR$^7$R$^8$, —NR$^7$Ay, —S(O)$_2$NR$^7$R$^8$, cyano, nitro and azido.

19. The compound according to claim 1 wherein each $R^5$ is the same or different and is independently selected from the group consisting of halo, alkyl, —OR$^7$, —NR$^7$R$^8$ and cyano.

20. A compound selected from the group consisting of:
N-Cyclopentyl-3-[2-(cyclopentylamino)pyrimidin-4-yl]-2-(4-fluorophenyl)pyrazolo[1,5-c]pyrimidin-7-amine;
N-Cyclopentyl-3-[2-(cyclopropylamino)pyrimidin-4-yl]-2-(4-fluorophenyl)pyrazolo[1,5-c]pyrimidin-7-amine;
4-[2-(3-Chlorophenyl)pyrazolo[1,5-c]pyrimidin-3-yl]-N-cyclopentylpyrimidin-2-amine;
4-[2-(3-Chlorophenyl)-7-(methylthio)pyrazolo[1,5-c]pyrimidin-3-yl]-N-cyclopentylpyrimidin-2-amine;
2-(3-Chlorophenyl)-N-cyclopentyl-3-[2-(cyclopentylamino)-4-pyrimidinyl]pyrazolo[1,5-c]pyrimidin-7-amine;
4-[2-(3-Chlorophenyl)-7-(4-morpholinyl)pyrazolo[1,5-c]pyrimidin-3-yl]-N-cyclopentyl-2-pyrimidinamine;
2-(3-Chlorophenyl)-3-[2-(cyclopentylamino)-4-pyrimidinyl]-N-(2-methoxyethyl)pyrazolo[1,5-c]pyrimidin-7-amine;
2-(3-Chlorophenyl)-3-[2-(cyclopentylamino)-4-pyrimidinyl]pyrazolo[1,5-c]pyrimidin-7-ol;
3-[2-(Butylamino)pyrimidin-4-yl]-N-cyclopentyl-2-(4-fluorophenyl)pyrazolo[1,5-c]pyrimidin-7-amine;
3-(2-Anilinopyrimidin-4-yl)-N-cyclopentyl-2-(4-fluorophenyl)pyrazolo[1,5-c]pyrimidin-7-amine;
3-[2-(1,3-Benzothiazol-2-ylamino)pyrimidin-4-yl]-N-cyclopentyl-2-(4-fluorophenyl)pyrazolo[1,5-c]pyrimidin-7-amine;
N-Cyclopentyl-2-(4-fluorophenyl)-3-{2-[(4-methyl-1,3-thiazol-2-yl)amino]pyrimidin-4-yl}pyrazolo[1,5-c]pyrimidin-7-amine;
3-[2-(1H-Benzimidazol-2-ylamino)pyrimidin-4-yl]-N-cyclopentyl-2-(4-fluorophenyl)pyrazolo[1,5-c]pyrimidin-7-amine;
N-Cyclopentyl-3-{2-[(4-fluorobenzyl)amino]pyrimidin-4-yl}-2-(4-fluorophenyl)pyrazolo[1,5-c]pyrimidin-7-amine;
N-Cyclopentyl-2-(4-fluorophenyl)-3-{2-[(2-phenylethyl)amino]pyrimidin-4-yl}pyrazolo[1,5-c]pyrimidin-7-amine;
3-[2-(tert-Butylamino)pyrimidin-4-yl]-N-cyclopentyl-2-(4-fluorophenyl)pyrazolo[1,5-c]pyrimidin-7-amine;
N-Cyclopentyl-4-[2-(4-fluorophenyl)-7-(methylsulfanyl)pyrazolo[1,5-c]pyrimidin-3-yl]pyrimidin-2-amine;
N-Cyclopentyl-3-[2-(cyclopentylamino)pyrimidin-4-yl]-2-(4-methoxyphenyl)pyrazolo[1,5-c]pyrimidin-7-amine;
4-{7-(Cyclopentylamino)-3-[2-(cyclopentylamino)pyrimidin-4-yl]pyrazolo[1,5-c]pyrimidin-2-yl}phenol;
3-[2-(Cyclopentylamino)pyrimidin-4-yl]-N-cyclopropyl-2-(4-methoxyphenyl)pyrazolo-[1,5-c]pyrimidin-7-amine;
2-(4-Butoxyphenyl)-N-cyclopentyl-3-[2-(cyclopentylamino)pyrimidin-4-yl]pyrazolo[1,5-c]pyrimidin-7-amine;
N-Cyclopentyl-3-[2-(cyclopentylamino)pyrimidin-4-yl]-2-(4-isobutoxyphenyl)pyrazolo[1,5-c]pyrimidin-7-amine;
N-Cyclopentyl-3-[2-(cyclopentylamino)pyrimidin-4-yl]-2-[4-(2-methoxyethoxy)phenyl]pyrazolo[1,5-c]pyrimidin-7-amine;
N-Cyclopentyl-3-[2-(cyclopentylamino)pyrimidin-4-yl]-2-(4-propoxyphenyl)pyrazolo[1,5-c]pyrimidin-7-amine;
N-(tert-Butyl)-3-[2-(cyclopentylamino)pyrimidin-4-yl]-2-(4-fluorophenyl)pyrazolo[1,5-c]pyrimidin-7-amine;
N-Cyclopentyl-4-[2-(4-fluorophenyl)-7-pyrrolidin-1-ylpyrazolo[1,5-c]pyrimidin-3-yl]pyrimidin-2-amine; and
N-Cyclopentyl-4-[2-(4-fluorophenyl)-7-piperidin-1-ylpyrazolo[1,5-c]pyrimidin-3-yl]pyrimidin-2-amine,
or a pharmaceutically acceptable salt, thereof.

21. A pharmaceutical composition comprising a compound according to claim 1 and a pharmaceutically acceptable carrier.

22. The pharmaceutical composition according to claim 21 further comprising an antiviral agent selected from the group consisting of aciclovir and valaciclovir.

23. A method for the treatment of a herpes viral infection selected from herpes simplex virus 1 and herpes simplex virus 2, in an animal, said method comprising administering to the animal a therapeutically effective amount of a compound according to claim 1.

24. A method for the treatment of a condition or disease associated with a herpes viral infection selected from herpes simplex virus 1 and herpes simplex virus 2, in an animal, comprising administering to the animal a therapeutically effective amount of the compound of formula (I) according to claim 1.

25. A process for preparing a compound according to claim 1 wherein $Y^1$ is CH; Y is N; $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NH Het —$S(O)_nR^9$, —$S(O)_n$Ay, $R^{10}NR^7R^8$ and —$R^{10}NR^7$Ay; and $R^3$ and $R^4$ are H, said process comprising reacting a compound of formula (XX):

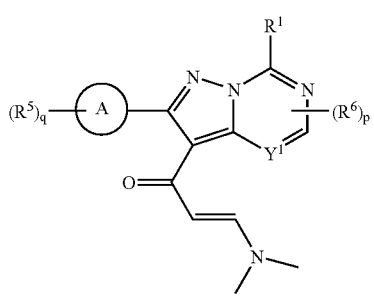

XX with a compound of formula (XXI):

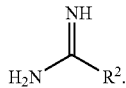

XXI

26. A process for preparing a compound according to claim 1 wherein Y is N; $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NH-Het —$S(O)_nR^9$, —$S(O)_n$Ay, —$R^{10}NR^7R^8$ and —$R^{10}NR^7$Ay; $R^3$ is selected from the group consisting of H, alkyl, alkenyl, cycloalkyl, Ay, Het, —$C(O)R^7$, $C(O)$Ay, —$CO_2R^7$, —$CO_2$Ay, —$OR^7$, —OAy, —$NR^7R^8$ (where $R^7$ and $R^8$ are not H), —$NR^7$Ay (where $R^7$ is H), —$SO_2NHR^9$, —$R^{10}OR^7$, —$R^{10}$cycloalkyl, —$R^{10}$OAy, —$R^{10}NR^7R^8$ and —$R^{10}NR^7$Ay; and $R^4$ is H said process comprising reacting a compound of formula (XXV):

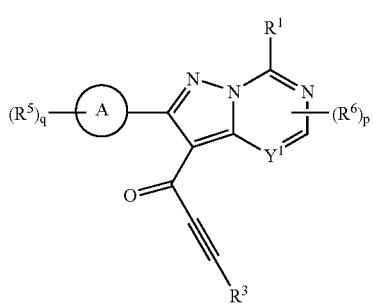

XXV with a compound of formula (XXI):

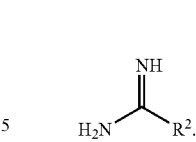

XXI

27. A process for preparing a compound according to claim 1 wherein Y is N and $R^2$ is selected from the group consisting of alkyl, cycloalkyl, alkenyl, cycloalkenyl, Ay, Het, —$OR^7$, —OAy, —OHet —$NR^7R^8$, —$NR^7$Ay, —NH-Het —$S(O)_nR^9$, —$S(O)_n$Ay, —$R^{10}NR^7R^8$ and —$R^{10}NR^7$Ay, said process comprising the steps of:

a) reacting a compound of formula (XXVIII):

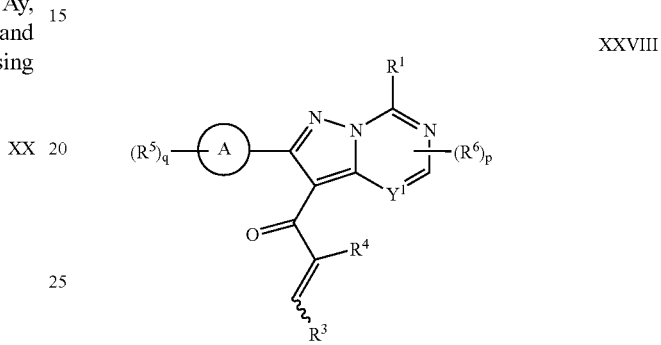

XXVIII with a compound of formula (XXI):

XXI to prepare an intermediate compound; and b) oxidizing the intermediate compound.

28. A process for preparing a compound according to claim 1 comprising reacting a compound of formula (XXX):

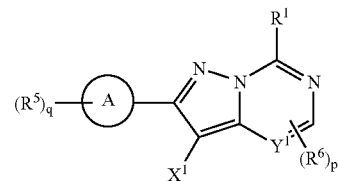

XXX wherein $X^1$ is chloro, bromo or iodo;

with a compound of formula (X):

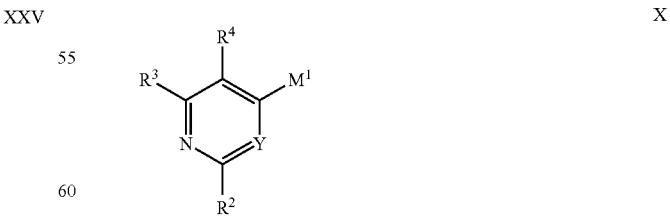

X wherein $M^1$ is —$B(OH)_2$, —$B(ORa)_2$, —$B(Ra)_2$, —Sn$(Ra)_3$, Zn-halide, ZnRa, or Mg-halide where Ra is alkyl or cycloalkyl and halide is halo.

* * * * *

UNITED STATES PATENT AND TRADEMARK OFFICE
CERTIFICATE OF CORRECTION

PATENT NO. : 7,247,626 B2
APPLICATION NO. : 10/505386
DATED : July 24, 2004
INVENTOR(S) : Gudmundsson et al.

It is certified that error appears in the above-identified patent and that said Letters Patent is hereby corrected as shown below:

Column 93, Claim 11, line 25 should read
-- $CO_2R^7$, -$OR^7$, -$NR^7R^8$, -$R^{10}OR^7$ and -$R^{10}NR^7R^8$, --

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,247,626 B2  
APPLICATION NO. : 10/505386  
DATED : July 24, 2007  
INVENTOR(S) : Gudmundsson et al.

It is certified that error appears in the above-identified patent and that said Letters Patent is hereby corrected as shown below:

Column 93, Claim 11, line 25 should read
-- $CO_2R^7$, -$OR^7$, -$NR^7R^8$, -$R^{10}OR^7$ and –$R^{10}NR^7R^8$, --

This certificate supersedes the Certificate of Correction issued June 10, 2008.

Signed and Sealed this

Fifteenth Day of July, 2008

JON W. DUDAS  
*Director of the United States Patent and Trademark Office*